(12) United States Patent
Wang et al.

(10) Patent No.: US 6,780,984 B2
(45) Date of Patent: Aug. 24, 2004

(54) METHOD FOR PROGNOSING CANCER AND THE PROTEINS INVOLVED

(75) Inventors: Zhou Wang, Chicago, IL (US); Wuhan Xiao, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/906,393

(22) Filed: Jul. 16, 2001

(65) Prior Publication Data

US 2003/0039970 A1 Feb. 27, 2003

Related U.S. Application Data

(60) Provisional application No. 60/218,761, filed on Jul. 17, 2000.

(51) Int. Cl.[7] ..................... C07H 21/02; C12N 15/00; C12N 1/20; C12P 21/06
(52) U.S. Cl. ............... 536/23.1; 536/23.1; 435/320.1; 435/252.1; 435/69.1
(58) Field of Search ............... 536/23.1; 435/320.1, 435/252.1, 69.1

(56) References Cited

U.S. PATENT DOCUMENTS 4,889,806 A * 12/1989 Olson et al.
5,821,352 A    10/1998 Heintz et al.
5,928,871 A     7/1999 Heintz et al.
5,968,781 A * 10/1999 Yoon et al.

OTHER PUBLICATIONS

Wang et al (PNAS, 94:12999–13004).*
Sambrook et al (Molecular Cloning, a Laboratory manuary, 1989, Cold Springer Harbor PRess, p. 16.3–4).*
Lazer et al (Mol. Cell. Bio., 1988, 8:1247–1252).*
Harris et al (J. Am. Soc. Nephrology, 1995, 6:1125–1133).*
Ahn et al (Nature Genetics, 3(4):283–291).*
Cawthon et al (Genomics, 9(3):446–460).*
Freshney (Culture of Animal Cells, A Manual of Basic Technique, Alan R. Liss, Inc., 1983, New York, p. 4).*
Dermer (Bio/Technology, 1994, 12:320).*
Bowie et al (Science, 1990, 247:1306–131).*
Burgess et al (J Cell Bio., 1990, 111:2129–2138).*
Cifone et al., Proc. Nat. Acad. Sci. USA. 77:1039–43 (1980).
Li et al., J. Nat. Can. Inst., 81:1406–12 (1989).
Simone et al., Blood, 98:201–209 (2001).
Wang et al., Proc. Natl. Acad. Sci., 94:12999–13004 (1997).
Zhu et al., Endocrinology, 139:4337–4344 (1998).
Accession No.: AK016628, released Feb. 8, 2001.
Accession No.: AF272973, released May 21, 2001.

* cited by examiner

*Primary Examiner*—Susan Ungar
(74) *Attorney, Agent, or Firm*—Klauber & Jackson

(57) ABSTRACT

The present invention discloses methods of distinguishing aggressive forms of prostate cancer from non-aggressive forms. In particular, two proteins that are specifically down-regulated in aggressive prostate cancer cells have been identified. One of the proteins is a novel transcription factor that is specifically involved in the apoptosis of cancer cells. The nucleic acid and amino acid sequences of the novel transcription factor is also disclosed.

10 Claims, 24 Drawing Sheets

PC3

Mock

Crt59

Crt35

Anchor PCR cloning procedure

MNGPAGLAYLDRRERILKLGESFEKQPRCAFHTVRYDF
KPASVDASCEGNLEVGKGEQVTITLPNIEGSTPPVTVFK
GSKRPYLKECILIINHDTGECRLEKLSSNITVKKTRGEGS
SKIQCRLEQQQQQMWNPPRTSNLVQHSPSEDKLSPTS
LMDDIERELKAEASLMDQMSSCDSSSDSRSSSSSSE
DSSSDSEDDDRSSPSGPRRYSSEHPSVSAGPQYRTSD
ADTTCNRLYDNSALLMSTLRSDLQLSESDSDSED (TID-1/PC3)

FIG. 9D M2
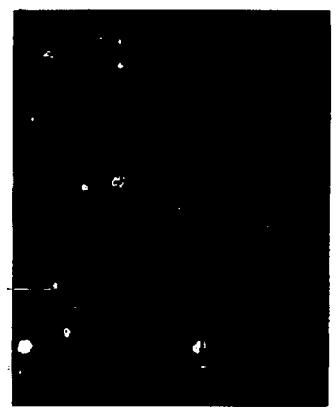
FIG. 9G 44
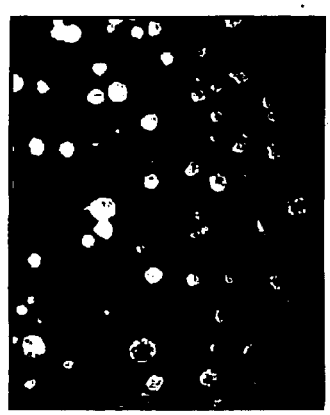
FIG. 9C M1
FIG. 9F 41
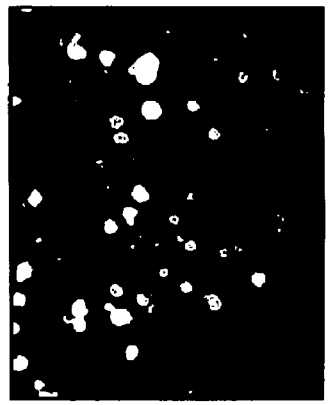
FIG. 9B PC3
FIG. 9E 27

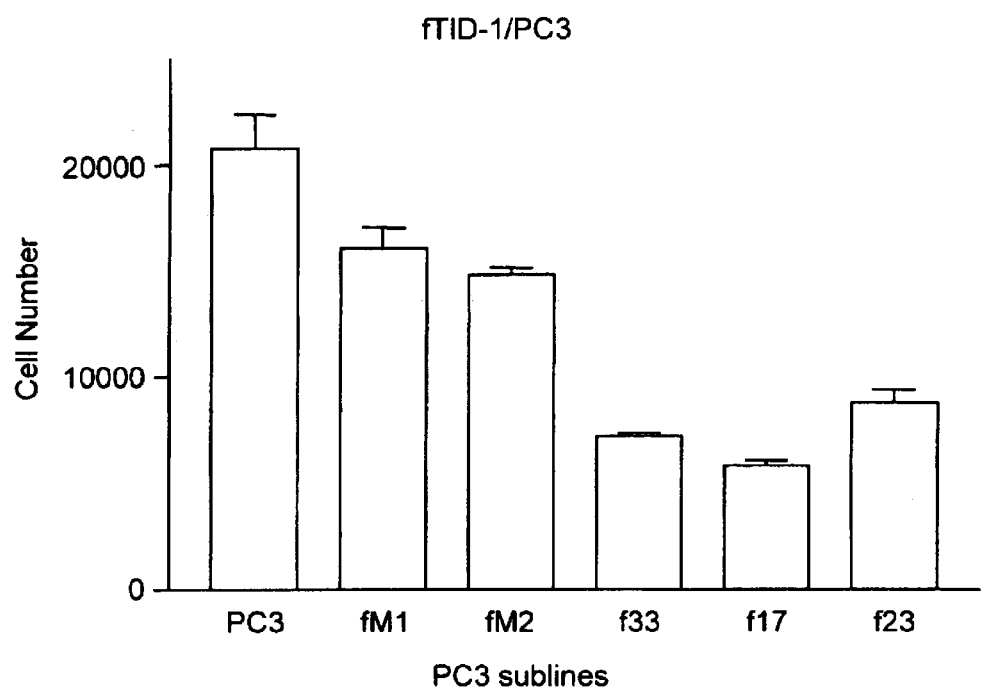

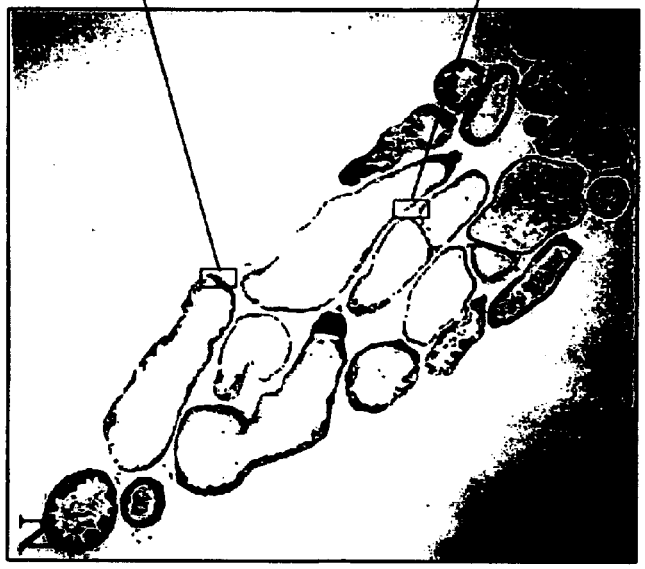

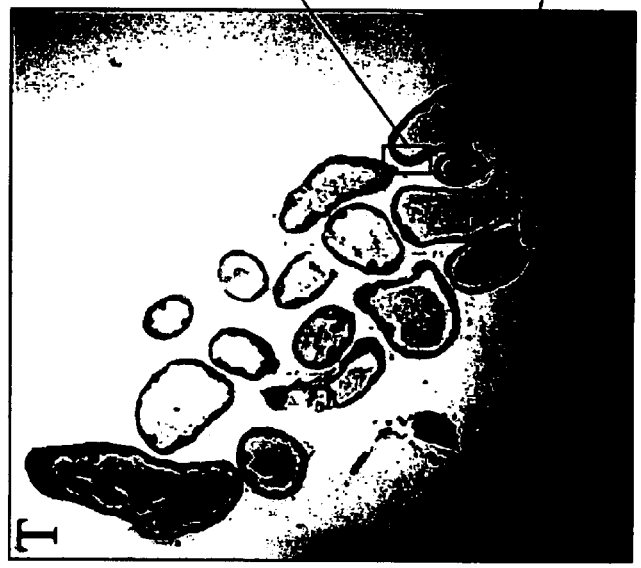

FIG. 14A

```
hTRAITS    1  MNSAAGFSHLDRRERVLKLGESFEKQPRCAFHTVRYDFKPASIDTSSEGY
mTRAITS    1  MSGPAGLAYLDRRERVLKLGESFEKQPRCAFHTVRYDFKPASIDTSCEGN
rTRAITS    1  MNGPAGLAYLDRRERILKLGESFEKQPRCAFHTVRYDFKPASVDASCEGN hTRAITS   51  LEVGEGEQVTITLPNIEGSTPPVTVFKGSKKPYLKECILIINHDTGECRL
mTRAITS   51  LEVGKGEQVTITLPNIEGSTPPVTVFKGSKRPYLKECILIINHDTGECRL
rTRAITS   51  LEVGKGEQVTITLPNIEGSTPPVTVFKGSKRPYLKECILIINHDTGECRL hTRAITS  101  EKLSSNITVKKTRVEGSSKIQYRKEQQQQQMWNSARTPNLVKHSPSEDKM
mTRAITS  101  EKLSSNITVKKTRVEGSSRIQYRLEQQQQQMWNLPRTSNLVQHSPSEEKM
rTRAITS  101  EKLSSNITVKKTRGEGSSKIQCRLEQQQQQMWNPPRTSNLVQHSPSEDKL hTRAITS  151  SPASPIDDIERELKAEASLMDQMSSCDSSSDSKSSSSSSSEDSSSSDSEDE
mTRAITS  151  SPTSLMDDIERELKAEASLMDQMSSCDSSSDSKSSSSSSSSEDSSSSDSEDD
rTRAITS  151  SPTSLMDDIERELKAEASLMDQMSSCDSSSDSRSSSSSSSSEDSSSSDSEDD hTRAITS  201  DCKSSTSDTGNCVSGHPTMT---QYRIPDIDASHNRFRDNSGLLMNTLRN
mTRAITS  201  D-QFSPLGPRKYSSEHPSMSAGPQYRTSEADATCHRLQDHSTLLMSTLRS
rTRAITS  201  D-RSSPSGPRRYSSEHPSVSAGPQYRTSDADTTCNRLYDNSALLMSTLRS hTRAITS  248  DLQLSESGSDSDD
mTRAITS  250  DLQLSESESDSED
rTRAITS  250  DLQLSESDSDSED
```

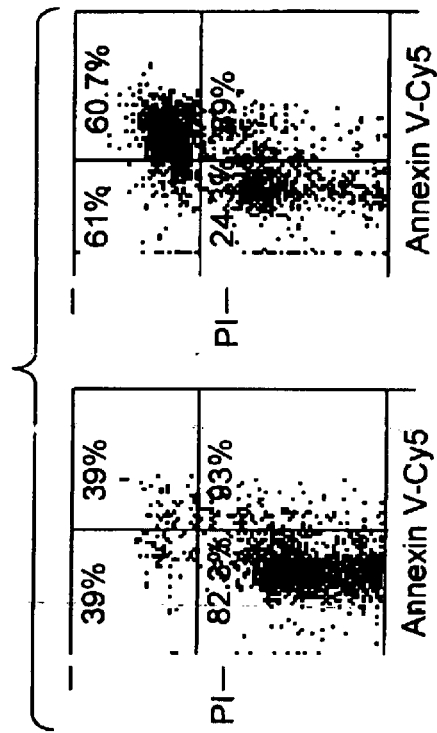
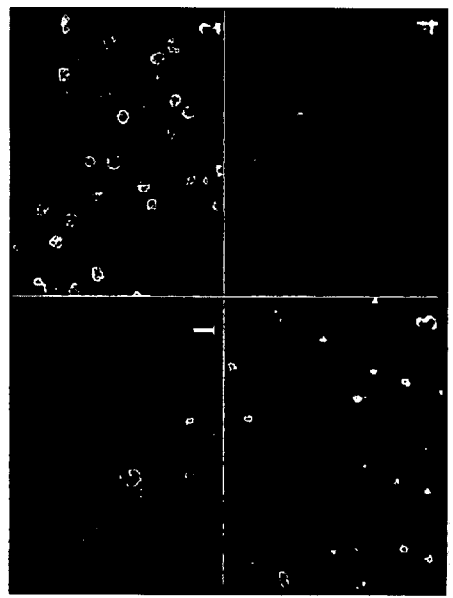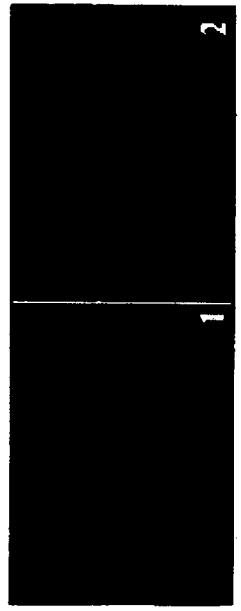
FIG. 16B
FIG. 16A
FIG. 16C

SEQUENCE LISTING

<160> NUMBER OF SEQ ID NOS: 36

<210> SEQ ID NO 1
<211> LENGTH: 4
<212> TYPE: PRT
<213> ORGANISM: Mus musculus

<400> SEQUENCE: 1

Lys Asp Glu Leu
1

```
<210> SEQ ID NO 2
<211> LENGTH: 17
<212> TYPE: PRT
<213> ORGANISM: Mus musculus
<220> FEATURE:
<221> NAME/KEY: MISC_FEATURE
<222> LOCATION: (2)..(3)
<223> OTHER INFORMATION: Xaa is any amino acid
<221> NAME/KEY: MISC_FEATURE
<222> LOCATION: (5)..(5)
<223> OTHER INFORMATION: Xaa is any amino acid
<221> NAME/KEY: MISC_FEATURE
<222> LOCATION: (10)..(10)
<223> OTHER INFORMATION: Xaa is any amino acid

<400> SEQUENCE: 2

Pro Xaa Xaa Ile Xaa Asp Pro Asp Ala Xaa Lys Pro Glu Asp Trp Asp
 1               5                  10                  15

Glu

<210> SEQ ID NO 3
<211> LENGTH: 14
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: Xaa is any amino acid
<221> NAME/KEY: MISC_FEATURE
<222> LOCATION: (4)..(4)
<223> OTHER INFORMATION: Xaa is any amino acid
<221> NAME/KEY: MISC_FEATURE
<222> LOCATION: (7)..(7)
<223> OTHER INFORMATION: Xaa is any amino acid
<221> NAME/KEY: MISC_FEATURE
<222> LOCATION: (9)..(9)
<223> OTHER INFORMATION: Xaa is any amino acid
<221> NAME/KEY: MISC_FEATURE
<222> LOCATION: (12)..(12)
<223> OTHER INFORMATION: Xaa is any amino acid
<221> NAME/KEY: MISC_FEATURE
<222> LOCATION: (14)..(14)
<223> OTHER INFORMATION: Xaa is any amino acid

<400> SEQUENCE: 3

Gly Xaa Trp Xaa Pro Pro Xaa Ile Xaa Asn Pro Xaa Tyr Xaa
 1               5                  10

<210> SEQ ID NO 4
<211> LENGTH: 9
<212> TYPE: PRT
<213> ORGANISM: Artificial sequence
<220> FEATURE:
<223> OTHER INFORMATION: HA Tag

<400> SEQUENCE: 4

Tyr Pro Tyr Asp Val Pro Asp Tyr Ala
 1               5

<210> SEQ ID NO 5
<211> LENGTH: 11
<212> TYPE: PRT
<213> ORGANISM: homo sapiens

<400> SEQUENCE: 5

Cys Gly Gly Gly Tyr Val Lys Leu Phe Pro Gly
 1               5                  10

<210> SEQ ID NO 6
```

```
<211> LENGTH: 12
<212> TYPE: PRT
<213> ORGANISM: homo sapiens

<400> SEQUENCE: 6

Ile Asn Lys Asp Ile Arg Cys Lys Asp Asp Glu Phe
1               5                   10

<210> SEQ ID NO 7
<211> LENGTH: 11
<212> TYPE: PRT
<213> ORGANISM: homo sapiens

<400> SEQUENCE: 7

Pro Asp Ala Ala Lys Pro Glu Asp Trp Asp Glu
1               5                   10

<210> SEQ ID NO 8
<211> LENGTH: 11
<212> TYPE: PRT
<213> ORGANISM: homo sapiens

<400> SEQUENCE: 8

Pro Thr Asp Ser Lys Pro Glu Asp Trp Asp Lys
1               5                   10

<210> SEQ ID NO 9
<211> LENGTH: 11
<212> TYPE: PRT
<213> ORGANISM: Homo sapiens

<400> SEQUENCE: 9

Pro Asp Ala Lys Lys Pro Glu Asp Trp Asp Glu
1               5                   10

<210> SEQ ID NO 10
<211> LENGTH: 13
<212> TYPE: PRT
<213> ORGANISM: Homo sapiens

<400> SEQUENCE: 10

Gly Glu Trp Glu Pro Pro Val Ile Gln Asn Pro Glu Tyr
1               5                   10

<210> SEQ ID NO 11
<211> LENGTH: 13
<212> TYPE: PRT
<213> ORGANISM: Homo sapiens

<400> SEQUENCE: 11

Gly Glu Trp Lys Pro Arg Gln Ile Asp Asn Pro Asp Tyr
1               5                   10

<210> SEQ ID NO 12
<211> LENGTH: 13
<212> TYPE: PRT
<213> ORGANISM: Homo sapiens

<400> SEQUENCE: 12

Gly Thr Trp Ile His Pro Glu Ile Asp Asn Pro Glu Tyr
1               5                   10

<210> SEQ ID NO 13
<211> LENGTH: 1132
<212> TYPE: DNA
```

<213> ORGANISM: Rattus norvegicus

<400> SEQUENCE: 13

```
gcacgcgtct ggagagagat gaacggagcc cgccccggtt ccgagctcag gctcgcggcc      60
agtgcaagct actccagaag gctgcggcgg cgggacagtg aaggcgaagc gggaggcaga     120
ggaagaggat gaatggacca gcgggactcg cataccctcga ccgtcgcgag cggattctca    180
aattaggcga aagtttcgag aagcagccgc gctgtgcttt ccacaccgtg cgctatgact     240
tcaaacctgc ttctgttgat gcctcttgtg aaggaaatct tgaggttggc aaaggtgaac    300
aggtgacaat aactcttcca aatatagaag gttcaactcc accagtcaca gttttcaaag    360
gttccaagag accttactta aaagagtgca ttttgattat taaccatgat actggggaat    420
gtcgcctaga aaaactcagc agcaacatca ctgtgaaaaa acaagagga gaaggaagta    480
gcaaaatcca gtgcagacta gaacaacagc aacaacaaat gtggaatcca cccaggacat    540
ccaaccttgt acagcattct ccatcagaag ataagctgtc cccaacgtct ctaatggatg    600
atattgaaag agagctgaag gcggaagcta gtcttatgga ccagatgagt agttgtgata    660
gttcatccga ttccagaagt tcttcatctt caagtagtga ggacagttct agtgattccg    720
aagatgatga ccgatcctct ccttccggtc aaggaggta cagctcagag caccccagcg    780
tatctgctgg gccacagtac aggacttcag atgctgacac tacttgtaac agactttacg    840
acaacagtgc ccttctgatg agtactttac gaagtgatct gcagctgagt gagtcagaca    900
gcgacagtga ggactgaagc aatatcaagc cataaggaaa acacttgctg caaagcttct    960
agggaagctt ggggggaaaa aagaaaaga aaacatttgt aagatgtttg agaatctgtt   1020
ttgtattgag aataaatatt cctatgttca ttgaaaatat gcaacttttg ctgataaaat  1080
aaagttggtt cagggttttc aactcttaaa aaaaaaaaa aaaaaaaaa aa            1132
```

<210> SEQ ID NO 14
<211> LENGTH: 262
<212> TYPE: PRT
<213> ORGANISM: Rattus norvegicus

<400> SEQUENCE: 14

```
Met Asn Gly Pro Ala Gly Leu Ala Tyr Leu Asp Arg Arg Glu Arg Ile
1               5                   10                  15

Leu Lys Leu Gly Glu Ser Phe Glu Lys Gln Pro Arg Cys Ala Phe His
            20                  25                  30

Thr Val Arg Tyr Asp Phe Lys Pro Ala Ser Val Asp Ala Ser Cys Glu
        35                  40                  45

Gly Asn Leu Glu Val Gly Lys Gly Glu Gln Val Thr Ile Thr Leu Pro
    50                  55                  60

Asn Ile Glu Gly Ser Thr Pro Pro Val Thr Val Phe Lys Gly Ser Lys
65                  70                  75                  80

Arg Pro Tyr Leu Lys Glu Cys Ile Leu Ile Ile Asn His Asp Thr Gly
                85                  90                  95

Glu Cys Arg Leu Glu Lys Leu Ser Ser Asn Ile Thr Val Lys Lys Thr
            100                 105                 110

Arg Gly Glu Gly Ser Ser Lys Ile Gln Cys Arg Leu Glu Gln Gln Gln
        115                 120                 125

Gln Gln Met Trp Asn Pro Pro Arg Thr Ser Asn Leu Val Gln His Ser
    130                 135                 140

Pro Ser Glu Asp Lys Leu Ser Pro Thr Ser Leu Met Asp Asp Ile Glu
145                 150                 155                 160
```

Arg Glu Leu Lys Ala Glu Ala Ser Leu Met Asp Gln Met Ser Ser Cys
            165                 170                 175

Asp Ser Ser Asp Ser Arg Ser Ser Ser Ser Ser Glu Asp
            180                 185                 190

Ser Ser Ser Asp Ser Glu Asp Asp Arg Ser Ser Pro Ser Gly Pro
            195                 200                 205

Arg Arg Tyr Ser Ser Glu His Pro Ser Val Ser Ala Gly Pro Gln Tyr
        210                 215                 220

Arg Thr Ser Asp Ala Asp Thr Thr Cys Asn Arg Leu Tyr Asp Asn Ser
225                 230                 235                 240

Ala Leu Leu Met Ser Thr Leu Arg Ser Asp Leu Gln Leu Ser Glu Ser
            245                 250                 255

Asp Ser Asp Ser Glu Asp
            260

<210> SEQ ID NO 15
<211> LENGTH: 996
<212> TYPE: DNA
<213> ORGANISM: Mus musculus

<400> SEQUENCE: 15
gctgtggcag gggacggcga aggccaaaag cgggaggcag gggacgagga tgagtggacc        60
agcgggactt gcatacctgg accgtcgcga gcgggttctc aagctaggcg aaagtttcga       120
gaagcagccg cgctgtgcct ccacaccgt gcgctatgac ttcaaacctg cttctattga       180
tacttcttgt gaaggaaatc ttgaggttgg caaaggtgaa caggtgacaa taactcttcc       240
aaatatagaa ggttcaactc caccagtcac agttttcaaa ggttccaaga gaccttactt       300
aaaagaatgc attttgatta ttaaccatga tactgggaa tgtcgcctag aaaagctcag       360
cagcaacatc actgtgaaaa aacaagagt ggaagggagt agcagaatcc agtacagact       420
agaacaacag caacagcaaa tgtggaatct gcctaggact tccaatcttg tacagcattc       480
tccatcagaa gagaagatgt ctccaacgtc tctaatggat gatattgaaa gagaactgaa       540
agcagaagct agtcttatgg accagatgag tagttgtgat agttcatcag attccaaaag       600
ttcttcatct tcaagtagtg aggatagttc tagtgattct gaagatgatg accaattctc       660
tcctttgggt ccaaggaaat acagctcgga gcaccctagc atgtctgctg gccacagta       720
caggacttca gaggctgatg ctacttgtca ccgacttcag gaccacagta cccttctgat       780
gagtacttta cgaagtgact tgcagctgag tgagtcagaa agcgacagtg aggactgaag       840
cagtatcaag ctacagagaa acatttgtg agatgtgtaa gaatctgttt tgtattgaga       900
ataaatattc ctatgtttat ggaaattgtg caacttttgc tgaaaaaata agttggttc       960
agaattttca actaaaaaaa aaaaaaaaaa aaaaaa                                 996

<210> SEQ ID NO 16
<211> LENGTH: 262
<212> TYPE: PRT
<213> ORGANISM: Mus musculus

<400> SEQUENCE: 16

Met Ser Gly Pro Ala Gly Leu Ala Tyr Leu Asp Arg Arg Glu Arg Val
1               5                   10                  15

Leu Lys Leu Gly Glu Ser Phe Glu Lys Gln Pro Arg Cys Ala Phe His
            20                  25                  30

Thr Val Arg Tyr Asp Phe Lys Pro Ala Ser Ile Asp Thr Ser Cys Glu

```
              35                  40                  45
Gly Asn Leu Glu Val Gly Lys Gly Glu Gln Val Thr Ile Thr Leu Pro
    50                  55                  60

Asn Ile Glu Gly Ser Thr Pro Pro Val Thr Val Phe Lys Gly Ser Lys
65                  70                  75                  80

Arg Pro Tyr Leu Lys Glu Cys Ile Leu Ile Ile Asn His Asp Thr Gly
                85                  90                  95

Glu Cys Arg Leu Glu Lys Leu Ser Ser Asn Ile Thr Val Lys Lys Thr
            100                 105                 110

Arg Val Glu Gly Ser Ser Arg Ile Gln Tyr Arg Leu Glu Gln Gln Gln
        115                 120                 125

Gln Gln Met Trp Asn Leu Pro Arg Thr Ser Asn Leu Val Gln His Ser
    130                 135                 140

Pro Ser Glu Glu Lys Met Ser Pro Thr Ser Leu Met Asp Asp Ile Glu
145                 150                 155                 160

Arg Glu Leu Lys Ala Glu Ala Ser Leu Met Asp Gln Met Ser Ser Cys
                165                 170                 175

Asp Ser Ser Ser Asp Ser Lys Ser Ser Ser Ser Ser Ser Ser Glu Asp
            180                 185                 190

Ser Ser Ser Asp Ser Glu Asp Asp Gln Phe Ser Pro Leu Gly Pro
        195                 200                 205

Arg Lys Tyr Ser Ser Glu His Pro Ser Met Ser Ala Gly Pro Gln Tyr
    210                 215                 220

Arg Thr Ser Glu Ala Asp Ala Thr Cys His Arg Leu Gln Asp His Ser
225                 230                 235                 240

Thr Leu Leu Met Ser Thr Leu Arg Ser Asp Leu Gln Leu Ser Glu Ser
                245                 250                 255

Glu Ser Asp Ser Glu Asp
            260

<210> SEQ ID NO 17
<211> LENGTH: 1008
<212> TYPE: DNA
<213> ORGANISM: Homo sapiens

<400> SEQUENCE: 17
aagctgcttc aggctgaggg ggcagatagt gagcgctggt ggcggagtta aagtcaaagc      60
aggagagtaa ttatgaatag cgcagcggga ttctcacacc tagaccgtcg cgagcgggtt     120
ctcaagttag gggagagttt cgagaagcag ccgcgctgcg ccttccacac tgtgcgctat     180
gacttcaaac ctgcttctat tgacacttct tctgaaggat accttgaggt tggtgaaggt     240
gaacaggtga ccataactct gccaaatata gaaggttcaa ctccaccagt aactgttttc     300
aaaggttcaa aaaaccctta cttaaaagaa tgcattttga ttattaacca tgatactgga     360
gaatgtcggc tagaaaaact cagcagcaac atcactgtaa aaaaaacaag agttgaagga     420
agcagtaaaa ttcagtatcg taagaacaa cagcaacaac aaatgtggaa ttcagccagg     480
actcccaatc ttgtaaaaca ttctccatct gaagataaga tgtccccagc atctccaata     540
gatgatatcg aaagagaact gaaggcagaa gctagtctaa tggaccagat gagtagttgt     600
gatagttcat cagattccaa agttcatca tcttcaagta gtgaggatag ttctagtgac     660
tcagaagatg aagattgcaa atcctctact tctgatacag ggaattgtgt ctcaggacat     720
cctaccatga cacagtacag gattcctgat atagatgcca gtcataatag atttcgagac     780
aacagtggcc ttctgatgaa tacttttaaga aatgatttgc agctgagtga atcaggaagt     840
```

```
gacagtgatg actgaagaaa tatttagcta taaataaaaa tttatacagc atgtataatt      900
tattttgtat taacaataaa aattcctaag actgagggaa atatgtctta acttttgatg      960
ataaaagaaa ttaaatttga ttcagaaatt tcaaaaaaaa aaaaaaaa                  1008
```

<210> SEQ ID NO 18
<211> LENGTH: 260
<212> TYPE: PRT
<213> ORGANISM: Homo sapiens

<400> SEQUENCE: 18

```
Met Asn Ser Ala Ala Gly Phe Ser His Leu Asp Arg Arg Glu Arg Val
1               5                   10                  15

Leu Lys Leu Gly Glu Ser Phe Glu Lys Gln Pro Arg Cys Ala Phe His
            20                  25                  30

Thr Val Arg Tyr Asp Phe Lys Pro Ala Ser Ile Asp Thr Ser Ser Glu
        35                  40                  45

Gly Tyr Leu Glu Val Gly Gly Glu Gln Val Thr Ile Thr Leu Pro
    50                  55                  60

Asn Ile Glu Gly Ser Thr Pro Pro Val Thr Val Phe Lys Gly Ser Lys
65                  70                  75                  80

Lys Pro Tyr Leu Lys Glu Cys Ile Leu Ile Asn His Asp Thr Gly
                85                  90                  95

Glu Cys Arg Leu Glu Lys Leu Ser Ser Asn Ile Thr Val Lys Lys Thr
            100                 105                 110

Arg Val Glu Gly Ser Ser Lys Ile Gln Tyr Arg Lys Glu Gln Gln Gln
        115                 120                 125

Gln Gln Met Trp Asn Ser Ala Arg Thr Pro Asn Leu Val Lys His Ser
    130                 135                 140

Pro Ser Glu Asp Lys Met Ser Pro Ala Ser Pro Ile Asp Asp Ile Glu
145                 150                 155                 160

Arg Glu Leu Lys Ala Glu Ala Ser Leu Met Asp Gln Met Ser Ser Cys
                165                 170                 175

Asp Ser Ser Ser Asp Ser Lys Ser Ser Ser Ser Ser Ser Glu Asp
            180                 185                 190

Ser Ser Ser Asp Ser Glu Asp Glu Asp Cys Lys Ser Ser Thr Ser Asp
        195                 200                 205

Thr Gly Asn Cys Val Ser Gly His Pro Thr Met Thr Gln Tyr Arg Ile
    210                 215                 220

Pro Asp Ile Asp Ala Ser His Asn Arg Phe Arg Asp Asn Ser Gly Leu
225                 230                 235                 240

Leu Met Asn Thr Leu Arg Asn Asp Leu Gln Leu Ser Glu Ser Gly Ser
                245                 250                 255

Asp Ser Asp Asp
            260
```

<210> SEQ ID NO 19
<211> LENGTH: 989
<212> TYPE: DNA
<213> ORGANISM: Homo sapiens

<400> SEQUENCE: 19

```
cttgcttctg gacccgggtg ggtgccggct cggctctcct tgtcttccag agcggtggcc       60
cggaagcaca gtcctcccag acgccagcgc cagaagctcg gatcgcggct gcaccgggag      120
agcgccgatc tgggtgcgag gcaggtgcgg ggccatgaat gggaccgcaa acccgctgct      180
```

-continued

```
ggaccgcgag gaacattgcc tgaggctcgg ggagagcttc gagaagcggc cgcgggcctc      240
cttccacact attcgttatg attttaaacc agcatctata gacacttcct gtgaaggaga      300
gcttcaagtt ggcaaaggag atgaagtcac aattacactg ccacatatcc ctggatccac      360
accacccatg actgtgttca aggggaacaa acggcttac cagaaagact gtgtgcttat       420
tattaatcat gacactggtg aatatgtgct ggaaaaactc agtagcagca ttcaggtgaa      480
gaaaacaaga gctgagggca gcagtaaaat ccaggcccga atggaacagc agcccactcg      540
tcctccacag acgtcacagc caccaccacc tccaccacct atgccattca gagctccaac      600
gaagcctcca gttggaccca aaacttctcc cttgaaagat aacccgtcac ctgaacctca      660
gttggatgac atcaaaagag agctgagggc tgaagttgac attattgaac aaatgagcag      720
cagcagtggg agcagctctt cagactctga gagctcttcg ggaagtgatg acgatagctc      780
cagcagtgga ggcgaggaca atggcccagc ctctcctccg cagccttcac accagcagcc      840
ctacaacagt aggcctgccg ttgccaatgg aaccagccgg ccacaaggaa gcaaccagct      900
catgaacacc ctcagaaatg acttgcagtt gagtgagtct ggcagtgaca gtgatgacta      960
gtgctggatc tttcgaaacc tacttttg                                        989
```

<210> SEQ ID NO 20
<211> LENGTH: 268
<212> TYPE: PRT
<213> ORGANISM: Homo sapiens

<400> SEQUENCE: 20

```
Met Asn Gly Thr Ala Asn Pro Leu Leu Asp Arg Glu Glu His Cys Leu
1               5                   10                  15

Arg Leu Gly Glu Ser Phe Glu Lys Arg Pro Arg Ala Ser Phe His Thr
            20                  25                  30

Ile Arg Tyr Asp Phe Lys Pro Ala Ser Ile Asp Thr Ser Cys Glu Gly
        35                  40                  45

Glu Leu Gln Val Gly Lys Gly Asp Glu Val Thr Ile Thr Leu Pro His
    50                  55                  60

Ile Pro Gly Ser Thr Pro Met Thr Val Phe Lys Gly Asn Lys Arg
65                  70                  75                  80

Pro Tyr Gln Lys Asp Cys Val Leu Ile Ile Asn His Asp Thr Gly Glu
                85                  90                  95

Tyr Val Leu Glu Lys Leu Ser Ser Ile Gln Val Lys Lys Thr Arg
            100                 105                 110

Ala Glu Gly Ser Ser Lys Ile Gln Ala Arg Met Glu Gln Gln Pro Thr
        115                 120                 125

Arg Pro Pro Gln Thr Ser Gln Pro Pro Pro Pro Pro Met Pro
    130                 135                 140

Phe Arg Ala Pro Thr Lys Pro Val Gly Pro Lys Thr Ser Pro Leu
145                 150                 155                 160

Lys Asp Asn Pro Ser Pro Glu Pro Gln Leu Asp Ile Lys Arg Glu
                165                 170                 175

Leu Arg Ala Glu Val Asp Ile Ile Glu Gln Met Ser Ser Ser Gly
            180                 185                 190

Ser Ser Ser Asp Ser Glu Ser Ser Gly Ser Asp Asp Ser
        195                 200                 205

Ser Ser Gly Gly Glu Asp Asn Gly Pro Ala Ser Pro Gln Pro
    210                 215                 220
```

-continued

Ser His Gln Gln Pro Tyr Asn Ser Arg Pro Ala Val Ala Asn Gly Thr
225                 230                 235                 240

Ser Arg Pro Gln Gly Ser Asn Gln Leu Met Asn Thr Leu Arg Asn Asp
            245                 250                 255

Leu Gln Leu Ser Glu Ser Gly Ser Asp Ser Asp
        260                 265

<210> SEQ ID NO 21
<211> LENGTH: 21
<212> TYPE: DNA
<213> ORGANISM: Artificial sequence
<220> FEATURE:
<223> OTHER INFORMATION: primer

<400> SEQUENCE: 21
gttcaactcc accagtcaca g                                         21

<210> SEQ ID NO 22
<211> LENGTH: 20
<212> TYPE: DNA
<213> ORGANISM: Artificial sequence
<220> FEATURE:
<223> OTHER INFORMATION: primer

<400> SEQUENCE: 22
cggtgacaag tagcatcagc                                            20

<210> SEQ ID NO 23
<211> LENGTH: 20
<212> TYPE: DNA
<213> ORGANISM: Artificial sequence
<220> FEATURE:
<223> OTHER INFORMATION: primer

<400> SEQUENCE: 23
ctgaagtcct gtactgtggc                                            20

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
cacaactact catctggtcc                                            20

<210> SEQ ID NO 25
<211> LENGTH: 20
<212> TYPE: DNA
<213> ORGANISM: Artificial sequence
<220> FEATURE:
<223> OTHER INFORMATION: primer

<400> SEQUENCE: 25
tgatactgga ggatgtcggc                                            20

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26

```
cacaactact catctggtcc                                              20
```

<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27

```
gctggggaca tcttatcttc                                              20
```

<210> SEQ ID NO 28
<211> LENGTH: 20
<212> TYPE: DNA
<213> ORGANISM: Artificial sequence
<220> FEATURE:
<223> OTHER INFORMATION: primer

<400> SEQUENCE: 28

```
cagtgattgt tgctgctgag                                              20
```

<210> SEQ ID NO 29
<211> LENGTH: 20
<212> TYPE: DNA
<213> ORGANISM: Artificial sequence
<220> FEATURE:
<223> OTHER INFORMATION: primer

<400> SEQUENCE: 29

```
ctcagcagca acatcactgt                                              20
```

<210> SEQ ID NO 30
<211> LENGTH: 20
<212> TYPE: DNA
<213> ORGANISM: Artificial sequence
<220> FEATURE:
<223> OTHER INFORMATION: primer

<400> SEQUENCE: 30

```
gtctgtctgg atccgaggtg                                              20
```

<210> SEQ ID NO 31
<211> LENGTH: 20
<212> TYPE: DNA
<213> ORGANISM: Artificial sequence
<220> FEATURE:
<223> OTHER INFORMATION: primer

<400> SEQUENCE: 31

```
cgcgacgtaa gcttcggaag                                              20
```

<210> SEQ ID NO 32
<211> LENGTH: 60
<212> TYPE: DNA
<213> ORGANISM: Artificial sequence
<220> FEATURE:
<221> NAME/KEY: misc_feature
<222> LOCATION: (25)..(36)
<223> OTHER INFORMATION: n is any nucleotide

<400> SEQUENCE: 32

```
gtctgtctgg atccgaggtg agtannnnnn nnnnnnacgt cttccgaagc ttacgtcgcg   60
```

<210> SEQ ID NO 33
<211> LENGTH: 60

<212> TYPE: DNA
<213> ORGANISM: Artificial sequence
<220> FEATURE:
<223> OTHER INFORMATION: primer

<400> SEQUENCE: 33

| | | | | | |
|---|---|---|---|---|---|
| gtctgtctgg | atccgaggtg | agtactgact | ttacacacgt | cttccgaagc | ttacgtcgcg | 60 |

<210> SEQ ID NO 34
<211> LENGTH: 60
<212> TYPE: DNA
<213> ORGANISM: Artificial sequence
<220> FEATURE:
<223> OTHER INFORMATION: primer

<400> SEQUENCE: 34

| | | | | | |
|---|---|---|---|---|---|
| gtctgtctgg | atccgaggtg | agtactgacg | ttacacacgt | cttccgaagc | ttacgtcgcg | 60 |

<210> SEQ ID NO 35
<211> LENGTH: 1920
<212> TYPE: DNA
<213> ORGANISM: Homo sapiens

<400> SEQUENCE: 35

| | | | | | |
|---|---|---|---|---|---|
| gcacgagggc | agagccgctg | ccggagggtc | gttttaaagg | gcccgcgcgt | tgccgccccc | 60 |
| tcggcccgcc | atgctgctat | ccgtgccgct | gctgctcggc | ctcctcggcc | tggccgtcgc | 120 |
| cgagcctgcc | gtctacttca | aggagcagtt | tctggacgga | gacgggtgga | cttcccgctg | 180 |
| gatcgaatcc | aaacacaagt | cagattttgg | caaattcgtt | ctcagttccg | gcaagttcta | 240 |
| cggtgacgag | gagaaagata | aggtttgca | gacaagccag | gatgcacgct | tttatgctct | 300 |
| gtcggccagt | ttcgagcctt | tcagcaacaa | aggccgacg | ctggtggtgc | agttcacggt | 360 |
| gaaacatgag | cagaacatcg | actgtggggg | cggctatgtg | aagctgtttc | ctaatagttt | 420 |
| ggaccagaca | gacatgcacg | gagactcaga | atacaacatc | atgtttggtc | ccgacatctg | 480 |
| tggccctggc | accaagaagg | ttcatgtcat | cttcaactac | aagggcaaga | acgtgctgat | 540 |
| caacaaggac | atccgttgca | aggatgatga | gtttacacac | ctgtacacac | tgattgtgcg | 600 |
| gccagacaac | acctatgagg | tgaagattga | caacagccag | gtggagtccg | gctccttgga | 660 |
| agacgattgg | gacttcctgc | cacccaagaa | gataaaggat | cctgatgctt | caaaaccgga | 720 |
| agactgggat | gagcgggcca | gatcgatga | tcccacagac | tccaagcctg | aggactggga | 780 |
| caagcccgag | catatccctg | accctgatgc | taagaagccc | gaggactggg | atgaagagat | 840 |
| ggacggagag | tgggaacccc | cagtgattca | gaaccctgag | tacaagggtg | agtggaagcc | 900 |
| ccggcagatc | gacaacccag | attacaaggg | cacttggatc | cacccagaaa | ttgacaaccc | 960 |
| cgagtattct | cccgatccca | gtatctatgc | ctatgataac | tttggcgtgc | tgggcctgga | 1020 |
| cctctggcag | gtcaagtctg | gcaccatctt | tgacaacttc | ctcatcacca | acgatgaggc | 1080 |
| atacgctgag | gagtttggca | acgagacgtg | ggcgtaaca | aaggcagcag | agaaacaaat | 1140 |
| gaaggacaaa | caggacgagg | agcagaggct | taaggaggag | gaagaagaca | agaaacgcaa | 1200 |
| agaggaggag | gaggcagagg | acaaggagga | tgatgaggac | aaagatgagg | atgaggagga | 1260 |
| tgaggaggac | aaggaggaag | atgaggagga | agatgtcccc | ggccaggcca | aggacgagct | 1320 |
| gtagagaggc | ctgcctccag | ggctggactg | aggcctgagc | gctcctgccg | cagagctggc | 1380 |
| cgcgccaaat | aatgtctctg | tgagactcga | gaactttcat | tttttttccag | gctggttcgg | 1440 |
| atttggggtg | gattttggtt | ttgttcccct | cctccactct | cccccacccc | ctccccgccc | 1500 |

-continued

```
tttttttttt tttttttttta aactggtatt ttatctttga ttctccttca gccctcaccc    1560
ctggttctca tctttcttga tcaacatctt ttcttgcctc tgtccccttc tctcatctct    1620
tagctcccct ccaacctggg gggcagtggt gtggagaagc cacaggcctg agatttcatc    1680
tgctctcctt cctggagccc agaggagggc agcagaaggg ggtggtgtct ccaaccccc    1740 agcactgagg aagaacgggg ctcttctcat ttcaccctc cctttctccc ctgcccccag    1800
gactgggcca cttctggtg gggcagtggg tcccagattg gctcacactg agaatgtaag    1860
aactacaaac aaaatttcta ttaaattaaa ttttgtgtct ccaaaaaaaa aaaaaaaaa    1920
```

<210> SEQ ID NO 36
<211> LENGTH: 417
<212> TYPE: PRT
<213> ORGANISM: Homo sapiens

<400> SEQUENCE: 36

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300
```

-continued

```
Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
            325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Glu Asp Lys Asp Glu Asp Glu Asp Glu Glu Asp
385                 390                 395                 400

Lys Glu Glu Asp Glu Glu Glu Asp Val Pro Gly Gln Ala Lys Asp Glu
                405                 410                 415

Leu
```

METHOD FOR PROGNOSING CANCER AND THE PROTEINS INVOLVED

CROSS-REFERENCE TO RELATED APPLICATIONS

The present Application is a non-provisional application claiming the priority of copending provisional U.S. Ser. No. 60/218,761, filed Jul. 17, 2000 now abandoned, the disclosure of which is hereby incorporated by reference in its entirety. Applicants claim the benefits of this Application under 35 U.S.C. §119(e).

GOVERNMENTAL SUPPORT

The research leading to the present invention was supported, at least in part, by a grant from the National Institutes of Health, Grant No.R01 DK51193. Accordingly, the Government may have certain rights in the invention.

FIELD OF THE INVENTION

The present invention relates to particular marker proteins that can be used in the prognosis of prostate cancer. The present invention further relates to novel transcription factors that can effect apoptosis in cancerous cells. Methods of treating cancer cells, and prostate cancer cells are also provided. The nucleic acid and amino acid sequences of the novel transcription factors are provided along with probes, including nucleotide probes and antibodies, which can be used to determine the presence or absence of the novel transcription factor.

BACKGROUND OF THE INVENTION

It is generally acknowledged in the medical community that all men will eventually develop prostate cancer, provided that they live long enough for the condition to develop. For example, 50% of all men over 50, and essentially all men over 70 suffer from some form of prostate hyperplasia. Indeed, prostate cancer is the most frequently diagnosed cancer in the United States, with over a quarter of a million new cases being diagnosed each year. Despite the roughly $4 billion dollars per year spent treating this disease, forty thousand men die every year due to prostate cancer, which makes prostate cancer the second leading cause of cancer death in men.

Although the pathogenesis of prostate cancer has not been completely delineated, androgen is believed to play an important role in the development and progression of prostate cancer. It is well established that androgen-dependent growth of the normal prostate stops once the gland reaches the normal size. Indeed, androgen controls the homeostasis of the normal prostate through the androgen action pathway, a cascade of molecular and cellular events triggered by androgen leading to cell growth, differentiation, and/or death. In addition, programmed cell death (i.e., apoptosis) is triggered in the prostate when testosterone levels are completely depleted, and the prostate undergoes regression. Thus, castrated mammals have been employed as an experimental animal model for studying prostate cancer and cDNA collections enriched in genes regulated in prostate homeostasis, and prostrate regression have been disclosed [U.S. Pat. No. 5,821,352, Issued Oct. 13, 1998; and U.S. Pat. No. 5,928,871, Issued Jul. 27, 1999, the contents of which are hereby incorporated by reference in their entireties].

As alluded to above, one characteristic of prostate cancer is that it generally arises relatively late in life and then progresses slowly. If this were always true, the optimal medical response would be to simply monitor the progression of the cancer rather than aggressively treating it, since by the time the cancer progressed to a life threatening stage, the patient would have likely expired due to other more rapidly progressing factors. However, prostate cancers are highly heterogeneous in their progression. Some cancers grow very rapidly and need to be treated aggressively, whereas others are very slow growing and not life-threatening. Thus, one of the most important considerations in the present day treatment of prostate cancer is distinguishing aggressive prostate cancers, which need aggressive treatment, from less aggressive ones, which only require monitoring.

Unfortunately, there are no prognostic tests that can distinguish aggressive prostate cancers from less aggressive forms of the disease. Currently, there is no effective way to distinguish aggressive prostate cancers from slow-growing prostate cancers. Indeed, the present technology relies on monitoring the protein PSA, which not only results in a high percentage of false positives, but also cannot be used as a predictor of the future progression of the disease.

Considering the severe side-effects and expense associated with treating cancer, and prostate cancer treatment in particular, better prognosis tools are desperately needed. Therefore, there is a need to identify other factors that are diagnostic of cancer, and prostate cancer in particular. Furthermore, there is a need to identify means that can be used to accurately predict the progression of cancer, such as prostate cancer. In addition, there is a need to identify means that can be used to identify individual stages of the progression of prostate regression. Furthermore, there is a need to identify factors that can be used in the treatment of cancer, and in particular, prostate cancer.

The citation of any reference herein should not be construed as an admission that such reference is available as "Prior Art" to the instant application.

SUMMARY OF THE INVENTION

The present invention therefore provides methods that allow aggressive forms of cancer to be identified. In one such embodiment, an aggressive form of prostate cancer is identified. Importantly, a specific protein, TID-1 (otherwise known as TRAITS) is shown to be down-regulated in aggressive forms of cancer. Such cancers include epithelium-derived carcinomas, kidney cancers, lymphomas, leukemias and particularly, prostate cancer.

A particular aspect of the present invention provides the identity of two proteins that are down-regulated in aggressive prostate cancer, but not in slowly progressing prostate cancers. As provided herein, the two prostate proteins, calreticulin and TID-1, are shown to play important roles in the part of the androgen action pathway that suppresses cell proliferation and/or prevents prostate cancer. Therefore the expression of calreticulin (e.g., human calreticulin having the amino acid sequence of SEQ ID NO:36, encoded by the nucleic acid sequence of SEQ ID NO:35) and TID-1 (e.g., human TID-1 having the amino acid sequence of SEQ ID NO:18, encoded by the nucleic acid sequence of SEQ ID NO:17) in prostate cancer cells can be used as markers to distinguish aggressive forms of prostate cancer, which require immediate treatment, from slow growing forms that need only to be monitored.

Although the present invention is not dependent on any particular model, as disclosed below, the present invention is consistent with the unexpected finding that part of the androgen action pathway acts to suppress cell proliferation.

This growth suppression is essential for prostate homeostasis and furthermore, limits the cell number in a healthy prostate. In contrast, the inactivation of the part of the androgen action pathway that acts to suppress cell proliferation results in uncontrolled growth leading to prostate cancer.

Therefore, the present invention provides methods of identifying an animal subject, preferably a human subject that is likely to have an aggressive form of prostate cancer. In one embodiment the likelihood determined is between 50 to 100%. In another embodiment the likelihood determined is greater than 70%. In a preferred embodiment, the method identifies an individual that has an 80% or more likelihood of having an aggressive form of prostate cancer. One such method comprises determining the level of calreticulin in a prostate sample from the animal subject. In one embodiment, the sample is obtained by radical prostatectomy. In another embodiment, the sample is obtained by needle biopsy.

When the level of calreticulin determined is 75% or more down-regulated in tumor cells relative to that determined in benign prostatic epithelial cells of the same specimen, the animal subject is identified as being likely to have an aggressive form of prostate cancer. In one embodiment the determination of the level of calreticulin is performed in situ. In another embodiment the determination of the level of calreticulin is performed in vitro. In still another embodiment, the determination of the level of calreticulin is performed in vivo. In a preferred embodiment, the determination of the level of calreticulin is performed by Laser Capture Microscopy coupled with a Western blot.

In a particular embodiment the determination of the level of calreticulin is performed with an antibody specific for calreticulin. In another such embodiment the determination of the level of calreticulin is performed by PCR with a primer specific for an mRNA encoding calreticulin. In still another embodiment the determination of the level of calreticulin is performed with a nucleotide probe specific for an mRNA encoding calreticulin. In one such embodiment, the determination of the level of calreticulin is performed by a Northern blot. In another embodiment, the determination of the level of calreticulin is performed by a ribonuclease protection assay.

In a related embodiment, the method further comprises detecting the TID-1 in a prostate sample from the animal subject. The TID-1 can be detected by Western blot and/or Northern blot and/or as provided for below. When the TID-1 is low to undetectable in the prostate sample, (e.g., undetectable being not detectable by a Western blot and/or Northern blot and/or immunohistochemistry) the subject is further confirmed as being likely to have an aggressive form of prostate cancer.

In yet another embodiment, the method comprises detecting the TID-1 in a prostate sample from the animal subject without determining the level of calreticulin. When the TID-1 is low to undetectable in a tumor cell of a prostate sample (e.g., no staining by immunohistochemistry is observed or no detection by a Northern blot), the subject is identified as being likely to have an aggressive prostate cancer.

In still another embodiment, the method comprises detecting the TID-1 in a tissue sample from the animal subject. Such tissues include epithelium tissue, kidney, lymph nodes, and blood tissue. When the TID-1 is low to undetectable in a tumor cell of a tissue sample (e.g., no staining by immunohistochemistry is observed or no detection by a Northern blot), the subject is identified as being likely to have an aggressive cancer.

The present invention also provides methods of identifying an animal subject that is likely to have a slow growing prostate cancer. In one embodiment the likelihood determined is between 50 to 100%. In another embodiment the likelihood determined is greater than 70%. In a preferred embodiment, the method identifies an individual that has an 80% or more likelihood of having a slow growing form of prostate cancer. One such embodiment comprises detecting TID-1 in a prostate sample from the subject. The TID-1 can be detected by Western blot and/or Northern blot and/or as provided for below. When the TID-1 is detectable in the prostate sample from the animal subject the animal subject is identified as being likely to have a slow growing prostate cancer. In one embodiment, the sample is obtained by radical prostatectomy. In another embodiment, the sample is obtained by needle biopsy. In a particular embodiment the level of TID-1 detected is about 50% or more compared to the normal level observed in slow growing prostate cancers.

In one embodiment the determination of the level of TID-1 is performed in situ. In another embodiment the determination of the level of TID-1 is performed in vitro. In still another embodiment, the determination of the level of TID-1 is performed in vivo. In a particular embodiment the determination of the level of TID-1 is performed with an antibody specific for TID-1. In another such embodiment the determination of the level of TID-1 is performed by PCR with a primer specific for an mRNA encoding TID-1. In still another embodiment the determination of the level of TID-1 is performed with a nucleotide probe specific for an mRNA encoding TID-1. In still another embodiment the determination of the level of TID-1 is performed by a Northern blot. In yet another embodiment the determination of the level of TID-1 is performed by a ribonuclease protection assay. In still another embodiment the determination of the level of TID-1 is performed by immunohistochemistry. In yet another embodiment the determination of the level of TID-1 is performed by Laser capture microscopy coupled with a Western blot. In still another embodiment the determination of the level of TID-1 is performed by RT-PCR.

In a preferred embodiment, the method further comprises determining the level of calreticulin in a prostate sample from the subject. When the level of calreticulin is not down-regulated e.g., no more than about 50% down-regulated in the tumor cells relative to that determined in benign prostatic epithelial cells of the same specimen, the subject is identified as being likely to have a slow growing prostate cancer.

In yet another embodiment, the level of calreticulin in a prostate sample from the subject is determined without determining the TID-1. When the level of calreticulin is not down-regulated in the prostate sample from the subject relative to a healthy prostate sample, the subject is identified as being likely to have a slow growing prostate cancer.

In another aspect of the present invention an isolated nucleic acid encoding a TID-1 is provided. In one such embodiment, the nucleic acid encodes a TID-1 that is a transcription factor comprising an amino acid sequence that has at least 25% identity with that of SEQ ID NO:18. In a preferred embodiment, the nucleic acid encodes a TID-1 that comprises a nuclei localization signal and/or a glutamine rich region. Preferably, the nucleic acid encodes a TID-1 that is localized in the nuclei. In a particular embodiment the nucleic acid encodes a TID-1 whose expression is restricted to the male sex accessory organs, as is the case in the rat. In another embodiment, the nucleic acid encodes a TID-1 that has an apoptosis-inducing domain (e.g., the protein and/or a fragment thereof can induce apoptosis in a cell). In another embodiment, the nucleic acid encodes a TID-1 that has a transactivation domain. Preferably, the nucleic acid encodes a TID-1 whose expression is regulated by testosterone.

In a preferred embodiment, the nucleic acid encodes a TID-1 that is a mammalian protein. In embodiment of this type, the nucleic acid encodes a rat TID-1 protein. In one such embodiment, the rat protein comprises the amino acid sequence of SEQ ID NO:14. In a particular embodiment of this type, the nucleic acid that encodes the rat TID-1 comprises the nucleotide sequence of SEQ ID NO:13. In another such embodiment the nucleic acid encodes a rat protein that comprises the amino acid sequence of SEQ ID NO:14 comprising a conservative amino acid substitution.

In another embodiment the nucleic acid encodes a mouse TID-1 protein. In one such embodiment, the mouse protein comprises the amino acid sequence of SEQ ID NO:16. In a particular embodiment of this type, the nucleic acid that encodes the mouse TID-1 comprises the nucleotide sequence of SEQ ID NO:15. In another such embodiment the nucleic acid encodes a mouse protein that comprises the amino acid sequence of SEQ ID NO:16 comprising a conservative amino acid substitution.

In yet another embodiment the nucleic acid encodes a human TID-1 protein. In one such embodiment, the human protein comprises the amino acid sequence of SEQ ID NO:18. In a particular embodiment, the nucleic acid that encodes the human TID-1 comprises the nucleotide sequence of SEQ ID NO 17. In another such embodiment the nucleic acid encodes a human protein that comprises the amino acid sequence of SEQ ID NO:18 comprising a conservative amino acid substitution.

In a related embodiment, the nucleic acid encodes a mammalian EAF1 protein. In a preferred embodiment the mammalian EAF1 is a human protein. In one such embodiment, the human protein comprises the amino acid sequence of SEQ ID NO:20. In a particular embodiment of this type, the nucleic acid that encodes the human EAF1 comprises the nucleotide sequence of SEQ ID NO:19. In another such embodiment the nucleic acid encodes a human EAF1 that comprises the amino acid sequence of SEQ ID NO:20 comprising a conservative amino acid substitution.

The present invention further provides nucleic acids encoding a functional fragment of TID-1, e.g., the apoptosis-inducing domain and/or the transactivation domain. In a preferred embodiment the nucleic acid encodes an apoptosis-inducing domain comprising the 46 amino acid residues encoded essentially by exon III of a TID-1 (see FIGS. 14 and 18). In an alternative embodiment the trans-activation domain comprises the 147–149 amino acids encoded by exons IV–VI of a TID-1 (see FIGS. 14 and 18).

In a particular embodiment, the nucleic acid encodes amino acids 1–113 of SEQ ID NO:14. In another embodiment, the nucleic acid encodes amino acids 1–113 of SEQ ID NO:16. In still another embodiment, the nucleic acid encodes amino acids 1–113 of SEQ ID NO:18. In yet another embodiment, the nucleic acid encodes amino acids 68–113 of SEQ ID NO:14. In still another embodiment, the nucleic acid encodes amino acids 68–113 of SEQ ID NO:16. In yet another embodiment, the nucleic acid encodes amino acids 68–113 of SEQ ID NO:18. In a preferred embodiment, the nucleic acid encodes 8 to 40 (more preferably 15 to 25) consecutive amino acids from amino acid residues 68–113 of SEQ ID NO:18. Preferably, the product expressed by the nucleic acid retains the ability to stimulate apoptosis in a cell.

All of the nucleic acids of the present invention can further comprise a heterologous nucleotide sequence. In addition, recombinant DNA molecules that are operatively linked to an expression control sequence can be constructed from and/or derived from the nucleic acids of the present invention. Furthermore, expression vectors containing the recombinant DNA molecules of the present invention are also provided. In addition, cells that have been transfected and/or transformed with the expression vectors of the present invention, in which the TID-1 or EAF1 protein is expressed by the cell are also part of the present invention. In a preferred embodiment, the cell is a mammalian cell.

The present invention also provides methods of expressing the recombinant TID-1 polypeptides and fragments thereof of the present invention in cells containing the expression vectors of present invention. One such method comprises culturing the cell in an appropriate cell culture medium under conditions that provide for expression of the recombinant polypeptide (e.g., TID-1 or EAF1) by the cell. In a preferred embodiment, the method further comprises the step of purifying the recombinant TID-1 or EAF1. The purified form of the recombinant TID-1 or EAF1 is also part of the present invention.

The present invention further provides nucleic acids that hybridize under standard conditions to a nucleic acid of the present invention. In a particular embodiment, the nucleic acid comprises the nucleotide sequence of SEQ ID NO:13. In another embodiment, the nucleic acid comprises the nucleotide sequence of SEQ ID NO:15. In yet another embodiment, the nucleic acid comprises the nucleotide sequence of SEQ ID NO:17. In a preferred embodiment, the nucleic acid encodes a TID-1 that comprises a nuclei localization signal and/or a glutamine rich region. Preferably, the nucleic acid encodes a TID-1 that is localized in the nuclei. In a particular embodiment the nucleic acid encodes a TID-1 whose expression is restricted to the male sex accessory organs, as is the case in the rat. In another embodiment, the nucleic acid encodes a TID-1 that has an apoptosis-inducing domain (e.g., the protein and/or a fragment thereof can induce apoptosis in a cell). In another embodiment, the nucleic acid encodes a TID-1 that has a transactivation domain. Preferably, the nucleic acid encodes a TID-1 whose expression is regulated by testosterone.

The present invention also provides nucleotide probes for all of the nucleic acids of the present invention.

The present invention further provides isolated TID-1 polypeptides and fragments thereof. In one such embodiment, the TID-1 is a transcription factor having an amino acid sequence that has at least 25% identity with that of SEQ ID NO:18. In a preferred embodiment, the TID-1 comprises a nuclei localization signal and/or a glutamine rich region. Preferably, the TID-1 is localized in the nuclei. In a particular embodiment the TID-1 is restricted to the male sex accessory organs, as is the case in the rat. In another embodiment, the TID-1 that has an apoptosis-inducing domain (e.g., the protein and/or a fragment thereof can induce apoptosis in a cell). In another embodiment, the TID-1 that has a transactivation domain. Preferably, the TID-1 whose expression is regulated by testosterone.

In a preferred embodiment, the isolated TID-1 is a mammalian protein. In one such embodiment, the isolated TID-1 is a rat TID-1 protein. In a particular embodiment of this type, the rat protein comprises the amino acid sequence of SEQ ID NO:14. In another such embodiment the rat TID-1 comprises the amino acid sequence of SEQ ID NO:14 comprising a conservative amino acid substitution. In another particular embodiment the isolated TID-1 is a mouse TID-1 protein. In one such embodiment of this type, the mouse TID-1 comprises the amino acid sequence of SEQ ID NO:16. In another such embodiment the mouse TID-1 comprises the amino acid sequence of SEQ ID NO:16 comprising a conservative amino acid substitution. In yet another particular embodiment the isolated TID-1 is a human TID-1 protein. In one such embodiment of this type, the human TID-1 comprises the amino acid sequence of SEQ ID NO:18. In another such embodiment the human TID-1 comprises the amino acid sequence of SEQ ID NO:18 comprising a conservative amino acid substitution.

In a related embodiment, the present invention provides a human EAF1 protein. In one such embodiment, the human protein comprises the amino acid sequence of SEQ ID NO:20. In a particular embodiment of this type, the human EAF1 comprises the amino acid sequence of SEQ ID NO:20 comprising a conservative amino acid substitution.

The present invention further provides functional fragments of the proteins of the present invention, e.g., the apoptosis-inducing domain and the transactivation domain of TID-1. In a preferred embodiment the apoptosis-inducing domain comprises the 46 amino acid residues encoded essentially by exon III of a TID-1 (see FIGS. 14 and 18). In an alternative embodiment the transactivation domain comprises the 147–149 amino acids encoded by exons IV–VI of a TID-1 (see FIGS. 14 and 18).

In a particular embodiment of this type, the fragment comprises amino acids 1–113 of SEQ ID NO:14. In another embodiment, the fragment comprises amino acids 1–113 of SEQ ID NO:16. In still another embodiment, the fragment comprises amino acids 1–113 of SEQ ID NO:18. In yet another embodiment, the fragment comprises amino acids 68–113 of SEQ ID NO:14. In still another embodiment, the fragment comprises amino acids 68–113 of SEQ ID NO:16. In yet another embodiment, the fragment comprises amino acids 68–113 of SEQ ID NO:18. In a preferred embodiment, the fragment comprises 8 to 40 (more preferably 15 to 25) consecutive amino acids from amino acid residues 68–113 of SEQ ID NOs:14, 16, and/or 18. Preferably, the fragment retains the ability to stimulate apoptosis in a cell.

In a particular embodiment, the transactivation domain comprises amino acid residues 114–262 of SEQ ID NOs:14 and 16. In still another embodiment the transactivation domain comprises amino acid residues 114–260 of SEQ ID NOs:18. All of the fragments of the present invention can also contain a conservative amino acid substitution.

The present invention also provides antigenic fragments of the TID-1 and EAF1 polypeptides of the present invention, as well as proteolytic fragments of the TID-1 and EAF1 polypeptides of the present invention. Preferably the proteolytic fragments are eight amino acids or larger. In addition, the present invention further provides chimeric/fusion proteins/peptides comprising the TID-1 polypeptides, and fragments thereof, including functional, proteolytic and antigenic fragments. Moreover, the present invention provides chimeric/fusion proteins/peptides comprising the EAF1 polypeptides, and fragments thereof, including functional, proteolytic and antigenic fragments.

Antibodies to the TID-1 polypeptides, to the chimeric/fusion proteins comprising the TID-1 polypeptides, as well as to the fragments of the TID-1 polypeptides, including proteolytic, and antigenic fragments, and to the chimeric/fusion proteins/peptides comprising these fragments are also part of the present invention as are the corresponding antibodies raised against EAF1 polypeptides and fragments etc. In addition, methods of using such antibodies for the prognosis of cancer, and prostate cancer in particular, are also part of the present invention.

In addition, antibodies to calreticulin are also provided. As above, methods of using such antibodies for the prognosis of prostate cancer are also part of the present invention.

The antibodies of the present invention can be polyclonal antibodies, monoclonal antibodies and/or chimeric antibodies. Immortal cell lines that produce a monoclonal antibody of the present invention are also part of the present invention.

The present invention further provides a non-human knockout animal comprising a disruption in an endogenous allele encoding TID-1. Preferably the disruption prevents the expression of a functional TID-1 from that allele. In a preferred embodiment, the non-human knockout animal further comprises a disruption in a second endogenous allele encoding TID-1. The disruption of both alleles preferably prevents the non-human knockout animal from expressing functional endogenous TID-1. In a preferred embodiment the knockout animal is a mouse having the propensity for having cancer.

The present invention also provides a non-human knockout animal comprising a disruption in an endogenous allele encoding EAF1. Preferably the disruption prevents the expression of a functional EAF1 from that allele. In a preferred embodiment, the non-human knockout animal further comprises a disruption in a second endogenous allele encoding EAF1. The disruption of both alleles preferably prevents the non-human knockout animal from expressing functional endogenous EAF1. In a preferred embodiment the knockout animal is a mouse having the propensity for having cancer.

The present invention also provides a non-human transgenic animal that has been constructed to express additional copies of the TID-1 and/or the EAF1 protein. In a preferred embodiment of this type, the non-human transgenic animal is a mouse.

The present invention further provides methods of inducing cells to undergo apoptosis. One such method comprises administering a TID-1 to the cell. Another such method comprises administering the N-terminal fragment of TID-1 or a portion thereof to the cell. In a particular embodiment of this type the N-terminal fragment comprises amino acids 1–113 of SEQ ID NO:14. In another embodiment, the N-terminal fragment comprises amino acids 1–113 of SEQ ID NO:16. In still another embodiment, the N-terminal fragment comprises amino acids 1–113 of SEQ ID NO:18. In yet another embodiment, the portion of the N-terminal fragment comprises amino acids 68–113 of SEQ ID NO:14. In still another embodiment, the portion of the N-terminal fragment comprises amino acids 68–113 of SEQ ID NO:16. In yet another embodiment, the portion of the N-terminal fragment comprises amino acids 68–113 of SEQ ID NO:18. In a preferred embodiment, the portion of the N-terminal fragment comprises 8 to 40 (more preferably 15 to 25) consecutive amino acids from amino acid residues 68–113 of SEQ ID NOs:14, 16, and/or 18.

In another embodiment the method comprises administering EAF1 to the cell. In a related embodiment of this type a portion of an N-terminal fragment of EAF1 is administered to the cell.

The present invention also includes a method of treating cancer in an animal subject, such as an epithelium-derived carcinoma, a kidney cancer, a lymphoma, a leukemia, and preferably prostate cancer. One such method comprises inducing the expression of TID-1 activity in the cells of a specific tissue (e.g., prostate cells) in a patient. In a particular embodiment the expression of TID-1 activity is induced by providing exogenous TID-1 or a fragment thereof to the subject via gene therapy. In another embodiment the expression of TID-1 activity is induced by peptide-directed delivery of TID-1 protein.

Thus, the present invention provides methods of administering TID-1, an N-terminal fragment of TID-1 or a portion thereof, in vivo to a cancerous cell in an animal subject. In a particular embodiment of this type the N-terminal fragment comprises amino acids 1–113 of SEQ ID NO:14. In another embodiment, the N-terminal fragment comprises amino acids 1–113 of SEQ ID NO:16. In still another embodiment, the N-terminal fragment comprises amino acids 1–113 of SEQ ID NO:18. In yet another embodiment, the portion of the N-terminal fragment comprises amino acids 68–113 of SEQ ID NO:14. In still another embodiment, the portion of the N-terminal fragment comprises amino acids 68–113 of SEQ ID NO:16. In yet another embodiment, the portion of the N-terminal fragment comprises amino acids 68–113 of SEQ ID NO:18. In a preferred embodiment, the portion of the N-terminal fragment comprises 8 to 40 (more preferably 15 to 25) consecutive amino acids from amino acid residues 68–113 of SEQ ID NOs:14, 16, and/or 18. Preferably, the animal subject is a human.

In another embodiment the method of treating comprises administering EAF1 in vivo to a cancerous cell contained by the animal subject. In a related embodiment of this type an N-terminal fragment of EAF1 is administered in vivo to a cancerous cell of the animal subject. Preferably, the animal subject is a human. EAF1 can be administered by the same methods as outlined above for TID-1.

Accordingly, it is a principal object of the present invention to provide new methods in the prognosis of cancer in humans.

It is a further object of the present invention to provide new protein markers that can be used in the prognosis of cancer in humans, e.g., in the prognosis of prostate cancer.

It is a further object of the present invention to provide new transcription factors that are involved in apoptosis.

It is a further object of the present invention to provide specific probes for assaying tumor tissue to determine whether the tumor cells express TID-1.

It is a further object of the present invention to provide methods for assaying prostate tumor tissue to determine whether calreticulin has been down-regulated.

It is a further object of the present invention to provide new treatments for cancer, particularly prostate cancer.

It is a further object of the present invention to provide new agents for stimulating apoptosis in a cell.

It is a further object of the present invention to provide new agents for inhibiting/preventing apoptosis in a cell.

These and other aspects of the present invention will be better appreciated by reference to the following drawings and Detailed Description.

BRIEF DESCRIPTION OF THE DRAWINGS

FIG. 8A shows the rat TID-1 protein sequence. The TID-1 gene encodes a novel protein with the predicted molecular weight of 29 kDa and an isoelectric point of 4.75 a nucleic acid sequence of SEQ ID NO:13, and an amino acid sequence of SEQ ID NO:14. The underlined sequence is an apparent nuclei localization signal. A glutamine track is localized in the middle of protein, which is apparently part of a transactivation domain.

FIGS. 9B–9G show the effect of TID-1 on colony formation in soft agar assay. The parental PC3, empty vector transfected PC3 sublines M1 and M2, and pcDNA3.1-TID-1 transfected PC3 sublines 27, 41, and 44 were cultured in soft agar for two weeks before taking the pictures.

FIG. 9H shows the effect of fTID-1 expression on cell proliferation. The cell numbers of the parental PC3, empty pCMV-Tag vector transfected PC3 sublines fM1 and fM2, and pCMV-Tag-fTID-1 transfected PC3 sublines f33, f17, and f23 were counted after culture in 6-well plates for 5 days. The proliferation and soft agar assays are described in Methods of Example 3 below.

FIGS. 12A–12F show the effect of TID-1 ectopic expression on the ventral prostate of the transgenic mice. The two boxed areas in each of the 4× figures (FIGS. 12A and 12D) and their 40× enlargements (FIGS. 12B, 12C, 12E and 12E) illustrate the regional heterogeneities of the prostatic ductal systems in both transgenic and non-transgenic ventral prostates. FIGS. 12A–12C are the H&E staining of the ventral prostate of the transgenic (T) and non-transgenic mice (N).

FIGS. 14a–14c display the amino acid sequence and homology, androgen responsiveness, and tissue-specificity of TRAITS. FIG. 14a is an alignment of the human (SEQ ID NO:18), mouse (SEQ ID NO:16), and rat (SEQ ID NO:14) TRAITS amino acid sequences. Dashes indicate deletion and extension; the underlined amino-acids indicate variation among the three sequences. Thick double lines over five pairs of amino acid residues (e.g. RY, EG, RV, RE, and RN) indicate exon junctions (see also FIG. 18). FIG. 14b is a northern blot analysis of androgen induction of TRAITS expression in LNCaP cells. LNCaP cells were treated with or without 10 nM androgen analogue mibolerone (Mib) in the presence or absence of cycloheximide (CHX) at 10 µg/ml. FIG. 14c is a northern blot analysis of TRAITS expression in multiple tissue blots. Commercial human multiple tissue northern blots (CLONTECH) were hybridized with $\alpha^{32}$P-dCTP-labeled 783 bp human TRAITS cDNA probe. Commercial blots are routinely normalized for equal housekeeping (β-actin) gene expression (1 µg poly((+))A RNA). Multiple tissues: 1, adrenal gland; 2, bladder; 3, bone marrow; 4, brain (whole); 5, lymph node; 6, mammary gland; 7, prostate; 8, spinal gland; 9, stomach; 10, thyroid; 11, trachea; 12, uterus; 13, brain; 14, heart; 15, skeletal muscle; 16, colon (no mucosa); 17, thymus; 18, spleen; 19, kidney; 20, liver; 21, small intestine; 22, placenta; 23, lung; 24, peripheral blood leukocyte.

FIG. 15a shows a competitive EMSA analysis of sequence-specific binding of rat TRAITS to DNA sequence ACTTTA (T-box). The binding of GST-TRAITS fusion protein to labeled T-box containing DNA forms a DNA-protein complex (C), which can be competed in the presence of indicated fold (5×, 25×, or 125×) molar excess of cold T-wt but not by cold T-mut (ACTgTA). A non-specific complex (*) in the presence of GST-TRAITS was also formed in the presence of GST only. Labeled free DNA (F) was also indicated. FIG. 15b shows the results of a mammalian two-hybrid analysis of the rat TRAITS transactivation domain. NIH3T3 cells were transiently transfected with empty vector (PM) or vectors expressing the full-length rat TRAITS (residues 1–262 of SEQ ID NO:14), its N-terminal (residues 1–113 of SEQ ID NO:14), or its C-terminal (residues 114–262 of SEQ ID NO:14) plus pG5CAT reporter and pSV-β-gal for normalization. Assays were performed after 24 hours of transfection. The fold activation of CAT reporter is shown with S.E.M. Assays were performed in triplicate in two separate experiments.

FIGS. 16a–16c show the apoptosis induction by TRAITS activation. FIG. 16a shows the activation of the tripartite GFP-TRAITS-ER fusion protein by OHT in PC3 cells. The GFP-TRAITS-ER protein is localized primarily in cytoplasm in the absence of OHT, as visualized under green fluorescent microscope. The fusion protein was translocated into nuclei 24 hours after treatment of the cells with 300 nM OHT and then condensed in the fragmented nuclei 48 hours after the OHT treatment. The condensed and fragmented nuclei of the OHT-treated PC3 cells were then visualized by Hoechst staining. FIG. 16b shows the FACS analysis of annexin V staining for PC3 cells transfected with the tripartite fusion protein. The PC3 cells were cultured in the absence or presence of 300 nM OHT for 72 hours prior to FACS analysis. The figure represents one of the 3 different experiments. FIG. 16c shows PC3 cells that were transiently transfected with the N-terminal portion (residues 1–113 of SEQ ID NO:14) and C-terminal portion (residues 114–262 of SEQ ID NO:14) of TRAITS fused to GFP. Following the culturing of the transfected PC3 cells for 10 days in medium including 500 μg/ml geneticin (G418), none of the cells were found to express the N-terminal fusion protein, whereas many of the cells expressed the C-terminal fusion protein.

DETAILED DESCRIPTION OF THE INVENTION

Figure 1:
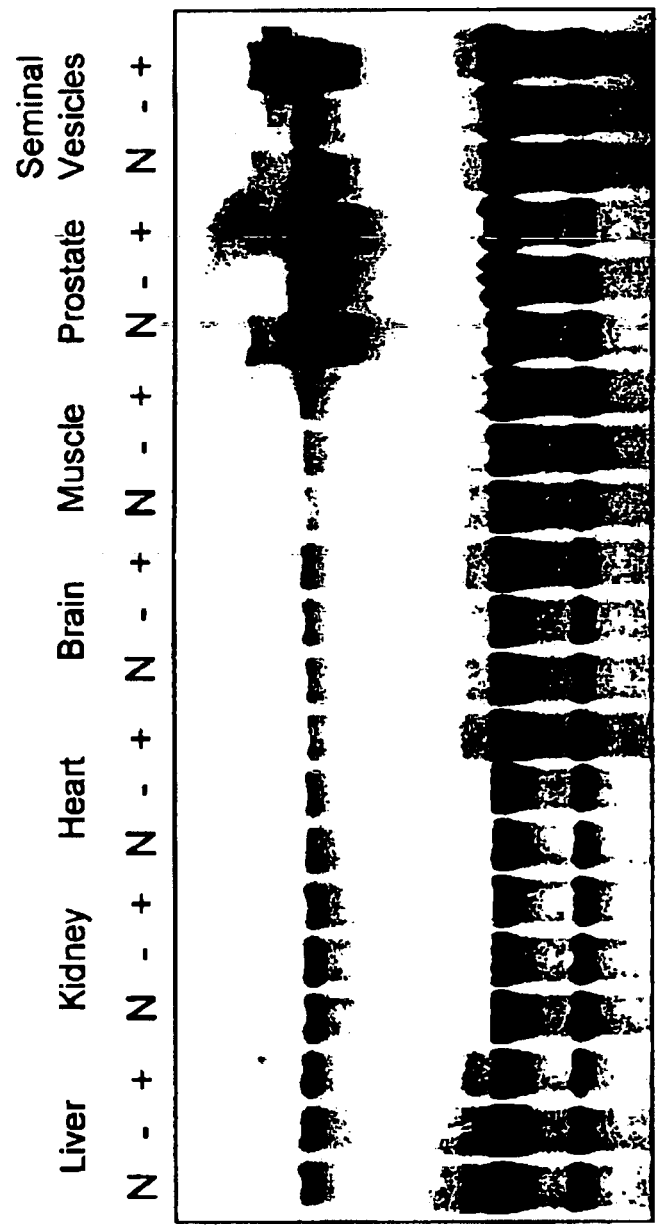
FIG. 1 shows the Northern blot analysis of the tissue-specificity of calreticulin expression in the rat during hormonal manipulation. "N" represents the tissue from the testis-intact rats; "–" represents the tissue from 7-day castrated rats; and "((+))" represents the tissue from the rats castrated for 7 days followed by androgen treatment for an additional 2 days. The amount and quality of total RNA loaded in the gels were examined by staining the transferred nylon membrane with methylene blue.
Figure 2:
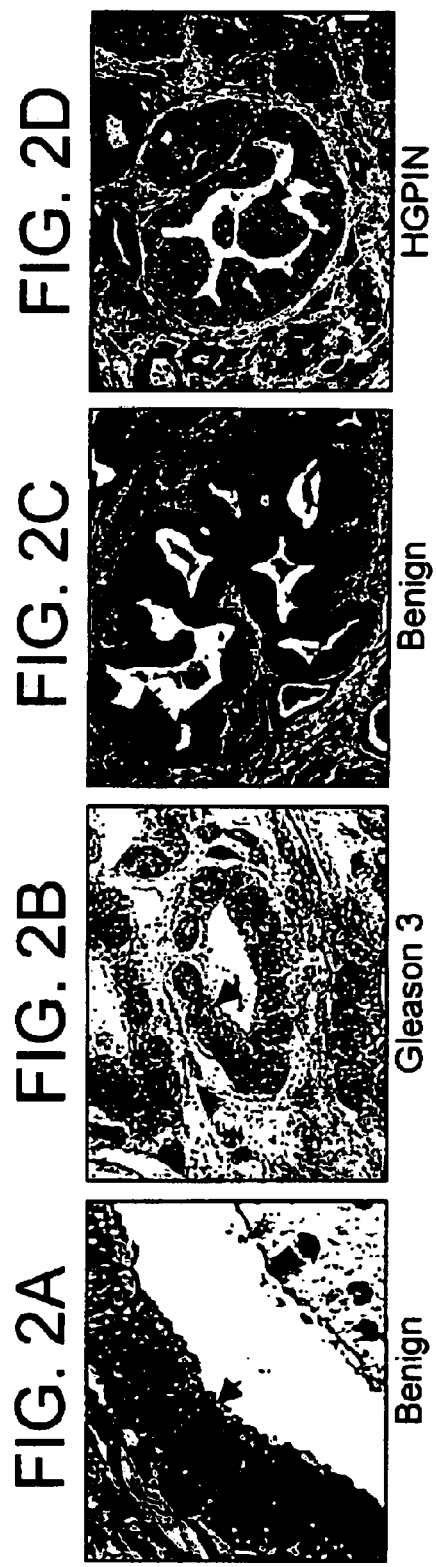
FIGS. 2A–2D depict immunohistochemical studies of calreticulin expression in clinical prostate tumor specimens. One specimen containing both benign prostate (FIG. 2A) and Gleason 3(+)3 cancerous prostate (FIG. 2B) were stained with one anti-Crt antibody and hemotoxylin as described previously [Zhu et al. *Endocrinology* 139:4337–4344 (1998)]. Another specimen containing both benign prostate (FIG. 2C) and HGPIN (FIG. 2D) was stained with a different anti-Crt antibody and without hemotoxylin. Secondary antibody alone did not stain the section. The benign and cancerous epithelial cells are marked with arrows.

One aspect of the present invention relates to two proteins calreticulin and TID-1 (otherwise known as TRAITS), that are encoded by genes that are up-regulated by androgen in the prostate. Calreticulin is a protein that is abundantly expressed in prostatic epithelial cells and is known to play an important role in cellular adhesion and intracellular $Ca^{((+))((+))}$ regulation (e.g., human calreticulin has the amino acid sequence of SEQ ID NO:36, and is encoded by the nucleic acid sequence of SEQ ID NO:35). TID-1, on the other hand is a novel protein (e.g., human TID-1 has the amino acid sequence of SEQ ID NO:18, and is encoded by the nucleic acid sequence of SEQ ID NO:17) that is shown herein to play an important role in the regulation of the proliferation and differentiation of prostatic epithelial cells.

Unexpectedly, part of the androgen action pathway was found to suppress cell proliferation, and this growth suppression is essential for prostate homeostasis. Thus, androgen-response genes play an unexpected and novel role in suppressing prostate epithelial cell proliferation. Furthermore, the growth suppressive part of the androgen action pathway can limit the cell number in the normal prostate, and its inactivation appears to cause uncontrolled growth and lead to prostate cancer. As disclosed herein, both calreticulin and TID-1 play important roles in the part of the androgen action pathway that suppresses cell proliferation and/or prevents prostate cancer.

Calreticulin regulates cell adhesion and intracellular $Ca^{((+))((+))}$ homeostasis in cultured prostate cancer cells. The over-expression of calreticulin markedly suppresses anchorage-independent growth of human prostate cancer cells in soft agar. Since, anchorage-independent growth is a hallmark of malignancy, this result indicates that calreticulin plays a role in the suppression of tumor malignancy. Consistently, restoration of calreticulin expression markedly inhibits the metastasis of xenograft rat Dunning AT3.1 prostate cancer cells in nude mice (see below). Furthermore, whereas calreticulin is abundantly expressed in normal prostatic epithelial cells, it is down-regulated in prostate cancer cells in clinical specimens. Indeed, the calreticulin level is significantly decreased in aggressive prostate cancer cells in clinical prostate cancer specimens, which is again consistent with the tumor suppressive role of calreticulin. Furthermore, calreticulin down-regulation was observed in some high grade prostatic intraepithelial neoplasia (HGPIN), a very early step in prostate cancer progression. This observation indicates that HGPINs with calreticulin down-regulation could be destined to become aggressive prostate cancer. Together, these results imply that calreticulin not only plays an important role in the suppression of prostate cancer, but further, that the down-regulation of calreticulin is linked with the invasiveness of the cancer. Indeed, an essential step in prostate cancer progression appears to be the down-regulation of calreticulin, which reflects and/or mediates the breakdown of the androgen-dependent growth restriction of prostate epithelial cells.

TID-1 has also been found to be involved in the suppressive part of the androgen pathway (see Example 3, below). TID-1 is a novel protein that comprises a nuclei localization signal, a glutamine-rich region, is localized in the nuclei, comprises a transactivation domain in the C-terminal region, an apoptosis including domain in the N-terminal region, and binds to DNA in a sequence-specific fashion (ACTTTA). These characteristics are consistent with TID-1 being a transcription factor. The expression of TID-1 is regulated by testosterone. TID-1 is a conserved approximately 29 kd nuclear protein expressed in many human tissues with the most abundant expression in the prostate, bone marrow, kidney and lymph node.

Importantly, TID-1 expression was down-regulated, and/or not detectable in all prostate cancer cell lines examined. Ectopic expression of TID-1 induced massive cell death in LNCaP human prostate cancer cells, as well as in practically all of the other human prostate cancer cells examined, indicating that TID-1 is a death factor in prostate cancer cells. Indeed, the difficulty in establishing stably transfected cell lines in PC3, DU145, and TSU prostate cancer cells indicated that TID-1 ectopic expression is consistent with this transcription factor being detrimental to these cell lines. The few stably transfected prostate cancer cell lines that were isolated having very low TID-1 expression levels exhibited a significantly reduced proliferation rate. These results indicate that TID-1 expression is associated with less aggressive prostate cancers. Indeed, since advanced prostate cancer cells do not express TID-1, TID-1 can therefore serve as a marker to distinguish slow-growing prostate cancers from aggressive prostate cancers.

Activation of TID-1 downstream signaling events also appear to lead to cell death in prostate cancer cells. Thus, TID-1 also represents a novel target for the treatment of cancer, particularly prostate cancer. In addition, TID-1, and/or fragments thereof can be used in cancer therapy. Since TID-1 ectopic expression induces massive cell death in human LNCaP prostate cancer cells the restoration of TID-1 in prostate cancer cells should induce cell death and inhibit prostate cancer. Alternatively, activation of the TID-1 downstream signaling events could also lead to cell death in prostate cancer cells. Importantly, as disclosed herein peptides comprising amino acids 68–113 of SEQ ID NOs:14, 16, and 18 have been shown to also stimulate this apoptotic effect.

The present invention also provides methods of prognosticating the progression of cancer in an animal subject, particularly prostate cancer. For example, prostate cancer cells that express TID-1 are slow-growing, whereas TID-1 negative prostate cancer cells are aggressive. Therefore, the level of TID-expression may distinguish patients that need aggressive treatment from those that only need to be monitored. Thus, determination of the TID-1 expression may provide physicians with a powerful prognosis tool. Similarly, a significant decrease in the cell calreticulin level appears to be indicative of an aggressive, malignant prostate cancer. Therefore, the determination of whether there is a down-regulation of calreticulin in a prostate cell sample can be used as a screen to distinguish aggressive malignant prostate cancers, which need aggressive treatment, from less aggressive forms, which may only require monitoring. Therefore, the present invention provides complementary marker proteins for identifying either slowly progressing or aggressive prostate cancers.

Thus, in one aspect of the invention, the prognosis is based on either directly or indirectly measuring the levels of proteins involved in the androgen-dependent suppression of prostate cell proliferation and metastasis. In one embodiment of the invention, the prognosis is performed by measuring the level of expression of TID-1 in prostate cells, significant levels of which are indicative of a slowly progressing cancer. In another embodiment, the prognosis is performed by measuring the level of expression of calreticulin in prostate cells, low levels of which are indicative of a rapidly progressing cancer. In yet another embodiment of the invention, the prognosis is performed by determining the levels of both TID-1 expression and calreticulin expression in prostatic epithelial cells.

Another aspect of the present invention relates to a novel protein EAF1 (see Example 4 below) which is not induced by testosterone, but has strong homology to TID-1. Both TID-1 and EAF1 can be used in the treatment of cancer since both proteins induce apoptosis in a cell. The methods of treating cancer in an animal subject provided herein include epithelium-derived carcinomas, kidney cancers, lymphomas, leukemias, and particularly, prostate cancer.

Therefore, if appearing herein, the following terms shall have the definitions set out below:

As used herein, the term "TID-1" is used interchangeably with the terms "U19" and "TRAITS" and is a novel testosterone regulated apoptosis inducer and tumor suppressor. TID-1 is a novel protein that comprises a nuclei localization signal, a glutamine-rich region, is localized in the nuclei, a transactivation domain in the C-terminal region, an apoptosis-inducing domain in the N-terminal region and binds to DNA in a sequence-specific fashion (ACTTTA). The expression of TID-1 is regulated by testosterone. In one embodiment the TID-1 is encoded by a rat nucleic acid having the nucleic acid sequence of SEQ ID NO:13. In a related embodiment the TID-1 is a rat protein having the amino acid sequence of SEQ ID NO:14. In still another embodiment, the TID-1 is encoded by a mouse nucleic acid having the nucleic acid sequence of SEQ ID NO:15. In a related embodiment the TID-1 is a mouse protein having the amino acid sequence of SEQ ID NO:16. In yet another embodiment the TID-1 is a human nucleic acid having the nucleic acid sequence of SEQ ID NO:17. In a related embodiment the TID-1 is a human protein having the amino acid sequence of SEQ ID NO:18.

As used herein a "glutamine-rich region" is a particular region of a protein that is generally associated with trans-activation domain of a transcription factor.

As used herein an "apoptosis-inducing domain" is a region of a protein that confers the apoptotic property to a given protein such as TRAITS. Such apoptosis-inducing domains are exemplified herein as amino acids 68–113 of SEQ ID NOs:14, 16, and 18. Preferably, an apoptosis-inducing domain (e.g., a peptide fragment comprising the apoptosis-inducing domain) alone can induce apoptosis in a cell.

As used herein, the "N-terminal region" of TID-1 is approximately amino acids 1–113 of SEQ ID NOs:14, 16, and 18, whereas the "C-terminal region" is the remaining approximately 147–149 amino acids of the protein.

As used herein a protein is "restricted to the male sex accessory organs" when it is only detected in the male sex accessory organs when a tissue survey is performed by Northern blot analysis.

As used herein "the androgen action pathway" is defined as a cascade of molecular and cellular events triggered by androgen manipulation leading to cell proliferation, apoptosis, and/or differentiation.

As used herein the terms "fusion protein" and "fusion peptide" are used interchangeably and encompass "chimeric proteins and/or chimeric peptides" and fusion "intein proteins/peptides". A fusion protein of the present invention comprises at least a portion of a TID-1, EAF1, or calreticulin of the present invention joined via a peptide bond to at least a portion of another protein or peptide including a second portion of TID-1, EAF1 or calreticulin in a chimeric fusion protein. In a particular embodiment the portion of the TID-1 is antigenic. For example, fusion proteins can comprise a marker protein or peptide, or a protein or peptide that aids in the detection, isolation and/or purification of a TID-1 of the present invention.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

As used herein the terms "approximately" and "about" are used to signify that a value is within twenty percent of the indicated value i.e., a protein fragment containing "approximately" 150 amino acid residues can contain between 120 and 180 amino acid residues.

As used herein a "small organic molecule" is an organic compound [or organic compound complexed with an inorganic compound (e.g., metal)] that has a molecular weight of less than 3 Kilodaltons, preferably less than 1.5 Kilodaltons.

As used herein a polypeptide or peptide "consisting essentially of" or that "consists essentially of" a specified amino acid sequence is a polypeptide or peptide that retains the general characteristics, e.g., activity of the polypeptide or peptide having the specified amino acid sequence and is otherwise identical to that protein in amino acid sequence except it consists of plus or minus 10% or fewer, preferably plus or minus 5% or fewer, and more preferably plus or minus 2.5% or fewer amino acid residues. Thus, a polypeptide that consists essentially of an amino acid sequence of SEQ ID NO:18 consists of between 229 to 292 amino acids, preferably 253 to 279, and more preferably 259 to 273 amino acids. Preferably the additional/missing amino acids are at or near the C-terminal or N-terminal portion of the protein.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such solvent preferences.

As used herein, the term "homologue" is used interchangeably with the term "ortholog" and refers to the relationship between proteins that have a common evolutionary origin and differ because they originate from different species. For example, rat TID-1 is a homologue of human TID-1.

Nucleic Acids Encoding TID-1

The present invention contemplates isolation of a nucleic acid encoding a TID-1 (or EAF1), including a full length, or naturally occurring form of TID-1 (or EAF1) from any species, preferably an animal, and more particularly a mammalian source. Nucleic acids encoding rat, mouse, and human TID-1 and human EAF1 are exemplified below.

In accordance with the present invention there may be employed conventional molecular biology, microbiology, and recombinant DNA techniques within the skill of the art. Such techniques are explained fully in the literature. [See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II D. N. Glover ed. 1985; *Oligonucleotide Synthesis*, M. J. Gait ed. (1984); *Nucleic Acid Hybridization*, B. D. Hames & S. J. Higgins eds. (1985); *Transcription And Translation*, B. D. Hames & S. J. Higgins, eds. (1984); *Animal Cell Culture*. R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994)].

Therefore, if appearing herein, the following terms shall have the definitions set out below.

As used herein, the term "gene" refers to an assembly of nucleotides that encodes a polypeptide, and includes cDNA and genomic DNA nucleic acids. A nucleic acid encoding a TID-1 of the present invention is not used herein as a synonym of the corresponding naturally occurring gene which contains all of the introns and regulatory sequences, e.g., promoters, present in the natural genomic DNA. Rather, a nucleic acid encoding a particular protein can minimally contain just the corresponding coding nucleotide sequence for the protein.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA—RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. Such designations include SEQ ID NOs:. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. In preferred embodiments the hybridization conditions described herein are identical to the wash conditions.

For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 16 nucleotides; and more preferably the length is at least about 24 nucleotides; and most preferably at least 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 25% of the amino acids are identical (preferably at least about 50%, more preferably at least about 75%, and most preferably at least about 90 or 95% identical), or greater than about 60% (preferably at least about 75%, more preferably at least about 90%, and most preferably at least about 95 or 100%) are functionally identical. The sequence comparison is performed over a contiguous block of amino acid residues comprised by human TID-1 (hTID-1), for example. Thus, when comparing a particular full-length vertebrate TID-1 with hTID-1 having the amino acid sequence of SEQ ID NO:18, the contiguous block of amino acids is about 266 residues. In a preferred embodiment selected deletions or insertions that could otherwise alter the correspondence between the two amino acid sequences are taken into account. Preferably standard computer analysis is employed for the determination that is comparable, (or identical) to that determined with an Advanced Blast search at www.ncbi.nlm.nih.gov under the default filter conditions [e.g., using the GCG (Genetics Computer Group, Program Manual for the GCG Package, Version 7, Madison, Wis.) pileup program using the default parameters].

The term "corresponding to" is used herein to refer similar or homologous sequences, whether the exact position is identical or different from the molecule to which the similarity or homology is measured. Thus, the term "corresponding to" refers to the sequence similarity over a given sequence range (e.g. 50 nucleotides), and not the numbering of the amino acid residues or nucleotide bases.

A gene encoding a TID-1 (or EAF1) protein, whether genomic DNA or cDNA, can be isolated from any source, particularly from a human cDNA or genomic library. Methods for obtaining a TID-1 (or EAF1) gene with the nucleotide information disclosed herein is well known in the art [see, e.g., Sambrook et al., 1989, supra].

Accordingly, any animal cell potentially can serve as the nucleic acid source for the molecular cloning of a TID-1 gene for example. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al., 1989, supra; Glover, D. N. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired TID-1 gene may be accomplished in a number of ways. For example, if an amount of a portion of a TID-1 gene or its specific RNA, or a fragment thereof, is available and can be purified and labeled, the generated DNA fragments may be screened by nucleic acid hybridization to the labeled probe [Benton and Davis, Science, 196:180 (1977); Grunstein and Hogness, Proc. Natl. Acad. Sci. U.S.A., 72:3961 (1975)]. For example, a set of oligonucleotides corresponding to the partial amino acid sequence information obtained for the TID-1 protein can be prepared and used as probes for DNA encoding a TID-1. Preferably, a fragment is selected that is highly unique to a TID-1. Those DNA fragments with substantial homology to the probe will hybridize. As noted above, the greater the degree of homology, the more stringent hybridization conditions can be used. In a specific embodiment, stringent hybridization conditions are used to identify a homologous TID-1 gene.

Further selection can be carried out on the basis of the properties of the gene, e.g., if the gene encodes a protein product having the isoelectric, electrophoretic, amino acid composition, or partial amino acid sequence of a TID-1 as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for a TID-1.

A TID-1 gene can also be identified by mRNA selection, i.e., by nucleic acid hybridization followed by in vitro translation. In this procedure, nucleotide fragments are used to isolate complementary mRNAs by hybridization. Such DNA fragments may represent available, purified TID-1 DNA, or may be synthetic oligonucleotides designed from the partial amino acid sequence information. Immunoprecipitation analysis or functional assays (e.g., effecting apoptosis in prostate cancer cells) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against TID-1.

The nucleotide sequence of the rat, mouse or human TID-1, SEQ ID NOs:13, 15, and 17 respectively, can also be used to search for highly homologous genes from other species, or for proteins having at least one homologous domain, using computer data bases containing either partial or full length nucleic acid sequences (see Example 4 below). Human ESTs, for example, can be searched. The human TID-1 sequence can be compared with human sequences, e.g., in GenBank, using GCG software and the blast search program for example. Matches with highly homologous sequences or portions thereof can then be obtained.

If the sequence identified is an EST, the insert containing the EST can be obtained and then fully sequenced. The resulting sequence can then be used in place of, and/or in conjunction with SEQ ID NOs:13, 15 and/or 17 to identify other ESTs which contain coding regions of the TID-1 homologue (or TID-1 domain homologue). Plasmids containing the matched EST for example can be digested with restriction enzymes in order to release the cDNA inserts. If the plasmid does not contain the full length homologue the digests can be purified, e.g., run on an agarose gel and the bands corresponding to the inserts can be cut from the gel and purified. Such purified inserts are likely to contain overlapping regions which can be combined as templates of a PCR reaction using primers which are preferably located outside of the TID-1 open reading frame. Amplification should yield the expected product which can be ligated into a vector and used to transform an E coli derivative e.g., via TA cloning (Invitrogen) for example. A resulting full-length TID-1 homologue can be placed into an expression vector and the expressed recombinant TID-1 can then be assayed for apoptotic activity in prostate cancer cells.

Alternatively, plasmids containing matched EST homologue fragments can be used to transform competent bacteria (e.g, from Gibco BRL, Gaithersburg Md.). Bacteria can be streaked, then grown up overnight. Plasmid preps can be performed (e.g., Quiagen Corp, Santa Clarita Calif.) and the plasmids can be digested by simultaneous restriction digest. Products of the digest can be separated by size on an agarose gel, for example, and purified. The corresponding bands cut from these gels can be ligated to form a full length TID-1 cDNA and used to transform competent bacteria and the resulting plasmid can be purified.

A radiolabeled TID-1 cDNA can be synthesized using the selected mRNA (from the adsorbed polysomes) as a template. The radiolabeled mRNA or cDNA may then be used as a probe to identify homologous TID-1 DNA fragments from among other genomic DNA fragments.

The present invention also relates to cloning vectors containing genes encoding the domains of the TID-1 proteins of the invention. The production and use of such derivatives and analogs are within the scope of the present invention.

A modified TID-1 can be made by altering nucleic acid sequences encoding the TID-1 by making substitutions, additions or deletions that provide for functionally equivalent molecules. Preferably, such derivatives are made that have enhanced or increased apoptotic activity relative to the TID-1.

Due to the degeneracy of nucleotide coding sequences, other DNA sequences which encode substantially the same amino acid sequence as a TID-1 gene may be used in the practice of the present invention including those comprising conservative substitutions thereof. These include but are not limited to modified allelic genes, modified homologous genes from other species, and nucleotide sequences comprising all or portions of TID-1 genes which are altered by the substitution of different codons that encode the same amino acid residue within the sequence, thus producing a silent change. Likewise, the TID-1 derivative of the invention can include, but is not limited to, those containing, as a primary amino acid sequence, all or part of the amino acid sequence of a TID-1 protein including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding TID-1 (or EAF1) derivatives and analogs of the invention can be produced by various methods known in the art. The manipulations which result in their production can occur at the gene or protein level. For example, a TID-1 gene sequence can be produced from a native TID-1 clone by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of a TID-1, care should be taken to ensure that the modified gene remains within the same translational reading frame as the TID-1 gene, uninterrupted by translational stop signals, in the gene region where the desired activity is encoded.

Additionally, the TID-1-encoding nucleic acid sequence can be produced by in vitro or in vivo mutations, to create and/or destroy translation, initiation, and/or termination sequences, or to create variations in coding regions and/or form new restriction endonuclease sites or destroy preexisting ones, to facilitate further in vitro modification. Preferably such mutations will further enhance the specific properties of the TID-1 gene product. Any technique for mutagenesis known in the art can be used, including but not limited to, in vitro site-directed mutagenesis [Hutchinson, C., et al., *J. Biol. Chem.*, 253:6551 (1978); Zoller and Smith, *DNA*, 3:479–488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis (see Higuchi, 1989, "Using PCR to Engineer DNA", in PCR *Technology: Principles and Applications for DNA Amplification*, H. Erlich, ed., Stockton Press, Chapter 6, pp. 61–70). A general method for site-specific incorporation of unnatural amino acids into proteins is described in Noren et al., [*Science*, 244:182–188 (1989)]. This method may be used to create analogs with unnatural amino acids.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of TID-1 and (EAF1) Polypeptides

The nucleotide sequence coding for a TID-1 or EAF1, or a functionally equivalent derivative including a fusion/chimeric protein thereof, can be inserted into an appropriate expression vector, i.e., a vector which contains the necessary elements for the transcription and translation of the inserted protein-coding sequence. Such elements are termed herein a "promoter." Thus, for example, a nucleic acid encoding a TID-1 of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding TID-1 and/or its flanking regions. Any person with skill in the art of molecular biology or protein chemistry, in view of the present disclosure, would readily know how to assay the protein expressed as described herein, to determine whether such a modified protein is indeed a TID-1. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant TID-1 or EAF1 of the invention, or functionally equivalent derivative, or fusion/chimeric construct may be expressed chromosomally, after integration of the coding sequence by recombination. In this regard, any of a number of amplification systems may be used to achieve high levels of stable gene expression [See Sambrook et al., 1989, supra]. Chromosomal integration, e.g., by homologous recombination is desirable where permanent expression is required, such as to immortalize an antibody-producing plasma cell. In other embodiments, such as for in vitro propagation of cells for transplantation, transient transfection such as with a plasmid, is preferable. This way, the cell can be propagated indefinitely in vitro, but will terminally differentiate when reintroduced in vivo.

The cell containing the recombinant vector comprising the nucleic acid encoding a TID-1, for example, is cultured in an appropriate cell culture medium under conditions that provide for expression of the TID-1 by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a TID-1 or EAF1 may be controlled by any promoter/enhancer element known in the art, but these regulatory elements must be functional in the host selected for expression. Promoters which may be used to control TID-1 gene expression for example, include, but are not limited to, the SV40 early promoter region [Benoist and Chambon, *Nature*, 290:304–310 (1981)], the promoter contained in the 3' long terminal repeat of Rous sarcoma virus [Yamamoto, et al., *Cell*, 22:787–797 (1980)], the herpes thymidine kinase promoter [Wagner et al., *Proc. Natl. Acad. Sci. U.S.A.*, 78:1441–1445 (1981)], the regulatory sequences of the metallothionein gene [Brinster et al., *Nature*, 296:39–42 (1982)]; prokaryotic expression vectors such as the β-lactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)]; see also "Useful proteins from recombinant bacteria" in *Scientific American*, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984); Ornitz et al., *Cold Spring Harbor Symp. Quant. Biol.*, 50:399–409 (1986); MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., *Cell*, 38:647–658 (1984); Adames et al., *Nature*, 318:533–538 (1985); Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Pinkert et al., *Genes and Devel.*, 1:268–276 (1987)], alpha-fetoprotein gene control region which is active in liver [Krumlauf et al., *Mol. Cell. Biol.*, 5:1639–1648 (1985); Hammer et al., *Science*, 235:53–58 (1987)], alpha 1-antitrypsin gene control region which is active in the liver [Kelsey et al., *Genes and Devel.*, 1:161–171 (1987)], beta-globin gene control region which is active in myeloid cells [Mogram et al., *Nature*, 315:338–340 (1985); Kollias et al., *Cell*, 46:89–94 (1986)], myelin basic protein gene control region which is active in oligodendrocyte cells in the brain [Readhead et al., *Cell*, 48:703–712 (1987)], myosin light chain-2 gene control region which is active in skeletal muscle [Sani, *Nature*, 314:283–286 (1985)], and gonadotropic releasing hormone gene control region which is active in the hypothalamus [Mason et al., *Science*, 234:1372–1378 (1986)].

Expression vectors containing a nucleic acid encoding a TID-1 of the invention can be identified by many means including by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a TID-1 is inserted within the "selection marker" gene sequence of the vector, recombinants containing the TID-1 insert can be identified by the absence of the TID-1 gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene,* 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used. Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; [see Kaufman, *Current Protocols in Molecular Biology,* 16.12 (1991)]. Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, geneticin (G418) selectable marker; Invitrogen), and pEBVHis (RSV-LTR promoter, hygromycin selectable marker, N-ternminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express the TID-1 protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an non-glycosylated core protein product. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the TID-1 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, *J. Biol. Chem.*, 263:14621–14624 (1988); Hartmut et al., Canadian Patent Application No. 2,012,311, filed Mar. 15, 1990)].

General Protein Purification Procedures

Initial steps for purifying the TID-1 (or EAF1) protein of the present invention can include salting in or salting out, such as in ammonium sulfate fractionations; solvent exclusion fractionations, e.g., an ethanol precipitation; detergent extractions to free membrane bound proteins using such detergents as TRITON X-100, TWEEN-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer; affinity-binding, immuno-binding, using e.g., an antibody to a TID-1 bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations of buffer salts are used. Low concentration buffers generally imply 5–25 mM concentrations. High concentration buffers generally imply concentrations of the buffering agent of between 0.1–2 M concentrations. Typical buffers can be purchased from most biochemical catalogues and include the classical buffers such as Tris, pyrophosphate, monophosphate and diphosphate and the Good buffers [Good et al., *Biochemistry*, 5:467 (1966); Good and Izawa, *Meth. Enzymol.*, 24B:53 (1972); and Fergunson and Good, *Anal. Biochem.*, 104:300 (1980] such as Mes, Hepes, Mops, tricine and Ches.

Materials to perform all of these techniques are available from a variety of sources such as Sigma Chemical Company in St. Louis, Mo.

In the Example below a particular method of purifying recombinant human TID-1 is described.

Antibodies to the TID-1 and EAF1 Proteins of the Present Invention

According to the present invention, the TID-1 (or EAF1) as produced by a recombinant source, or through chemical synthesis, or a TID-1 (or EAF1) isolated from natural sources; and derivatives or analogs thereof, including fusion proteins, may be used as an immunogen to generate antibodies that recognize the TID-1 (or EAF1), as exemplified below. Such antibodies include but are not limited to polyclonal, monoclonal, chimeric including humanized chimeric, single chain, Fab fragments, and a Fab expression library. The anti-TID-1 antibodies, for example, of the invention may be cross reactive, that is, they may recognize a TID-1 derived from a different source. Polyclonal antibodies have greater likelihood of cross reactivity. Alternatively, an antibody of the invention may be specific for a single form of a TID-1, such as the human TID-1 having the amino acid sequence of SEQ ID NO:18, or a fragment of the human TID-1 comprising the apoptosis-inducing domain, e.g., amino acid residues 68–113 of SEQ ID NO:18.

Various procedures known in the art may be used for the production of polyclonal antibodies to TID-1 (or EAF1) or derivatives or analogs thereof. For the production of antibody, various host animals can be immunized by injection with the TID-1 (or EAF1), or a derivative (e.g., or fusion protein) thereof, including but not limited to rabbits, mice, rats, sheep, goats, etc. In one embodiment, the TID-1 or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the TID-1 (or EAF1), or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604–608 (1984); Takeda et al., *Nature,* 314:452–454 (1985)] by splicing the genes from a mouse antibody molecule specific for a TID-1 together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce e.g., TID-1-specific single chain antibodies. An additional embodiment of the invention utilizes the techniques described for the construction of Fab expression libraries [Huse et al., *Science,* 246:1275–1281 (1989)] to allow rapid and easy identification of monoclonal Fab fragments with the desired specificity for a TID-1, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of TID-1, one may assay generated hybridomas for a product which binds to the TID-1 fragment containing such epitope and choose those which do not cross-react with TID-1. For selection of an antibody specific to a TID-1 from a particular source, one can select on the basis of positive binding with TID-1 expressed by or isolated from that specific source.

The foregoing antibodies can be used in methods known in the art relating to the localization and activity of the TID-1, e.g., for Western blotting, imaging TID-1 in situ, measuring levels thereof in appropriate physiological samples, etc. using any of the detection techniques mentioned herein or known in the art.

In a specific embodiment, antibodies that agonize or antagonize the activity of TID-1 can be generated. Such antibodies can be tested using the assays described infra for identifying ligands.

Labels

The TID-1 (or EAF1) proteins of the present invention, antibodies to the TID-1 (or EAF1) proteins, nucleic acids that hybridize to SEQ ID NOs:13, 15, 17 or 19 (e.g. probes) etc. can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3((+))}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Such labels may also be appropriate for the nucleic acid probes used in binding studies with TID-1. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313, 734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453.

Suitable enzymes include, but are not limited to, alkaline phosphatase and horseradish peroxidase.

In addition, a TID-1, a fragment thereof, an EAF1 or fragment thereof can be modified to contain a marker protein such as green fluorescent protein as described in U.S. Pat. No. 5,625,048 filed Apr. 29, 1997, WO 97/26333, published Jul. 24, 1997 and WO 99/64592 all of which are hereby incorporated by reference in their entireties.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Gene Therapy and Transgenic Vectors

A gene encoding a TID-1 or derivative thereof, or structural/functional domain thereof, including an inactive derivative, or alternatively a TID-1 homologue such as EAF1 or fragment thereof, can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of prostate cells can be specifically targeted. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-Perricaudet et al. [*J. Clin. Invest.*, 90:626–630 (1992)], and a defective adeno-associated virus vector [Samulski et al., *J. Virol.*, 61:3096–3101 (1987); Samulski et al., *J. Virol.*, 63:3822–3828 (1989)] including a defective adeno-associated virus vector with a tissue specific promoter, [see e.g., U.S. Pat. No. 6,040,172, Issued Mar. 21, 2000].

In a preferred embodiment of the present invention, a gene therapy vector as described above employs a transcription control sequence operably associated with the sequence for the TID-1 (or EAF1) inserted in the vector. That is, a specific expression vector of the present invention can be used in gene therapy.

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine*, (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., *Blood*, 82:845 (1993).

Targeted gene delivery is described in International Patent Publication WO 95/28494, published October 1995.

Alternatively, the vector can be introduced by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.*, 84:7413–7417 (1987); see Mackey, et al., *Proc. Natl. Acad. Sci. U.S.A.*, 85:8027–8031 (1988)]. The use of cationic lipids may promote encapsulation of negatively charged nucleic acids, and also promote fusion with negatively charged cell membranes [Felgner and Ringold, *Science*, 337:387–388 (1989)]. The use of lipofection to introduce exogenous genes into the specific organs in vivo has certain practical advantages. Molecular targeting of liposomes to specific cells represents one area of benefit. Lipids may be chemically coupled to other molecules for the purpose of targeting [see Mackey, et. al., 1988, supra]. Targeted peptides, e.g., hormones or neurotransmitters, and proteins such as antibodies, or non-peptide molecules could be coupled to liposomes chemically.

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the TID-1 (or EAF1) inserted in the vector. That is, a specific expression vector of the present invention can be used in gene therapy.

Such an expression vector is particularly useful to regulate expression of a therapeutic TID-1 gene, for example, which can be used to stimulate apoptosis in a cancer cell, preferably a prostate cancer cell. In one embodiment, the present invention contemplates constitutive expression of the TID-1 gene, even if at low levels. In general, see U.S. Pat. No. 5,399,346 to Anderson et al.

In a further embodiment, the present invention provides for co-expression of TID-1 and calreticulin, and EAF1, and/or a calreticulin enhancing gene under control of a specific DNA recognition sequence by providing a gene therapy expression vector comprising a TID-1 coding gene, and a calreticulin coding gene, an EAF1 coding gene and/or a calreticulin enhancing gene under control of, inter alia, a TID-1 regulatory sequence. In a preferred embodiment, the TID-1, calreticulin, EAF1, and/or the calreticulin enhancing gene are provided on separate vectors.

Transgenic Animals, Gene Targeting, Antisense, and Ribozymes

The functional activity of TID-1, or derivative thereof, or structural/functional domain thereof, or alternatively a TID-1 homologue such as EAF1 or fragment thereof can be evaluated transgenically. In this respect, a transgenic animal model can be used. For example the TID-1 gene can be used in complementation studies employing transgenic mice. Transgenic vectors, including viral vectors, or cosmid clones (or phage clones) corresponding to the wild type locus of candidate gene, can be constructed using the isolated TID-1 gene. Cosmids may be introduced into transgenic mice using published procedures [Jaenisch, *Science*, 240:1468–1474 (1988)].

Thus the present invention further provides transgenic, knockin, and knockout TID-1 (or EAF1) animals. These can be used as animal models in drug screening assays for drugs that can treat cancer, e.g., prostate cancer. In a preferred embodiment the transgenic, knockin, or knockout animal is a mouse. The present invention also provides methods of using the transgenic, knockin, and knockout animals of the present invention in drug assays and screens. The cells from the knockout, knockin and/or transgenic animals of the present invention and cells that are constructed to contain a disrupted TID-1 (or EAF1) allele (or alleles) of the present invention or alternatively, to over express human TID-1 (or human EAF1), e.g., due to multiple copies of the corresponding gene, are also part of the present invention. These cells can also be used in the drug assays described below.

For example, in a particular embodiment an agent is administered to a TID-1 knockout mouse having a specific phenotype due to the expression of the TID-1, e.g., having prostate cells particularly susceptible to becoming cancerous (i.e., the knockout animal being susceptible to developing prostate cancer). The effect of the agent on the phenotype is then determined. An agent that modifies the specific phenotype is then selected. Agents can thus be identified which can counteract the loss of the TID-1 transcription factor, i.e., prevent and/or retard prostate cancer development and/or progression. Alternatively, an agent can be administered to a knockin, knockout, or transgenic animal, but the assay can be performed in situ or in vitro, e.g., determining the progression of the cancer in a prostate cell obtained from the knockout animal.

A transgenic or knockin animal can thus be prepared that expresses a recombinant TID-1 or a fragment thereof (or EAF1 or fragment thereof). In a particular embodiment, the transgenic or knockin animal expresses the human TID-1 (hTID-1). Such transgenic animals can be obtained through gene therapy techniques described above or by microinjection of a nucleic acid [such as a bacterial artificial chromosome (BAC) that encodes a TID-1] for example, into an embryonic stem cell or an animal zygote. Microinjection of BACs has been shown to be successful in a number of animals including rats, rabbits, pigs, goats, sheep, and cows [in *Transgenic Animals Generation and Use ed.*, L. M. Houdebine, Harwood Academic Publishers, The Netherlands (1997)]. Methods of constructing BACs [or other DNAs such as bacteriophage P1 derived artificial chromosomes (PACs)] that encode specific nucleic acids through homologous recombination have recently been described in great detail [Heintz et al., PCT/US98/12966, (1998) the contents of which are hereby incorporated by reference in its entirety]. Alternatively, a yeast artificial chromosome (YAC) that encodes a TID-1 can be used. In a preferred embodiment the transgenic animal is a mouse.

Alternatively, an animal model can be prepared in which expression of the TID-1 (or EAF1) gene is disrupted. Gene expression is disrupted, according to the invention, when no functional protein is expressed. One standard method to evaluate the phenotypic effect of a gene product is to employ knock-out technology to delete a gene as described in U.S. Pat. No. 5,464,764, Issued Nov. 7, 1995; and U.S. Pat. No. 5,777,195, Issued Jul. 7, 1998 (the contents of both of which are hereby incorporated by reference in their entireties.)

In yet another aspect of the invention a knockin animal is made. A knockin animal can be prepared in an analogous manner as a knockout animal except a variant/modified exon or gene is substituted for the exon or gene of interest through homologous recombination rather than disrupting the gene. Thus, knockout, knockin and transgenic animals can be prepared with the nucleic acids encoding the TID-1 (or EAF1) proteins of the present invention.

The present invention also extends to the preparation of anti sense nucleotides and ribozymes that may be used to interfere with the expression of TID-1 (or EAF1) at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15:5749–5763 (1987); Marcus-Sekura *Anal. Biochem.,* 172:289–295 (1988); Brysch et al., *Cell Mol. Neurobiol.,* 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient, though larger molecules that are essentially complementary to the entire mRNA are more likely to be effective. Antisense methods have been used to inhibit the expression of many genes in vitro [Marcus-Sekura, *Anal. Biochem.,* 172:289–295 (1988); Hambor et al., *Proc. Natl. Acad. Sci. U.S.A.* 85:4010–4014 (1988)] and in situ [Arima et al., *Antisense Nucl. Acid Drug Dev.* 8:319–327 (1998); Hou et al., *Antisense Nucl. Acid Drug Dev.* 8:295–308 (1998); U.S. Pat. No. 5,726,020, Issued Mar. 10, 1998; and U.S. Pat. No. 5,731,294, Issued Mar. 24, 1998, all of which are incorporated by reference in their entireties].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, *JAMA,* 260:3030–3034 (1988); Cech, *Biochem. Intl,* 18:7–14 (1989)]. Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules that bind mRNAs that encode TID-1 (or EAF1), and ribozymes that cleave mRNAs that encode TID-1 (or EAF1).

Kits

In a further embodiment of this invention, commercial test kits suitable for use by a medical specialist may be prepared to determine the presence or absence of either TID-1 or calreticulin in suspected target prostate cells. In accordance with the testing techniques discussed above, one class of such kits will contain at least the labeled TID-1 (or calreticulin) and/or a binding partner, for instance antibodies specific thereto. The kit also preferably contains directions for protocols that depend upon the method selected, e.g., "competitive", "sandwich", "DASP", and the like. In an alternative kit, a labeled nucleotide probe is included that is specific for TID-1 (or calreticulin). The kits of the present invention may also contain peripheral reagents such as buffers, stabilizers, etc.

Drug Screens

In addition to rational design of agonists and antagonists based on the structure of TID-1 and/or EAF1, and in particular the structure of the apoptosis inducing domain (e.g., amino acid residues 68–113 of SEQ ID NO:18), the present invention further contemplates alternative methods for identifying specific antagonists or agonists using various screening assays known in the art. In a particular embodiment, the present invention provides methods of identifying compounds that modulate the effectiveness of TID-1 to induce cellular apoptosis and/or to act as a transcription factor. In another embodiment, the present invention provides methods of identifying compounds that modulate the expression of the TID-1 or EAF1 transcript.

Accordingly any screening technique known in the art can be used to screen for agonists or antagonists to TID-1 and/or EAF1 activity including to those that effect the expression one or both of these proteins. Thus, the present invention contemplates screens for small molecule ligands or ligand analogs and mimics, as well as screens for natural ligands that bind to and agonize or antagonize TID-1 and/or EAF1 in vivo. For example, natural products libraries can be screened using assays of the invention for molecules that agonize or antagonize TID-1 activity. In a particular embodiment, the drug screen is performed with a mammalian cell that comprises a TID-1.

Knowledge of the primary sequence of the TID-1 or EAF1 protein and the similarity of domains present in these proteins as well as with those comprised other proteins, can also provide clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, *Science* 249:386–390 (1990); Cwirla, et al., *Proc. Natl. Acad. Sci.*, 87:6378–6382 (1990); Devlin et al., *Science,* 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume* 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–10704 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in their entireties], and the like can be used to screen for binding partners/ligands to the TID-1 and/or the EAF1 protein according to the present invention. In addition, a library of chemicals as are commercially available from most large chemical companies including Merck, GlaxoSmithKline, Bristol Meyers Squib, Monsanto/Searle, Eli Lilly, Aventis and Pharmacia UpJohn, can be screened including via high throughput screening. Alternatively potential drugs may be synthesized de novo.

Assays for binding of soluble ligand to TID-1 and/or EAF1 in cells that express TID-1 and/or EAF1 protein (or extracts thereof) can be performed. The soluble ligands can be provided readily as recombinant or synthetic polypeptides for example. Alternatively, small organic molecules or phage peptides can be used in the assays.

The screening can be performed with recombinant cells (or extracts thereof) that express a TID-1 protein, or fragment thereof, for example. Alternatively, the screening can be performed using purified protein, e.g., produced recombinantly, as described above. The ability of the labeled, soluble or solubilized TID-1 or EAF1 protein to act as a transcription factor in a cell (e.g., a prostate cell) can be determined. In either case, such assays can be used to screen libraries, as described in the foregoing references and below.

In one such example, a phage library can be employed as the source of potential modulators. Phage libraries have been constructed which when infected into host *E. coli* produce random peptide sequences of approximately 10 to 15 amino acids [Parmley and Smith, *Gene,* 73:305–318 (1988), Scott and Smith, *Science,* 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive TID-1 protein or fragment thereof. After a specified incubation period, the filters can be thoroughly washed and developed for autoradiography. Plaques containing the phage that bind to the radioactive to the TID-1 protein can then be identified. These phages can be further cloned and then retested for their ability to enhance the effect of the TID-1 protein, for example. Once the phages have been purified, the binding sequence contained within the phage can be determined by standard DNA sequencing techniques. Once the DNA sequence is known, synthetic peptides can be generated which represents these sequences. These peptides can be re-tested, for example, for their ability to enhance the effect of TID-1 to stimulate apoptosis in a cancerous cell.

The effective peptide(s) can be synthesized in large quantities for use in in vivo models and eventually in humans to stimulate apoptosis. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine*, 10:175–178 (1990)].

An in situ assay useful and contemplated in accordance with the present invention is known as a "cis/trans" assay. Briefly, this assay employs two genetic constructs, one of which is typically a plasmid that continually expresses a particular receptor that is transfected into an appropriate cell line, and the second of which is a plasmid that expresses a reporter such as luciferase or green fluorescent protein, under the control of the receptor. As disclosed herein, TID-1 binds to DNA in a sequence-specific fashion, i.e., DNA comprising the response element, ACTTTA. Thus, one plasmid is a construct that results in expression of the receptor in the chosen cell line, while the second plasmid possesses a promoter comprising the luciferase gene in which the response element ACTTTA is inserted. If the compound being tested interferes with the receptor-response element pair, transcription of the luciferase gene will be decreased. In the compound enhances the effect of the transcription factor, transcription of the luciferase gene will be increased. The resulting chemiluminescence due to luciferase can be measured photometrically. A variation of the foregoing protocol is described in detail in U.S. Pat. No. 4,981,784 and PCT International Publication No. WO 88/03168.

Administration

According to the invention, the component or components of a therapeutic composition, e.g., a TID-1 protein or a TID-1 protein modulator (such as a drug identified by the drug screening methods of the present invention), or a TID-1 mimic, or structural/functional domain of TID-1, or alternatively a TID-1 homologue such as EAF1 or fragment thereof and a pharmaceutically acceptable carrier, of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Such administration is preferably performed in the treatment of cancer, including epithelium-derived carcinomas, kidney cancers, lymphomas, leukemias, and particularly, prostate cancer.

In a preferred aspect, a TID-1 or EAF1 protein of the present invention or fragments thereof can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to a TID-1 protein or a EAF1 protein of the present invention or fragments thereof. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the TID-1 protein via the reduced sulfhydryl.

Antibodies for use as targeting molecule are specific for cell surface antigen. In one embodiment, the antigen is a receptor. For example, an antibody specific for a receptor on T lymphocyte receptor, can be used in the treatment of lymphoma and/or prostate cancer. This invention further provides for the use of other targeting molecules, such as lectins, carbohydrates, proteins and steroids.

In another embodiment, the therapeutic compound can be delivered in a vesicle, in particular a liposome [see Langer, *Science*, 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, *ibid.*, pp. 317–327; see generally *ibid.*]. To reduce its systemic side effects, this may be a preferred method for introducing a TID-1 protein.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. Nos. 5,164,189 (supra), 5,008,110 (supra), and 4,879, 119, issued Nov. 7, 1989 to Aruga et al., the disclosure of each of which is incorporated herein by reference in its entirety.

Pharmaceutical Compositions. In yet another aspect of the present invention, pharmaceutical compositions of the above are provided. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435–1712 which are herein incorporated by reference. The compositions may be prepared in liquid form, or may be in dried powder, such as lyophilized form.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

A subject in whom administration of TID-1, EAF1, or N-terminal fragments thereof (e.g., amino acids 68–113 of SEQ ID NO:18) is an effective therapeutic regiment is preferably a human, but can be any animal. Thus, as can be readily appreciated by one of ordinary skill in the art, the methods and pharmaceutical compositions of the present invention are particularly suited to administration to any animal, i.e., for veterinary medical use, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden including primates and apes), research animals, such as mice, rats, rabbits, goats, sheep, pigs, dogs, cats, etc., avian species, such as chickens, turkeys, songbirds, etc.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Escape From Androgen-Dependent Growth Restriction, Via Calreticulin Down-Regulation Is an Essential Step In Prostate Cancer Progression Introduction Recent research on androgen-response gene expression programs using the rat ventral prostate model has led to the identification of 25 genes that are up-regulated by androgen and 4 genes that are down-regulated by androgen in the prostate [Wang et. al., Proc. Natl. Acad. Sci. 94:12999–13004 (1997), the contents of which is hereby incorporated by reference in its entirety]. One such gene product identified, calreticulin, is an androgen-response gene that is most abundantly synthesized in the prostate. In the prostate the level of the calreticulin protein is controlled by androgen in the prostate [Wang et. al., Proc. Natl. Acad. Sci. 94:12999–13004 (1997); Zhu et al. Endocrinology 139:4337–4344 (1998)]. Heretofore, the role of calreticulin in prostate malignancies was not known.

Methods

Identification of androgen-response genes: Androgen-response genes are identified on the basis of their induction during the initial regrowth of the regressed ventral prostate in 7-day castrated rats using a highly sensitive PCR-based cDNA subtraction method [Wang and Brown Proc. Natl. Acad. Sci. 88:11505–11509 (1991) and Wang et. al., Proc. Natl. Acad. Sci. 94:12999–13004 (1997), the contents of each are hereby incorporated by reference in their entireties].

Tissue collection: Prostate cancer tissue specimens are obtained from patients undergoing transurethral resection or radical prostatectomy. Ongoing accrual of approximately 5 cancer specimens per month is sufficient. This accrual supplements a total of 80 specimens already collected and used in previously published work. For each specimen obtained clinical stage, serum prostate specific antigen (PSA), and history of prior chemotherapy, radiation therapy or hormonal therapy are recorded. Tumor specimens from radical prostatectomy are sectioned, processed and fixed per routine protocol for histopathologic examination. Preferably, each specimen is reviewed to identify representative sections of (1) intraprostatic tumor, (2) zone homologous benign prostate tissue, and (3) any areas of extraprostatic extension or seminal vesicle invasion. In those few cases where lymph node metastases are identified either before or after radical prostatectomy is performed, representative sections of lymph node tumor are obtained in addition to the sections from the primary tumor.

Immunostaining: Calreticulin immunostaining is performed on sections of (1) intraprostatic tumor, (2) zone homologous benign prostate tissue, (3) any areas of extraprostatic extension or seminal vesicle invasion and any lymph node metastases. A semi-quantitative immunohistochemical method is used to assess the expression of calreticulin and PSA in clinical prostate cancer specimens and staining is scored by a blinded observer on the basis of ten randomly selected high-power fields. Loss of calreticulin expression is scored for each primary tumor specimen as compared to a zone homologous area of benign prostate tissue on the same section. For tumors which display significant heterogeneity in tumor grade, e.g., Gleason 5 and 3 [Kozlowski and Grayhack (1991)], further scoring can be performed to compare areas of high and low tumor grade. Finally, areas of extraprostatic extension and/or lymph node metastasis are scored in comparison to the primary tumor.

Analysis of the calreticulin expression in specimens from prostate patients: Calreticulin expression can be quantitated from clinical specimens from prostate cancer patients (e.g., approximately 100–200 patients or more is preferred for the study). The total number is then determined by the statistical power necessary to correlate tumor expression with tumor Gleason grade, extraprostatic invasion and hormonal status of the patient using standard statistical methods Results Androgen Controls Homeostasis of the Prostate: Table 1 demonstrates that androgen stimulates proliferation and differentiation in a regressed prostate, but not in a fully-grown prostate. On the other hand, androgen ablation induces massive apoptosis and rapid de-differentiation in a fully-grown prostate, but has little or no effect on a regressed prostate. These observations indicate that in the regrowth process of a regressed prostate androgen replacement:

(i) stimulates and then nullifies proliferation;
(ii) establishes apoptotic potential, while inhibiting apoptosis; and
(iii) induces and maintains differentiation.

TABLE 1

THE IMPACT OF ANDROGEN MANIPULATION ON THE REGRESSED PROSTATE AND THE NORMAL PROSTATE.

| ANDROGEN | REGRESSED PROSTATE | FULLY-GROWN PROSTATE |
| --- | --- | --- |
| plus | Proliferation & Differentiation | No Significant Change |
| minus | No Significant Change | Apoptosis & De-differentiation |

"plus" represents androgen replacement.
"minus" represents androgen ablation or administration of anti-androgens.
Differentiation is defined as the expression of prostate-specific markers.
De-differentiation is defined as loss of the expression of prostate-specific markers.

Androgen action is mediated through androgen-response genes including calreticulin: The dramatic influence of androgen on the prostate is mediated through the ligand-dependent transcription factor "AR" which regulates the expression of androgen-response genes, either directly or indirectly [Mainwaring et al., "The Mechanism of Action of Androgen" in Monographs on Endocrinology, Vol. 10, New York: Springer Verlag (1977); Zhou et al., Recent Progress in Hormone Research 49:249–274 (1994)]. Thus, androgen-response genes mediate AR downstream events leading to cellular and morphological changes in the prostate during androgen manipulation.

To study the androgen action pathway, androgen-response genes were identified on the basis of their induction during the initial regrowth of the regressed ventral prostate in 7-day castrated rats using a highly sensitive PCR-based cDNA subtraction method [see methods above]. The search identified 25 genes that are up-regulated by androgen and 4 genes that are down-regulated by androgen in the ventral prostate of a 7-day castrated rat. One of the androgen-response genes encodes calreticulin [Zhu et al., Endocrinology 139:4337–4344 (1998)]. Calreticulin has a significant growth suppressive role in prostate cancer and its expression is down-regulated in prostate cancer cells. These observations indicate that at least one part of the androgen action pathway that is growth suppressive is down-regulated in prostate cancer pathogenesis.

Calreticulin is abundantly expressed and regulated by androgen in the prostate. Calreticulin was identified in a screen for androgen-response genes from rat ventral prostate using a PCR-based cDNA subtraction method [Wang et. al., Proc. Natl. Acad. Sci. 94:12999–13004 (1997), the contents of which is hereby incorporated by reference in its entirety]. The level of calreticulin expression in the rat prostate is more abundant than any of the other surveyed organs (FIG. 1) [Zhu et al. Endocrinology 139:4337–4344 (1998)]. The expression of calreticulin in the dorsal and lateral prostates of the rat is also abundant and regulated by androgen. Western blot analysis showed that the calreticulin protein in the prostate is also regulated during androgen manipulation. In situ hybridization and immunohistochemistry (IHC) showed that calreticulin is an intracellular protein in the epithelial cells of the prostate.

Furthermore, androgen regulates the expression of calreticulin in the mouse prostate and in cultured human BPH tissue. Also, calreticulin expression is regulated by androgen in LNCaP, an androgen-sensitive human prostate cancer cell line. These observations indicate that androgen regulation of calreticulin expression is conserved evolutionarily.

Calreticulin expression is down-regulated in clinical prostate cancer specimens. Expression of calreticulin in 21 clinical prostate specimens from radical prostatectomy was examined by immunohistochemistry using an anti-calreticulin antibody [Zhu et al., Endocrinology 139:4337–4344 (1998)]. These specimens contain benign regions, tumors, and/or high grade prostatic intraepithelial neoplasia (HGPIN). Calreticulin expression was down-regulated, to various extents, in 4 out of 11 HGPINs, 4 out of 10 Gleason 3(+)3 prostate tumors, and 2 out of 3 Gleason 4(+)4 prostate tumors. Examples of typical down-regulation are shown in FIGS. 2A–2D. No calreticulin down-regulation was observed in benign epithelial cells. These observations indicate that calreticulin down-regulation is more frequent in tumors with a high Gleason score, which is associated with poor prognosis [Gleason et al., J. Urol. 111:58–64 (1974)].

Figure 3:
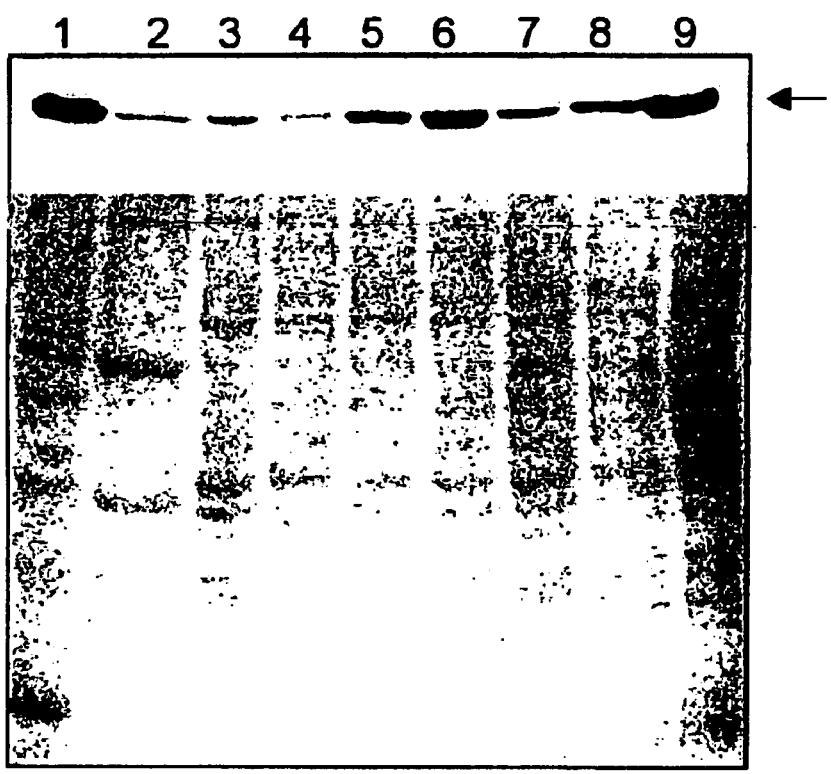
FIG. 3 depicts a Western blot monitoring the expression of calreticulin in parental, empty vector transfected, and pcDNA3.1/crt transfected PC3 and LNCaP cells. Lane 1 is the Normal rat ventral prostate; Lane 2 is the 7-day castrated rat ventral prostate; Lane 3 is the Parental PC3; Lane 4 is the Empty vector transfected PC3 (Mock); Lane 5 is the pcDNA3.1/crt transfected PC3 clone 35 (Crt35); Lane 6 is the pcDNA3.1/crt transfected PC3 clone 59 (Crt59); Lane 7 is the Parental LNCaP; Lane 8 is the Empty vector transfected LNCaP; and Lane 9 is the pcDNA3.1/crt transfected LNCaP. The arrow indicates calreticulin. The loading of total protein was visualized by Ponceau-S staining. The Western blot represents one example of 4 experiments.
Figure 4A:
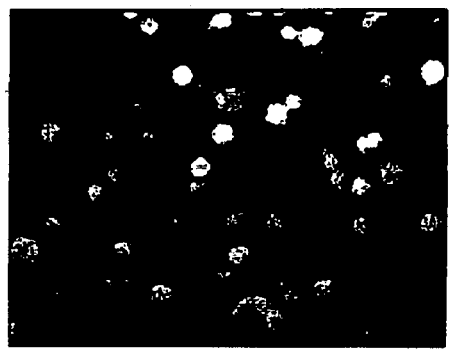
FIGS. 4A–4D show the effect of calreticulin overexpression on colony formation of PC3 cells in a soft agar assay, PC3 (FIG. 4A), Mock (FIG. 4B), Crt 35 (FIG. 4C) and Crt 59 (FIG. 4). The soft agar assay was conducted in 6-well plates. The bottom agar is 2 ml 0.6% noble agar containing 1×RPMI 1640 medium supplemented with 10% fetal bovine serum (FBS). After the preparation of bottom agar, 1 ml of 0.3% top agar containing 5,000 cells and 1×RPMI 1640 medium supplemented with 10% FBS was added to form the top layer. The assay for each PC3 subline was carried out in duplicate and was repeated at least 3 times.
Figure 4B:
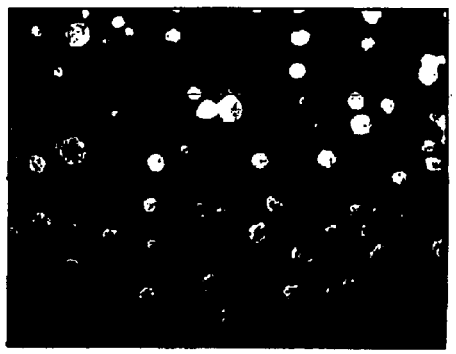
Figure 4C:
Figure 4D:
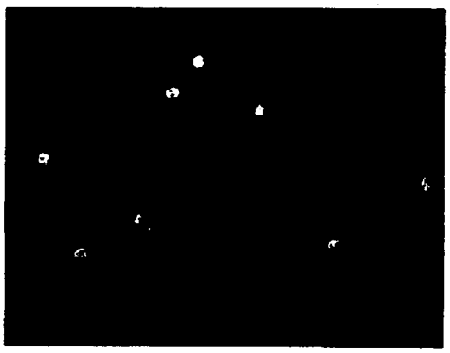

Calreticulin markedly inhibits anchorage-independent growth of prostate cancer cells in soft agar. Calreticulin cDNA was cloned into the pcDNA3.1/Hygro(((+))) vector (Invitrogen) to generate the calreticulin (crt) expression vector pcDNA3.1/crt. The pcDNA3.1/crt was then stably transfected into PC3, a highly aggressive androgen-independent human prostate cancer cell line. The endogenous calreticulin level for the PC3 clones transfected with an empty vector were essentially identical to the levels found for the parental cells (FIG. 3). However, PC3 cells that were transfected with pcDNA3.1/crt expressed calreticulin at varying levels (2.5–10×) above the endogenous calreticulin level of the parental cell line. The highest calreticulin expression levels achieved in PC3 cells are similar to the calreticulin level in the intact rat ventral prostate and the calreticulin level in the intact rat ventral prostate represents a physiologically relevant level (FIGS. 4A–4D).

Figure 5:
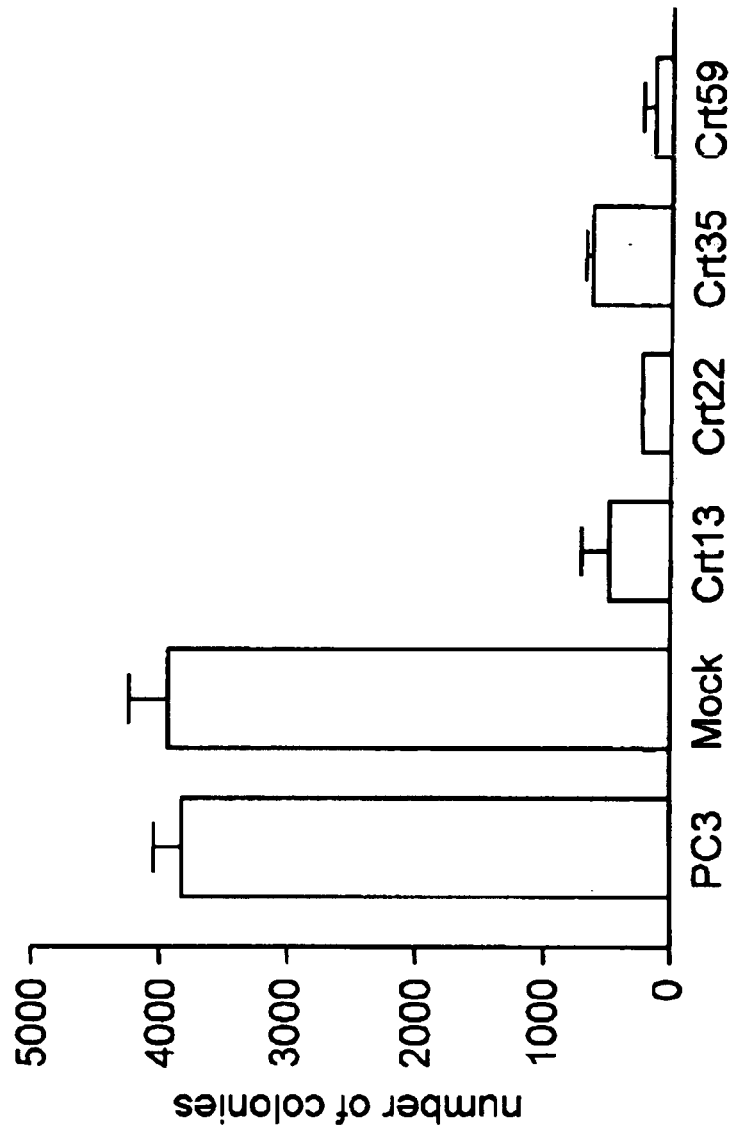
FIG. 5 shows the quantification of colony formation for PC3, Mock, Crt13, Crt22, Crt35 and Crt59. Colonies with greater than 125 um in diameter were counted in the quantification. Error bars represent standard error means (SEM).

Overexpression of calreticulin significantly inhibited the size and number of the PC3 colonies in soft agar assay (FIGS. 4A–4D and 5). Dramatic inhibition of soft agar colony formation was reproducibly observed in all four PC3 sublines which overexpressed calreticulin. Clones Crt59 and Crt35 express calreticulin at a level about 10-fold and 2.5-fold above the endogenous level respectively. Clone Crt13 and Crt22 express calreticulin about 5-fold above endogenous level. The degree of colony inhibition appears to correlate with the level of calreticulin overexpression in the four PC3 sublines. FIGS. 4A–4D and 5 show that clone Crt59 (10×endogenous) forms less colonies in soft agar than that in clone Crt35 (2.5×endogenous). Colony formation in clone Crt13 and Crt22 (5×endogous) is in-between clones Crt59 and Crt35 (FIG. 5).

As expected, overexpression of calreticulin also markedly inhibited anchorage-independent growth of TSU prostate cancer cells (TSU is an androgen-insensitive human prostate cancer cell line). This shows that calreticulin inhibition of anchorage-independent growth is a general phenomenon in prostate cancer cells. Anchorage-independent growth in soft agar correlates with the metastatic potential of cancer cells [Cifone and Fidler, Proc. Nat. Acad. Sci. USA, 77:1039–43 (1980)]. Thus, this observation indicates that calreticulin has the potential to suppress the metastasis of prostate cancer cells.

The transfection of pcDNA3.1/crt into LNCaP cells was also performed. The overexpression of calreticulin achieved in the stably transfected LNCaP cells is similar to that in the intact rat ventral prostate (FIG. 3). Since LNCaP cells have a very weak ability to grow in soft agar, it was not feasible to test the inhibition of their growth in soft agar by calreticulin overexpression.

The effect of calreticulin on other cellular functions have also been studied. Experimental results show that calreticulin overexpression inhibits prostate cancer cell proliferation, enhances cell attachment, and inhibits $Ca^{((+))((+))}$ ionophore-induced apoptosis.

The results provided above indicate that the loss of calreticulin expression is more frequent in high Gleason grade prostate tumors than in clinical prostate cancer specimens. Calreticulin expression can therefore be characterized in clinical specimens of human prostate cancer to correlate this expression with the regional heterogeneity of the tumor. This further demonstrates that the loss of calreticulin expression is associated with higher tumor grade, extraprostatic invasion, and metastasis, and that loss of calreticulin expression can make prostate cancer cells highly aggressive and life-threatening.

Example 2

Determination of the Functional Domains and/or Motifs of Calreticulin Required to Inhibit Anchorage-independent Growth Introduction Calreticulin is a multi-functional $Ca^{((+))((+))}$binding protein of the endoplasmic reticulum (ER) that has been evolutionarily conserved [Krause and Michalak, *Calreticulin. Cell.,* 88: 439–43 (1977); Michalak et al., *Bio. J.,* 285:681–92 (1992); and Sontheimer et al., *J. Inv. Med.,* 43:362–70 (1995)]. Calreticulin has been implicated in the regulation of a variety of cellular functions including the regulation of intracellular $Ca^{((+))((+))}$ homeostasis [Bastianutto et al., *J. Cell. Bio.,* 130:847–55 (1995); Liu et al., *J. Bio. Chem.,* 269:28635–9 (1994); Mery et al., *J. Bio. Chem.,* 271:9332–9 (1996); and Zhu and Wang, *Can. Res.* 59:1896–1902 (1999)], cell adhesion [Cappolino et al., *J. Bio. Chem.,* 270: 23132–8 (1995); Dedhar, *Trends Bio. Sci.,* 19:269–71 (1994); Dedhar et al., *Nature,* 367:480–3 (1994); Fadel et al., *J. Bio. Chem.,* 274: 15085–94 (1999); and Opas et al., *J. Cell. Bio.,* 135:1913–23 (1996); ], steroid-mediated gene regulation [Burns et al., *Nature,* 367: 476–80 (1994); Dedhar, *Trends Bio. Sci.,* 19:269–71 (1994); Dedhar et al., *Nature,* 367:480–3 (1994); and Michalak, et al., *J. Bio. Chem.,* 271:29436–45 (1996)], chaperone activity [Nauseef et al., *J. Bio. Chem.,* 270:4741–7 (1995); Peterson et al., *Mol. Bio. Cell.,* 6: 1173–84 (1995); Vassilakos et al., *Biochemistry,* 37:3480–90 (1998); Zapun et al., *J. Bio. Chem.,* 273:6009–12 (1998)], $Zn^{((+))((+))}$ binding and rubella virus RNA binding.

Following post-translational processing to remove the N-terminal signal sequence calreticulin retains approximately 400 amino acid residues [Baksh and Michalak, In Calreticulin, Michalak, e. d.,(Austin, Tex.; R. G. Landers), pp. 11–30 (1996)]. The post-translational protein has a calculated molecular weight (MW) of 46 kilodaltons (kDa) and an apparent MW of 60 kDa as determined by SDS PAGE gel electrophoresis. Calreticulin also comprises a KDEL (SEQ ID NO:1) endoplasmic reticulum retention sequence at its C-terminal end. Calreticulin consists of at least 3 structural/functional domains as shown in the diagram below.

PEDWDE (SEQ ID NO:2) and is believed to be responsible for the high affinity (Kd=1.6 uM) and low capacity $Ca^{((+))}_{((+))}$ binding to calreticulin (1 mol $Ca^{((+))((+))}$/mol of protein). Repeat B consists of three repeats of amino acid residues GXWXPPXIXNPXYX (SEQ ID NO:3) and is predicted to have a rigid turn structure which separates the globular head of the protein from the acidic tail. The C-Terminal Domain comprises amino acid residues 286–397, and is highly acidic giving it a negative charge. The large stretch of negatively charged residues bind $Ca^{((+))((+}$ with a low affinity (Kd= 0.3–0.2 mM) and a high capacity (approximately 25 mols $Ca^{((+))((+))}$/mol protein). These high capacity, low affinity $Ca^{((+))((+))}$ binding sites have led to the suggestion that calreticulin is involved in luminal $Ca^{((+))((+))}$ storage. The C-Terminal Domain has the most divergent amino acid sequence of the three calreticulin domains.

Methods

Figure 6:
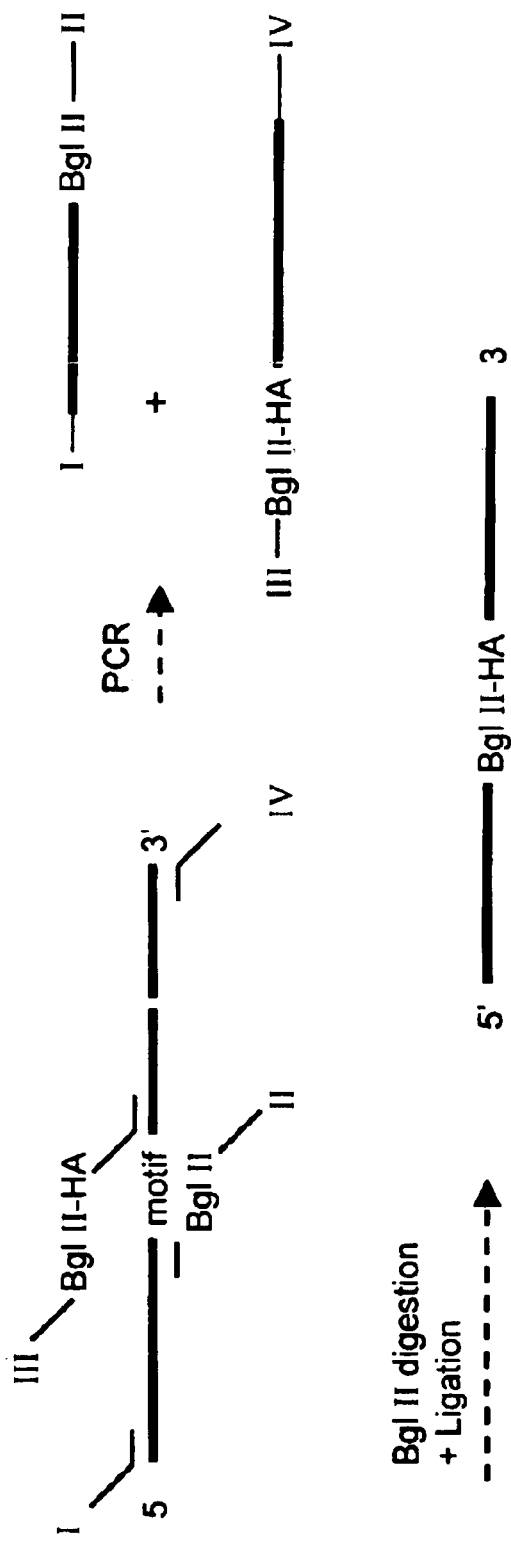
FIG. 6 shows the construction of substitution mutants for calreticulin at any motif. Four anchor PCR primers I, II, III, and IV are used for the construction of each substitution mutant. A Bgl II site is introduced into primer II and the HA tag sequence and a Bgl II site are introduced in primer III.

Preparation of HA-tagged wild-type and mutant calreticulins: Anchor PCR is used with calreticulin cDNA as the template. As shown in FIG. 6, two anchor PCR reactions are required to create a substitution mutant. The incorporation of BgII site permits the linkage of the two PCR products to create a full-length substitution mutant calreticulin. The calreticulin substitution mutant is cloned into the pcDNA3.1/Hygro(((+))) vector and the cloning orientation and substitution mutations are then verified by sequencing. The cytomegalovirus (CMV) promoter is used in pcDNA3.1/Hygro(((+))) to drive the expression of target genes, though other promoters can also be used including the simian virus 40 (SV40) promoter, the inducible metallothionein-1 promoter, the actin promoter, the elongation factor I promoter, or the herpes thymidine kinase promoter [Wagner et al., *Proc. Natl. Acad. Sci. U.S.A.* 78:1441–1445 (1981)].

| N-Terminal Domain 98–103  149–154 | Proline-rich Domain A       B | C-Terminal Domain |
|---|---|---|
| —   ----   ---- | ‖‖ | 000 KDEL |

"N-" is the N-terminal signal sequence which is cleaved after post-translational modification. As indicated, the N-Terminal Domain (N-Domain) contains the binding sites for integrin α and the steroid receptor. The Proline-rich Domain (P-Domain) comprises two triple repeats: "A", the triple repeat having a high binding affinity for a single mol of $Ca^{++}$, and "B", the triple repeat that provides the protein with a rigid turn structure. The third domain is the C-Terminal Domain (C-Domain) which has a long stretch of negative charge that binds multiple $Ca^{++}$ ions with a low binding affinity. The carboxyl-Terminal endoplasmic reticulum retention sequence "KDEL" is also shown in the diagram. The amino acid residues referred are from the amino acid sequence of SEQ ID NO:36.

Interestingly, though it does not bind to $Ca^{((+))((+))}$, the N-Terminal Domain is the most evolutionarily conserved domain of calreticulin [Baksh and Michalak, In Calreticulin, Michalak, e.d.,(Austin, Tex.; R. G. Landers), pp. 11–30 (1996)]. The N-Terminal Domain comprises amino acid residues 1–170 and is a globular structure having two regions of short α-helices at amino acid residues 98–103 and 149–154. These regions are responsible for binding to integrin α and the DNA binding domain of steroid receptors. The Proline-rich Domain comprises amino acid residues 171–285, and as its name implies, comprises a proline-rich region. The Proline-rich Domain contains two sets of repeats, i.e., Repeat A and Repeat B as shown in the schematic diagram of calreticulin, above. Repeat A consists of three repeats of amino acid residues PXXIXDPDAXK- The following HA-tagging wild-type and mutant calreticulins are constructed:

1) N-HA-KDEL, 2) P-HA-KDEL, 3) C-HA-KDEL,
4) N((+))P-HA-KDEL, 5) P((+))C-HA-KDEL, 6) N((+))C-HA-KDEL,
7) Calreticulin-HA-KDEL, and 8) Calreticulin-HA (ΔKDEL).

where, N, P, and C stand for the N-Domain, the P-Domain, and the C-Domain of calreticulin, respectively. These deletion mutants are cloned into the multiple cloning region of the vector pcDNA3.1/Hygro(((+))) (Invitrogen). The cloning strategy is undertaken in such a way that the expression vectors for various calreticulin domains are in the correct orientation. The vectors are then sequenced to verify that the coding region is in the correct orientation and in-frame for translation.

Stable transfection into PC3 cells: pcDNA3.1 vectors that express various calreticulin deletion or substitution mutants are transfected into PC3 cells as described in Example 1. At least three stably transfected PC3 sublines are used for each expression vector to minimize the clonal variations. Western blot analysis is used to determine the expression of ectopic HA-tagged calreticulin relative to endogenous calreticulin protein level.

Immunocytochemistry: Cellular localization of HA-tagged calreticulin and mutant calreticulin are determined by immunocytochemistry using an anti-HA antibody (e.g., Santa Cruz Biotechnology, cat# sc-805).

Soft agar assay: After the above characterization of various transfected PC3 cells, the ability of these cell lines to grow in soft agar is tested as described in Example 1. For each expression vector, three different stably transfected PC3 sublines are tested to reduce clonal variations. The controls performed in the soft agar assay include: cells that are transfected with full-length calreticulin with a HA-tag; cells that are transfected with an empty vector; and the parental PC3 cells.

In vivo studies: Each PC3 subline generated is injected into multiple male nude mice of 5–6 weeks old. For subcutaneous injection, a total of $1 \times 10^6$ PC3 cells in 20 ul of culture medium (RPMI-1640) is mixed with 20 ul of Matrigel prior and then injected into the anesthetized nude mice using a 30-gauge needle. PC3 tumors are rather aggressive and the xenograft tumors can reach the size of >100 mm$^3$ in 2–3 weeks. The tumor size is determined twice a week according to the following equation [Lim et al., Prostate, 22: 109–18 (1993)]:

$$\text{Volume} = L \times W \times H \times 0.5236$$

The advantage of subcutaneous injection is that the tumor can be monitored without sacrificing animals. Alternatively or in conjunction, orthotopic injection of PC3 cells in male nude mice can also be conducted. The animals are anesthetized and the operation is performed under sterile conditions. PC3 ($1 \times 10^6$) cells in 20 ul culture medium is mixed with 20 ul Matrigel and then injected using a 30-gauge needle into the dorsal prostate through a small ventral incision (~1.0 cm). The wound is closed with 6–0 sutures and the skin is closed with autoclips. Orthotopic implantation has the advantage of leading to reproducible formation of lymph node and lung metastases. In a particular embodiment, 144 male nude mice of 5–6 weeks old are used. In still a third embodiment, intravenous injection of tumor cells is performed. Intravenous injection is commonly used for assays of the metastatic potential of tumor cells [Li et al., J. Nat. Can. Inst., 81:1406–12 (1989); and Miyake et al., J. Urol., 160: 1562–1566 (1998)].

The size and the wet weight of primary tumors and the number of soft tissue metastasis are determined at about 4–5 weeks after the inoculation of PC3 tumors (lymph nod, lung, and liver) as described previously [Rembrink et al., Prostate, 31:168–74 (1997); and Sato et al., Can. Res., 57:1584–9 (1997)]. The tumors can be analyzed for apoptosis by the TUNEL assay [terminal deoxynucleotide transferase-mediated biotin-dUDP nick-end labeling (in situ staining for nuclear DNA fragmentation)], for proliferation by Ki-67 staining (Ki-67 is a nuclear antigen of proliferation), for calreticulin expression by immunohistochemistry, and/or by Western blotting using an anti-HA antibody and/or anti-calreticulin antibody. The ectopic expression of HA-tagged calreticulin in primary tumor and tumor metastases are determined by immunohistochemistry using anti-HA antibody.

The apoptotic index is defined as the percentage of apoptotic cells in 30 high-powered microscopic fields for each tissue section.

Results

Ectopic expression of calreticulin inhibits anchorage-independent growth of prostate cancer cells. The three domains and various protein motifs of calreticulin are examined to determine their individual roles in malignancy suppression. For example, the role of the KDEL ER-localization signal in the calreticulin-dependent inhibition of anchorage-independent growth is determined. In addition, the three domains of calreticulin, i.e., the N-Terminal domain, the Proline-rich domain, and the C-Terminal domain are individually examined to determine which are critical for the inhibition. Such determinations of functional domains and/or motifs provide important clues regarding the signaling pathway(s) involved in the suppression of anchorage-independent growth. Understanding this signaling pathway provides novel approaches for inhibiting anchorage-independent growth of prostate cancer cells.

Deletion mutagenesis: Deletion mutagenesis is therefore performed to determine which domain(s) in calreticulin are necessary and/or sufficient to inhibit anchorage-independent growth. As shown in the schematic diagram of the calreticulin protein above, calreticulin consists of an N-Domain, a P-Domain, and a C-Domain plus a KDEL endoplasmic reticulum retention signal. An hemagglutinin (HA) epitope can be added to various mutants, for example [Field et al., Mol. Cell. Bio., 8:2159–65 (1988); Zhou et al., Genes Dev., 6:1964–74 (1992)]. The addition of the epitope allows the detection of the ectopic calreticulin by an anti-HA antibody so as to distinguish the ectopic calreticulin from the endogenous calreticulin. The HA tag can be inserted between the C-Domain and the KDEL, for example. The N-terminus is not appropriate for tagging because the N-terminus comprises a signal sequence that is post-translationally removed. Furthermore, the KDEL endoplasmic reticulum retention signal is at the C-terminus. Therefore, the HA insertion is preferably inserted internally e.g., between the C-Domain and the KDEL sequence. The HA epitope is preferable because the epitope is small and does not interfere with the function of the tagged protein [Field et al., Mol. Cell. Bio., 8:2159–65 (1988); Zhou et al., Genes Dev., 6:1964–74 (1992)]. The HA tag comprises a 9-amino-acid sequence, YPYDVPDYA (SEQ ID NO:4). However, other tags such as a FLAG tag can also be used.

Various substitution mutants can be created by replacing the amino acid sequence with the HA epitope sequence (Table 2). The HA epitope is used to substitute for the indicated motifs so that the expression of substitution mutants can be easily detected and distinguished from the endogenous calreticulin. Anchor PCR is used with calreticulin cDNA as the template.

TABLE 2

| SUBSTITUTION MUTANTS CREATED WITH Bgl II-HA/IS-YPYDVPDYA | | |
|---|---|---|
| Name | SEQ ID NO: | Motif |
| Crt(S95-105HA) | 5 | CGGGYVKLFPG |
| Crt(S147-157HA) | 6 | INKDIRCKDDEF |

TABLE 2-continued

SUBSTITUTION MUTANTS CREATED WITH Bgl II-HA/
IS-YPYDVPDYA

| Name | SEQ ID NO: | Motif |
|---|---|---|
| Crt(S201-211HA) | 7 | PDAAKPEDWDE |
| Crt(S218-228HA) | 8 | PTDSKPEDWDK |
| Crt(S236-246HA) | 9 | PDAKKPEDWDE |
| Crt(S250-262HA) | 10 | GEWEPPVIQNPEY |
| Crt(S264-276HA) | 11 | GEWKPRQIDNPDY |
| Crt(S278-290HA) | 12 | GTWIHPEIDNPEY |

Substitution mutants: The locations of various motifs are shown in the diagram of calreticulin shown above.
(1) Crt(S95-105HA) and Crt(S147-157HA) are in the N-Domain and believed to interact with integrin α;
(2) Crt(S201-211HA), Crt(S218-228HA), and Crt(S236-246HA) are in the repeat A of the P-Domain;
(3) Crt(S250-262HA), Crt(S264-276HA), and Crt(S278-290HA) are in the repeat B in P-Domain.
The repeat consensus sequences are underlined.

The deletion mutagenesis reveals which domain(s) in calreticulin are sufficient for the suppression of prostate cancer growth in soft agar. The function of each of these motifs are then tested for suppression of anchorage-independent growth.

A series of pcDNA3.1 vectors that express HA-tagged calreticulin and calreticulin mutants are obtained which allow the importance of various calreticulin domains and motifs in suppression of anchorage-independent growth to be determined.

Since the N-Domain and the P-domain are evolutionarily conserved and these two domains are involved in integrin α binding, cell adhesion, and intracellular $Ca^{((+))((+))}$ signaling, substitutions in these domains are preferred.

The calreticulin-HA (ΔKDEL) is also a preferred embodiment since it is responsible for endoplasmic reticulum localization of calreticulin. The intracellular localization of calreticulin-HA (ΔKDEL) can also be determined by immunocytochemistry.

When a motif is essential for the suppression of anchorage-independent growth, the substitution mutants at this motif lose the ability to inhibit the growth of PC3 in soft agar. Such substitution mutants are further characterized for their function to regulate cell adhesion and/or intracellular $Ca^{((+))((+))}$ homeostasis.

As mentioned above, other fusion peptides and proteins can be used other than the HA-tag. For example, a FLAG-tag, or green fluorescent protein (GFP) or glutathione S-transferase (GST). Fusion with proteins such as GST or GFP should further stabilize the substitution mutants.

In a preferred embodiment, specific clones are identified that express calreticulin mutants at levels that are similar to the ectopic expression of wild-type calreticulin. A moderate up-regulation in calreticulin expression has been found to be sufficient to cause suppression of anchorage-independent growth of PC3 cells.

Study the role of calreticulin in prostate tumor growth and metastasis in vivo in tumor xenografts: Calreticulin ectopic expression inhibits anchorage-independent growth of prostate cancer cells and it is well established that anchorage-independent growth correlates with the malignancy of cancer cells, particularly with the metastatic potential [Cifone and Fidler, Proc. Nat. Acad. Sci. USA, 77:1039–43 (1980); and Li et al., J. Nat. Can. Inst., 81:1406–12 (1989)]. Therefore, calreticulin expression should inhibit the growth and/or metastasis of prostate cancer cells in vivo. This is demonstrated by generating PC3 xenograft tumors in nude mice [see for example, Rembrink et al., Prostate, 31:168–74 (1997); and Shevrin et al., Prostate, 15: 187–94 (1989)]. The PC3 sublines generated above are used to show that ectopic expression of calreticulin suppresses the growth and/or metastasis of PC3 xenograft tumors.

The following PC3 cell lines can be used:
(1) the PC3 parental line.
(2) PC3-vec1; PC3-vec2; and PC3-vec3: 3 different clones of PC3 cells transfected with vector pcDNA3.1.
(3) PC3-crt1; PC3-crt2; and PC3-crt3: 3 different clones of PC3 cells transfected with HA-tagged full-length calreticulin.
(4) PC3-X1, PC3-X2, and PC3-X3: 3 different clones of PC3 cells transfected with a calreticulin domain X (X=N, P, C, N((+))P, N((+))C, or P((+))C) that is just sufficient to inhibit anchorage-independent growth.
(5) PC3-M1, PC3-M2, and PC3-M3: 3 different clones of PC3 cells transfected with calreticulin substitution mutant at motif M that is unable to inhibit anchorage-independent growth.

Primary PC3 tumors grow rapidly and can form microscopic and macroscopic metastasis. Since the anchorage-independent growth correlates with metastatic potential, calreticulin overexpression should significantly reduce the metastasis of PC3 xenograft tumors. Similarly, PC3 sublines transfected with a calreticulin domain that is just sufficient to inhibit their growth in soft agar should also have a reduced ability to form metastatic tumors in nude mice. In contrast, PC3 sublines transfected with a calreticulin substitution mutant that is unable to inhibit anchorage-independent growth should have little or no alterations in their ability to form metastatic tumors in nude mice.

The size of the primary tumors with calreticulin overexpression should be smaller than that of the controls. The Ki-67 positive cells in tumors with calreticulin overexpression should be less abundant than that in control tumors because calreticulin overexpression inhibits cell proliferation in culture dishes. The apoptotic index in xenograft tumors with calreticulin overexpression should be the same as that in control tumors because calreticulin overexpression does not cause cell death in PC3 cell lines in culture dishes.

Example 3

Traits is a Novel Testosterone Regulated Apoptosis Inducer and Tumor Suppressor in Prostate Cancer Summary Androgens are intimately associated with prostate cancer progression. Androgen action is mediated through the androgen receptor (AR) that regulates androgen-response genes either directly or indirectly. The identification and characterization of TRAITS (also known as U19 and TID-1), a novel testosterone regulated apoptosis inducer and tumor suppressor, is disclosed herein. TRAITS is a conserved 29 kd nuclear protein expressed in many human tissues with the most abundant expression in the prostate, bone marrow, kidney and lymph node. TRAITS can bind to DNA in a sequence-specific fashion (ACTTTA) and contains a transactivation domain in C-terminal region, indicating that TRAITS is a novel transcription factor. Overexpression of TRAITS in all of the surveyed cell lines can induce programmed cell death, as marked by cell membrane blebbing, chromatin condensation and genomic DNA fragmentation. Deletion mutagenesis of TRAITS showed that the highly conserved N-terminal region is necessary and sufficient for apoptosis induction. Interestingly, inducible activation of TRAITS in xenograft prostate tumors markedly inhibits the tumor growth. Consistent with its tumor suppressive role, TRAITS expression is down-regulated in all of the prostate cancer cell lines as well as in 7 out of 8 clinical human prostate tumor specimens. The above observations suggest that TRAITS is a commonly down-regulated tumor suppressor in prostate carcinomas.

Methods

Proliferation assay: Cells were plated onto 6-well plates in triplicate at 50,000 cells/well and cultured in RPMI 1640 medium supplemented with 10% fetal bovine serum (FBS), and 1% penicillin/streptomycin. The cells were trypsinized and counted each day afterwards for a five-day time course. The data were plotted using the GraphPad Prism software. The error bars represent SEM and they are difficult to see when SEM is very small. The cell proliferation assay was repeated 3 times and the results were very reproducible.

Soft agar assay: The soft agar assay was conducted in 6-well plates. The bottom agar is 2 ml 0.6% noble agar containing 1×RPMI 1640 medium supplemented with 10% FBS. After the preparation of bottom agar, 1 ml of 0.3% top agar containing 5,000 cells and 1×RPMI 1640 medium supplemented with 10% FBS was added to form the top layer. The assay for each PC3 subline was carried out in duplicate and was repeated at least 3 times.

Cell lines and tissue samples: The LNCaP, PC3, DU145, TSU cell lines were obtained from ATCC (Manassas, Va.). Dunning tumor cell lines G, AT1, AT2, AT3.1, AT6.1, and MatLyLu were provided by Allen Gao (Univ. Pittsburgh, Pittsburgh). NIH3T3 was provided by Ali Shaw and Hela cells by David Klumpp (Northwestern University, Chicago). Human multiple tissue Northern blot membranes were purchased from Clontech. Human radical prostatectomy specimens were provided by Department of Pathology at Northwestern University.

5'-RACE & 3'-RACE and low stringency hybridization: The 3' region of mouse TRAITS cDNA was screened from a mouse cDNA library using rat TRAITS cDNA as probe for low stringency hybridization. The 5' RACE was performed for cloning the 5' region of mouse TRAITS cDNA using primers:

5'-GTTCAACTCCACCAGTCACAG-3'    SEQ ID NO:21,

5'-CGGTGACAAGTAGCATCAGC-3'     SEQ ID NO:22,

5'-CTGAAGTCCTGTACTGTGGC-3'     SEQ ID NO:23, and

5'-CACAACTACTCATCTGGTCC-3'     SEQ ID NO:24.

Similarly, the 5'-RACE and 3'-RACE were performed for cloning the full length of human TRAITS cDNA using primers:

5'-TGATACTGGAGGATGTCGGC-3'     SEQ ID NO:25,

5'-CACAACTACTCATCTGGTCC-3'     SEQ ID NO:26,

5'-GCTGGGGACATCTTATCTTC-3'     SEQ ID NO:27.

5'-CAGTGATTGTTGCTGCTGAG-3'     SEQ ID NO:28 and

5'-CTCAGCAGCAACATCACTGT-3      SEQ ID NO:29.

Vector constructions and mutagenesis: The cDNAs of rat and human TRAITS were cloned into pEGFP C1, pEGFP N3, PM and pIRES2-EGFP(Clontech) by PCR. Deletion mutagenesis of TRAITS were generated by PCR and cloned into above first three vectors. The plasmids containing ER™ domain were kindly provided by G. Evan (UCSF, San Francisco). ER™ domain was cut with BamHI/EcoRI and recloned into pEGFP-TRAITS to generate a tripartite fusion protein. All constructions were verified by sequencing and transfected using Lipofectamine (Gibco), Super Fect reagent (Qiagen) or Fugene 6 (Roche). In stable transfection, 500 µg/ml geneticin (G418) was used for selection of positive clones.

RBSS and EMSA: RBSS was performed as described [Martinez-Garcia et al., Science 288:859(2000)] with modification. Sixty base oligonucleotides of which the middle 12 bases consisted of random sequences:
5'-GTCTGTCTGGATCCGAGGTGAGTA-N12-ACGTCTTCCGAAGCTTACGTC GCG-3' SEQ ID NO:32 was synthesized. Two 20-base oligonucleotides were also synthesized as forward:

5'-GTCTGTCTGGATCCGAGGTG-3'    SEQ ID NO:30 and reverse:

5'-CGCGACGTAAGCTTCGGAAG-3'    SEQ ID NO:31 primers.

The stringency of RBSS was increased by increasing the amount of nonspecific competitor poly[dI-dC](Sigma) (50, 100, 200, 400 and 500 ng, from first to fifth cycles, respectively) and by decreasing the amount of protein (2, 2, 1, 1, and 1 µl of E. coli-purified GST-TRAITS fusion protein). After five rounds of selection, the retarded DNA was eluted using an ELUTRAP starter kit (Schleicher & Scheull) and amplified by PCR. PCR products were cloned into pGEM-T (Promega) for sequencing analysis. The sequences were aligned and the consensus sequence (T-box) identified.

Two oligonucleotides: T-wt: (5'-GTCTGTCTGGAT CCGAGGTGAGTACTGAC<u>T</u>TTACACACGTCTTCCGA AGCTTACGTCGCG-3' SEQ ID NO:33) and T-mut: (5'-GTCTGTCTGGATCCGAGGTGAGTACTGAC<u>G</u>TTACACACGTCTTCCGAAGCTTACGTCGCG-3' SEQ ID NO:34) were synthesized and amplified by PCR. T4 polynucleotide kinase (Promega) was used to label T-wt & T-mut by [$\gamma$-$^{32}$P] ATP (NEN). Recombinant GST-TRAITS fusion protein was incubated with 500 µg poly [dI-dC] and EMSA was performed according to the protocol provided by Gel Shift Assay System (Promega).

CAT reporter assays: CAT activities were assayed 24 hours after transfection. NIH3T3 cells were grown in 6-well plates and transfected using Superfect (Qiagen). For transient transfection, 2 µg of PM constructions, 2 µg of pSVβ-gal (internal control) and 2 µg of pG5CAT (Clontech) were used per well. The level of CAT protein in cell extracts was determined using a CAT ELASA kit (Roche) according to the manufacturer. Protein concentration was measured using a Dc protein Assay kit (Bio-Rad). β-Galactosidase activity was measured by incubating with ONPG (o-nitrophenyl-β-D-galactopyranoside) solution. Data are reported as means ±S.E.M. of two separate experiments performed in triplicate.

Cell death assays flow cytometry analysis: In flow cytometry analysis, cells cultured under the indicated conditions were harvested for staining with the TACS™ Annexin V-Biotin apoptosis detection kit (R & D systems). Propidium iodide was used for nuclei staining and Cy5 was conjugated to Annexin V-biotin. Apoptosis of Annexin V-positive cells was analyzed by FACS. Hoechst 33342 (Molecular Probes) was used for nuclear condensate staining and DNA fragmentation assay.

Tumor growth: To determine their tumorigenicity, AT6.1 cells were injected subcutaneously ($1 \times 10^5$ cells) into 4–6 week old male nu/nu mice (NCI). To test the effect of antagonist of estrogen, tamoxifen pellets (50 mg, 1 mg/per day release; Innovative Research) were subcutaneously implanted at the time of tumor cell injection. Tumor sizes were calculated using formula $V=\pi \times h (h^2 3a^2)/6$, $a=(L((+))W)/4$ (Nature, 405:354–359) and the Student's t-test (two-tailed) was performed to analyze statistical significance using the SPSS 10.0 software (SPSS Inc., Chicago, Ill.).

Antibody generation and immunohistochemistry: GST-TRAITS fusion protein was generated by cloning human TRAITS cDNA into pGEX-2T vector (Amersham-Pharmacia). Rabbit polyclonal antibodies were raised using the purified fusion protein (Spring Valley). The antibody was purified using GST-TRAITS fusion protein covalently linked to a HiTrap™ column (Amersham-Pharmacia). The purified antibody was used in immunostaining of human radical prostatectomy specimens with a Vectastain ABC kit (Vector). The stained slides were briefly count-stained with hematoxylin.

Results

Androgen action is mediated through the androgen receptor (AR), a ligand-dependent transcription factor that regulates the expression of androgen-regulated genes. To define the role of androgen-response genes in prostate cancer, more than 20 androgen-response genes have been identified herein using the rat ventral prostate model. One of the up-regulated genes, as disclosed herein, encodes TRAITS [also named U19; Wang, et al. *Proc. Natl. Acad. Sci. USA* 94:12999–13004 (1997) and TID-1].

Figure 7A:
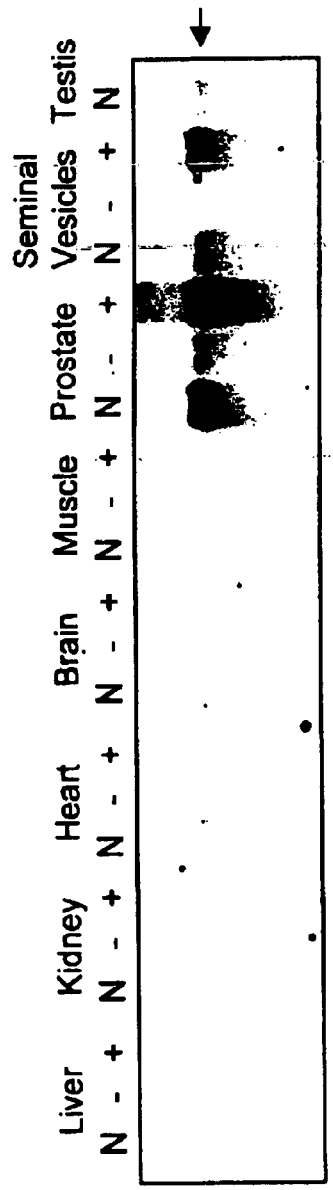
FIGS. 7A–7B are Northern blots for TID-1 expression in the rat during androgen manipulation. Indicated tissues were isolated from the normal testis-intact rat (N), the 7-day castrated rat (–), and the 7-day castrated rat followed by androgen replacement for 2 days (((+))). The TID-1 mRNA band in the top panel (FIG. 7A) is indicated by an arrow. The bottom panel (FIG. 7B) is the methylene blue staining of the total RNA after transfer.
Figure 7B:
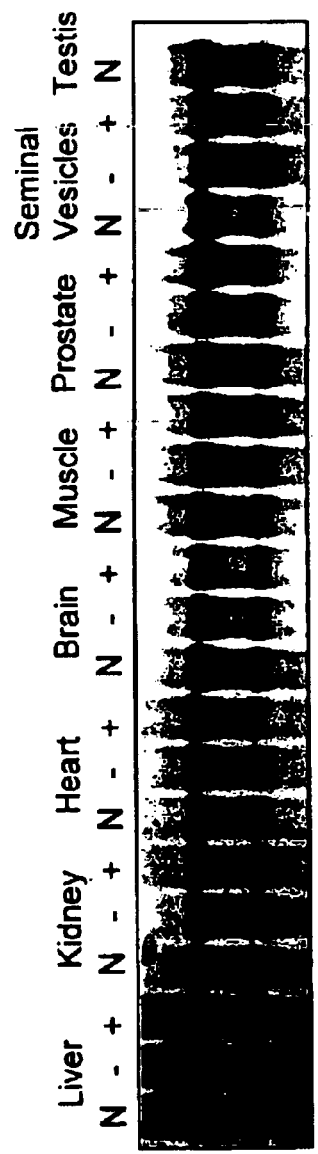

TRAITS is a transcription factor that can bind to DNA and contains a transactivation domain. FIGS. 7A–7B show that the expression of TRAITS is detected in the male sex accessory organs and testis. The expression of TRAITS in the prostate and seminal vesicles is regulated by androgen. Further study showed that TRAITS is expressed and regulated by androgen in all 3 lobes of the prostate and in the coagulating gland. These observations indicate that TRAITS is involved in androgen action in male sex accessory organs.

Figure 14B:
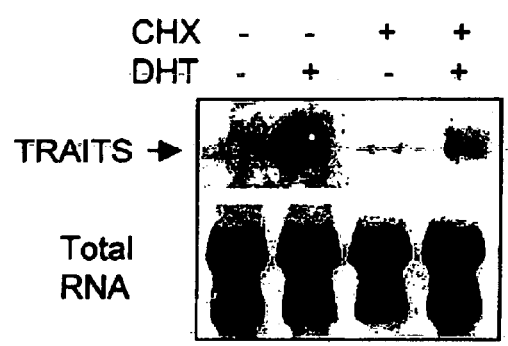

The TRAITS mRNA in LNCaP cells is regulated by androgen, indicating that androgenic regulation of TRAITS in prostatic cells is evolutionarily conserved (FIG. 14b). The androgen induction of TRAITS partially resists protein synthesis inhibition, suggesting that TRAITS is encoded by an early androgen-response gene in human prostatic epithelial cells.

Figure 14C:
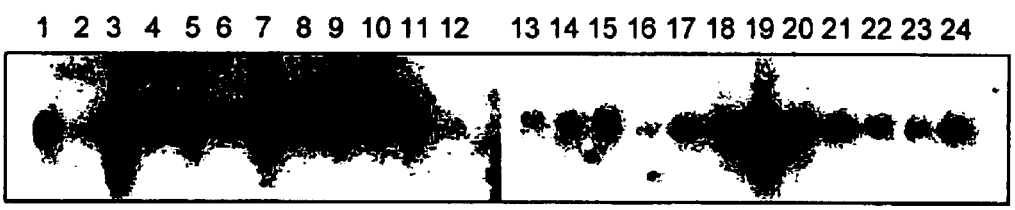

The tissue distribution of TRAITS expression in human was assessed using the human multiple tissue blots (CLONTECH) with the $\alpha^2$P-dCTP-labeled human TRAITS cDNA. The results showed that TRAITS is expressed in virtually every surveyed tissues with the most abundant expression in the prostate, bone marrow, kidney and lymph node (FIG. 14c). Thus, TRAITS may play important functions in many different tissues or organs.

TRAITS is conserved in evolution: A partial cDNA for mouse TRAITS was isolated from a cDNA library that was constructed using the normal mouse prostate mRNA. An initial database search using the protein sequence of TID-1 indicated that it did not share any homology with any known proteins and no recognizable motifs were identified in TID-1 (FIG. 8A). However, as described in Example 4, subsequent to the isolation of a protein with extensive homology to TRAITS (i.e., EAF1) the sequence for EAF1 appeared in the database.

TABLE 3

MAMMALIAN TRAITS

| SPECIES | TYPE | SEQ ID NO: |
|---|---|---|
| Rat | nucleic acid | 13 |
| Rat | amino acid | 14 |
| Mouse | nucleic acid | 15 |
| Mouse | amino acid | 16 |
| Human | nucleic acid | 17 |
| Human | amino acid | 18 |

The full-length cDNA of the rat TRAITS and the full-length cDNAs of the mouse and human TRAITS were cloned using low-stringency hybridization coupled with the 5'- and and 3'-RACE. As shown in FIG. 14a, both mouse and rat TRAITS proteins are 262 amino acids in length and share 91.6% amino-acid identity. Human TRAITS has a 3 amino acid deletion and 1 amino acid addition relative to the rodent TRAITS protein and it shares 79.4% and 80.2% amino acid identity with rat and mouse TRAITS, respectively. This indicates that the TRAITS gene is conserved and is also expressed in the human prostate. The N-terminal portion of the TRAITS (residues 1–113) is more conserved than its carboxy-terminal region. This portion of TRAITS contains the apoptosis-inducing domain. The N-terminal portions also share significant homology, about 40% identity, with putative proteins identified in *Caenorhabditis elegans, Drosophila melanogaster,* and *Arabidopsis thaliana.* A draft sequence of human chromosome 3 clone RP11-621020 (GeneBank accession number: AC078810) contains TRAITS, which showed TRAITS is composed of 6 exons.

Figure 18:
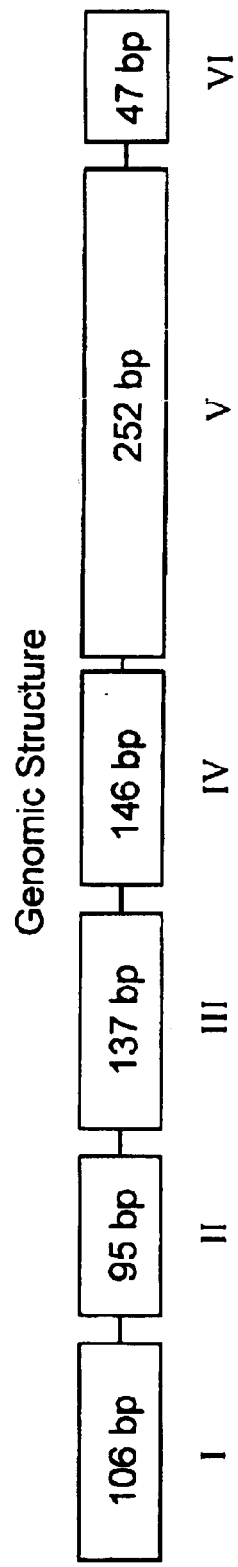
FIG. 18 depicts the genomic DNA structure of human TRAITS. Boxes indicate the exons, which are linked by the introns (lines): Exon I (71 bp 5'-UTR((+))106 bp); Exon II (95 bp); Exon III (137 bp); Exon IV (146 bp); Exon V (252 bp); and Exon VI (47+153 bp 3((+))-UTR). The gene is on human chromosome 3p. Exon III comprises the apoptosis-inducing domain, exon IV is the glutamine-rich region; and exon V is the serine rich region.

Genomic structure and mutagenesis of TRAITS: TRAITS is composed of six exons (FIG. 18) which in humans encode respectively, 35 amino acid residues, 32 amino acid residues, 46 amino acid residues, 48 amino acid residues, 85 amino acid residues, and 14 amino acid residues (see FIG. 14a for exon junctions). In an effort to determine the role of individual domains, domain mapping was performed by fusing nucleic acids encoding GFP to nucleic acids encoding fragments of the TRAITS in pEGFPN3 vectors. The vectors was then used for transient and stable transfection of PC3 cells. The ability of the various constructs to induce apoptosis was determined. In every case, exon III (corresponding to amino acids 68–113 of SEQ ID NO:18) was found to be both necessary and sufficient to induce apoptosis.

TRAITS is induced rapidly by androgen replacement in the regressed rat ventral prostate. The time course of TRAITS induction is the same as the induction of calreticulin and adrenomedullin, two primary androgen-response genes [Pewitt et al., *Endocrinology,* 140:2382–6 (1999); Zhu et al., *Endocrinology,* 139:4337–4344 (1998); and Zhu and Wang, *Can. Res.* 59:1896–1902 (1999)]. This indicates that TRAITS is also a primary androgen-response gene in the prostate.

Figure 7C:
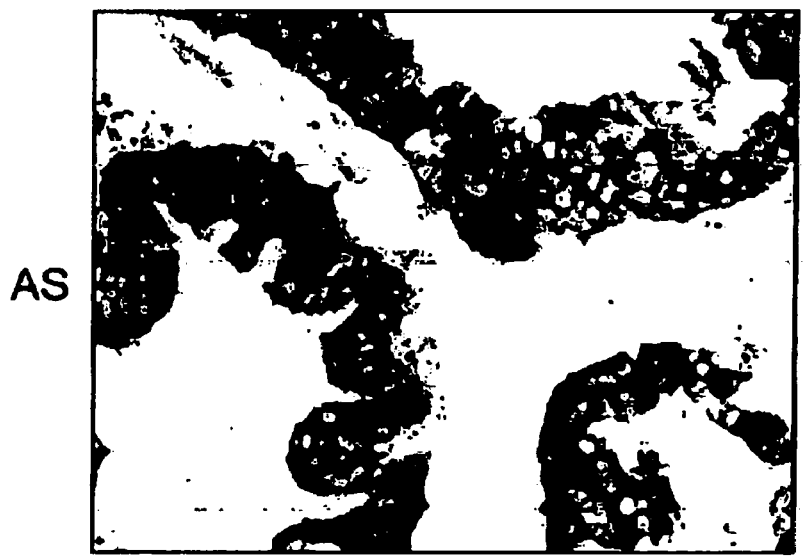
FIGS. 7C–7D show the in situ hybridization analysis of TID-1 expression in the normal rat ventral prostate. The serial sections of the ventral prostate were probed with antisense (AS) or sense(S) digoxygenin-labeled RNA probe.
Figure 7D:
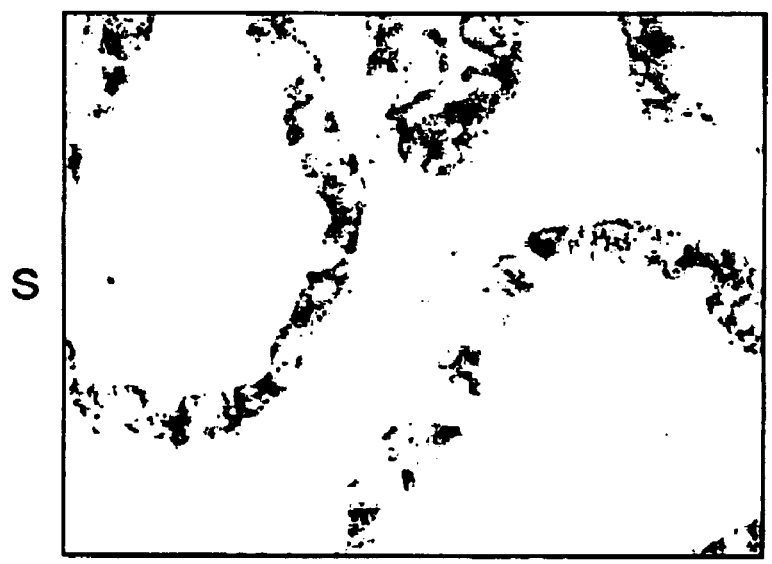

In situ hybridization showed that the expression of TRAITS mRNA is in epithelial cells (FIGS. 7C–7D). This observation indicates that TRAITS plays a role in epithelial cells. The expression pattern of TRAITS is unique and different from that of calreticulin, AM, FPP synthase, and spermidine synthase. The expression of calreticulin, AM, FPP synthase, and spermidine synthase in the seminal vesicles is significantly lower compared to the prostate. Also, the expression of these genes in seminal vesicles is not significantly down-regulated by androgen ablation. Finally, their expression is detectable in every surveyed organ, indicating that their functions are not limited to the male sex accessory organs, as was the case in the rat. TRAITS is expressed and regulated by androgen in both prostate and seminal vesicles.

Figure 15A:
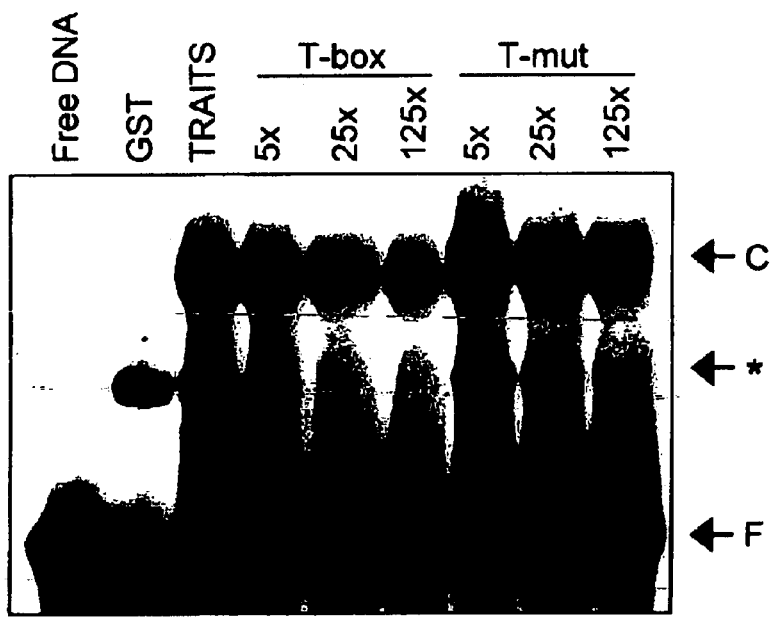
FIGS. 15a–15b demonstrate that TRAITS is a novel transcription factor.

TRAITS contains high density of basic amino acid residues in its N-terminal region and a region rich in serine, glutamine, and aspartic acid resides within its C-terminal region (FIG. 14a). TRAITS is a DNA-binding protein and consistently has a basic amino acid sequence that is often found in DNA binding domain. To further show that TRAITS can bind to DNA, a GST-TRAITS fusion protein was generated and a random binding site selection (RBSS) procedure was performed. As disclosed herein, a hexanucleotide sequence, ACTTTA, termed herein the T-box, is the core TRAITS target element. The specificity of TRAITS binding to the T-box was verified by electrophoretic mobility shift assay (EMSA) with the use of a T-box containing DNA (T-wt) representative of those selected by RBSS (FIG. 15a).

Overexpressed TRAITS exists as a soluble intracellular protein: A GST-TID-1 fusion protein expression vector was constructed using the rat TRAITS cDNA and pGEX-2T (Pharmacia). After transformation into B21 E. coli cells, the GST-TID-1 fusion protein expression was induced by IPTG. The GST-TRAITS was purified by a glutathione-conjugated gel. GST-TID-1 protein was only present in the soluble fraction, suggesting that TRAITS is a soluble protein. A FLAG-tagged TRAITS (fTID-1) mammalian expression vector was also constructed using pCMV-Tag (Stratagene). The fTID-1 expression vector was verified by sequencing and then stably transfected into PC3 and TSU prostate cancer cells. The fTID-1 can be detected in the whole cell extracts at the 35 kDa position in SDS-PAGE gel (FIG. 8B), indicating that TRAITS is present intracellularly as a soluble protein. The TID-1-GFP (green fluorescent protein) fusion protein is localized in the nuclei of LNCaP cells, indicating that TRAITS is a nuclear protein.

Figure 9A:
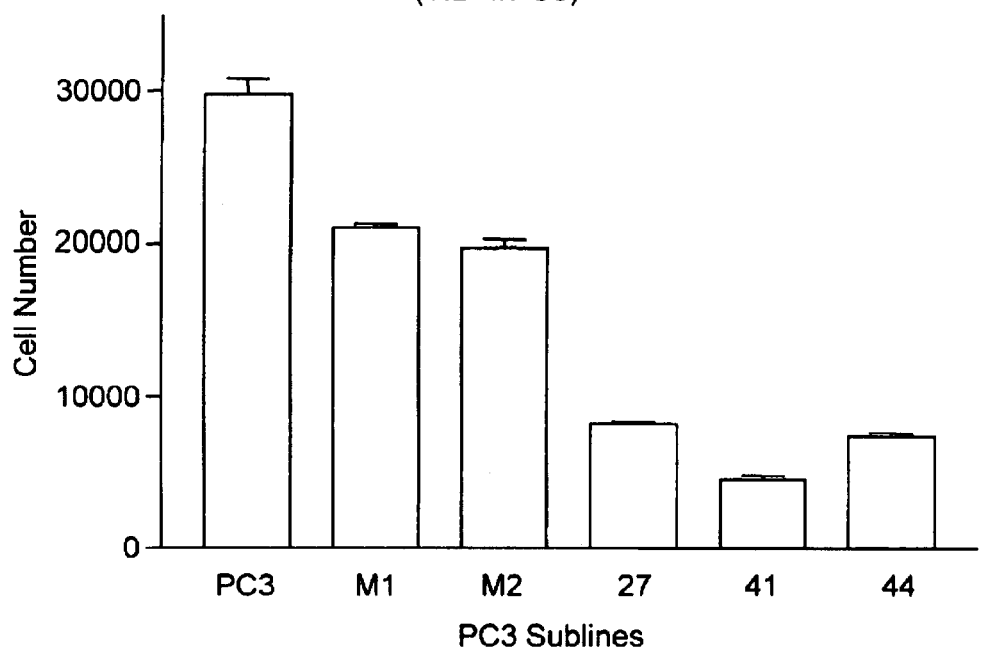
FIG. 9A shows the effect of TID-1 expression on cell proliferation. The cell numbers of the parental PC3, empty pcDNA3.1 vector transfected PC3 sublines M1 and M2, and pcDNA3.1-TID-1 transfected PC3 sublines 27, 41, and 44 were counted after culture in 6-well plates for 4 days.

TRAITS inhibits proliferation of prostate cancer cells in culture and in soft agar: PC3 human prostate cancer cells were stably transfected with a CMV promoter-driven TID-1 expression vector, pcDNA 3.1-TID-1 (Invitrogen). Northern blot analysis showed that the levels of the TRAITS transgene expression in various sublines were similar. Ectopic expression of TID-1 in PC3 cells resulted in a 2-fold reduction in cell numbers (FIG. 9A). The effect of TRAITS overexpression on anchorage-independent growth of PC3 prostate cancer cells was also tested in soft agar. The ectopic expression of TRAITS resulted in the inhibition of the size and number of colonies in soft agar (FIGS. 9B–9G). The ability of a cancer cell line to grow in soft agar often correlates with its aggressiveness [Cifone and Fidler, Proc. Nat. Acad. Sci. USA, 77:1039–43 (1980); and Li et al., J. Nat. Can. Inst., 81:1406–12 (1989)]. This result indicates a tumor suppressive role for TRAITS in prostate cancer.

Figure 8B:
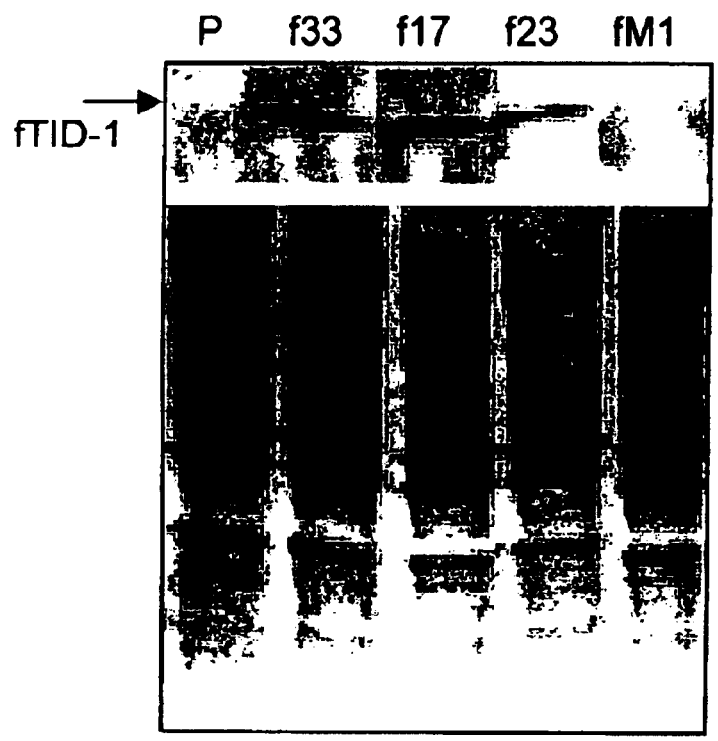
FIG. 8B shows the expression of FLAG tagged TID-1 protein (fTID-1) in PC3 human prostate cancer cells. The PC3 cells were stably transfected with pCMV-Tag-fTID-1 and three stably transfected clones were analyzed (f33, f17, and f23). Parental PC3 (P) and empty vector transfected PC3 (fM1) were included as controls. The whole cell extracts were analyzed on a 10% SDS gene and transferred to a Nitrocellulose membrane. The fTID-1 was detected using M5 anti-FLAG antibody (Sigma). The arrow indicates the fTID-1 band at ~35 kDa position by SDS page gel electrophoresis.

To monitor the expression of the TRAITS protein in transfected cells, TRAITS was tagged with the FLAG epitope and the pCMV-fTID-1 expression vector was generated. PC3 prostate cancer cells were transfected with the pCMV-fTID-1. Whole cell extracts were analyzed by Western blot using the M5 anti-FLAG antibody (Sigma) to identify sublines that express fTID-1 (FIG. 8B). Ectopic expression of fTID-1 in PC3 cells resulted in a 2-fold reduction in cell numbers in 3 independent experiments (FIG. 9H). Similar results were observed when TSU prostate cancer cells were used in the experiment. The fTID-1 (FIG. 9H) and TID-1 (FIG. 9A) caused similar inhibition in the proliferation of the transfected prostate cancer cells. Therefore, the FLAG tag does not interfere with TRAITS function.

Figure 10A:
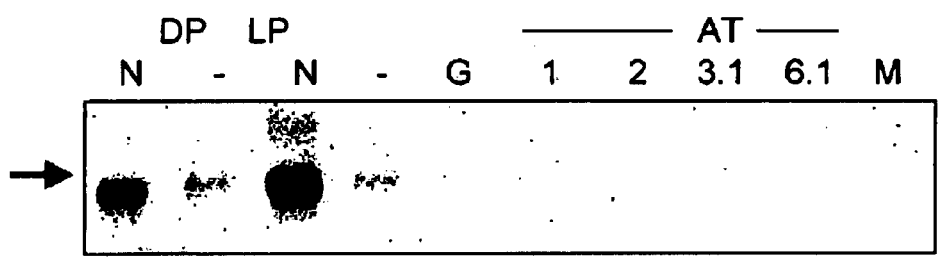
FIGS. 10A–10B demonstrate the down-regulation of TID-1 expression in the rat Dunning prostate tumor cell lines with various aggressiveness [Issacs et al., Prostate 9:261–281 (1986)]. The Dunning cell lines include the G, AT1, AT2, AT3.1, AT6.1, and Mat-Lylu (M), which are derived from the rat dorsolateral prostate. Controls were performed on the dorsal prostate (DP) and the lateral prostate (LP) from the normal rat (N) or the 7-day castrate rat (–). The upper panel (FIG. 10A) is the Northern blot using the rat TID-1 cDNA probe. The arrow indicates the position of the TID-1 mRNA. The bottom panel (FIG. 10B) is the methylene blue staining of the total RNA.
Figure 10B:
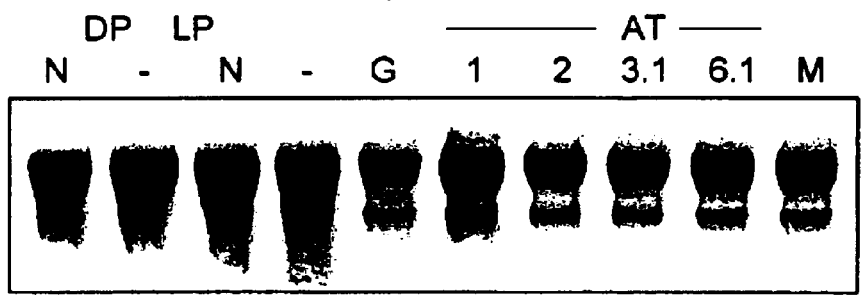

The CMV-fTID-1 expression vector was also transfected into LNCaP, an androgen-responsive human prostate cancer cell line [Horoszewicz et al., Cancer Research 43:1809–18 (1983)], in two different experiments. However, no LNCaP clones expressing fTID-1 were found. This indicates that fTID-1 expression is detrimental to LNCaP cells. The expression of the endogenous TID-1 gene was also not detected in the rat Dunning tumor cell lines (FIGS. 10A–10B) and various human prostate cancer cell lines including LNCaP, PC3, DU145, and TSU cells. The down-regulation of TRAITS in prostate cancer cell lines indicates that TRAITS expression is not compatible with prostate cancer. Stable expression was observed using a CMV promoter-based expression vector. Clonal variations of stably transfected cells can be minimized by assaying multiple, (e.g., three) independent stably transfected sublines.

Figure 11:
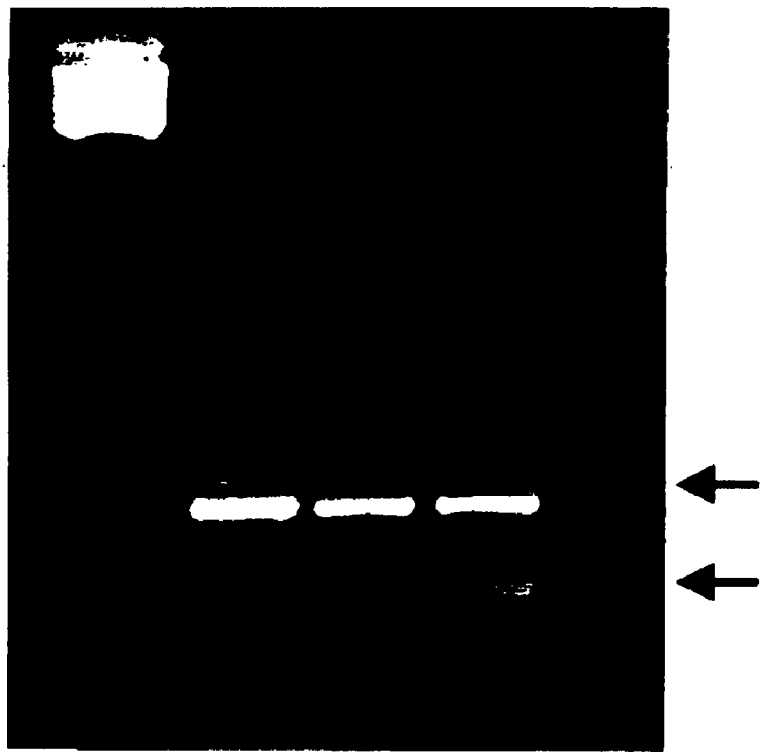
FIG. 11 shows the TID-1 expression in the urogenital sinus during late embryogenesis. RT-PCR analysis of total mouse RNA from adult liver (L), male urogenital sinus at 18 dpc (U), and adult prostate (P) was performed using the SuperScript One-Step RT-PCR system (Gibco). Lane M is the 123 Marker (Gibco). The upper arrow indicates the ribosomal protein RPL-19 control PCR products (560 bp) and the lower arrow indicates the TID-1 PCR products (325 bp). The liver RNA serves as a negative control and the adult prostate as a positive control.

TRAITS is expressed in mouse urogenital sinus during late embryogenesis: One critical period in the development of male sex accessory organs is late embryogenesis. It was therefore determined whether TRAITS is expressed during this critical period in the mouse urogenital sinus. RT-PCR analysis was performed on the total RNA obtained from the urogenital sinus at 18 days post-coitum (dpc). The results showed that the TRAITS mRNA is expressed in the urogenital sinus of the 18-day old embryo (FIG. 11). As in the rat, TRAITS expression is regulated by androgen in the adult mouse ventral prostate, indicating that androgen regulation of TRAITS expression is conserved evolutionarily.

Figure 13A:
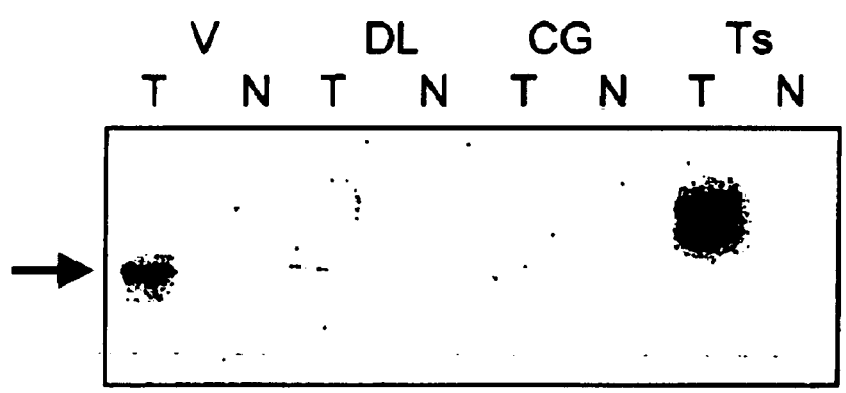
FIGS. 13A–13B show the Northern blot analysis of the transgene expression in the ventral prostate (V), dorsolateral prostate (DL), coagulating gland (CG), and testis (Ts). The top panel (FIG. 13A) was probed with a SV40 sequence which was tagged at the 3'-end of the transgene to provide the poly A signal [Zhang et al., Prostate, 32:16–26 (1997)]. The bottom panel (FIG. 13B) is the methylene blue staining for total RNA. The arrows indicate the predicted size (~1 kb) of mRNA from TID-1 transgene. The mRNA from the TID-1 transgene in the testis is larger than 1 kb, undoubtedly due to alternative post-transcriptional RNA processing.
Figure 13B:
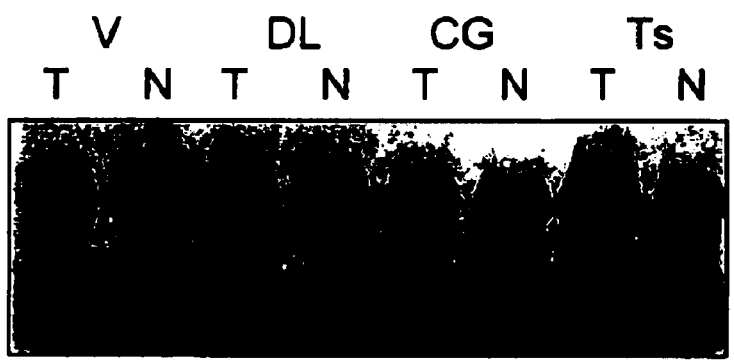

Ectopic expression of TRAITS: Ectopic expression of TRAITS in the ventral prostate alters the regional heterogeneity of the ductal system and significantly enhances (2–3 fold) the epithelial cell number per unit area in the prostate of transgenic mouse. To study the role of TRAITS protein in the prostate in vivo, an expression vector, C3 (I)-TID-1, was generated that expresses TRAITS under the control of the prostate C3(I) promoter [Zhang et al., Prostate, 32:16–26 (1997)]. The C3(I) promoter is androgen-dependent and active only in the ventral prostate and testis. Two transgenic mouse lines were identified by PCR amplification of the tail genomic DNA using primers specific for the TRAITS transgene. Northern blot analysis showed that one line expresses the TRAITS transgene in the ventral prostate and testis (FIGS. 13A–13B). The C3(I)-TID-1 transgenic mice are fertile.

Ectopic expression of TRAITS in the ventral prostate altered the regional heterogeneity of the ductal system and significantly enhanced (2–3 fold) the epithelial cell number per unit area in the ventral prostate of the transgenic mouse (FIGS. 12A–12F). This phenotype was reproducibly observed in three C3(I)-TID-1 transgenic mice using their corresponding non-transgenic littermates as controls. This phenotype indicates that ectopic TRAITS expression enhances proliferation and/or alters differentiation of normal prostatic epithelial cells in vivo. This effect appears to be distinct from its inhibitory effect on the proliferation of prostate cancer cells.

The C3(I)-TID-1 transgenic mice did not exhibit recognizable structural and functional abnormality in their testis.

Serum testosterone levels in transgenic and non-transgenic littermates were 1.191±0.520 ng/ml and 1.076±0.474 ng/ml, respectively. There is no statistically significant difference between these values. In addition, no histological abnormality was observed in the dorsolateral prostate in C3(I)-TID-1 transgenic mice. These results indicate that the abnormality in the ventral prostate of the C3(I)-TID-1 transgenic mice resulted from the TID-1 transgene expression in the ventral prostate.

Figure 15B:
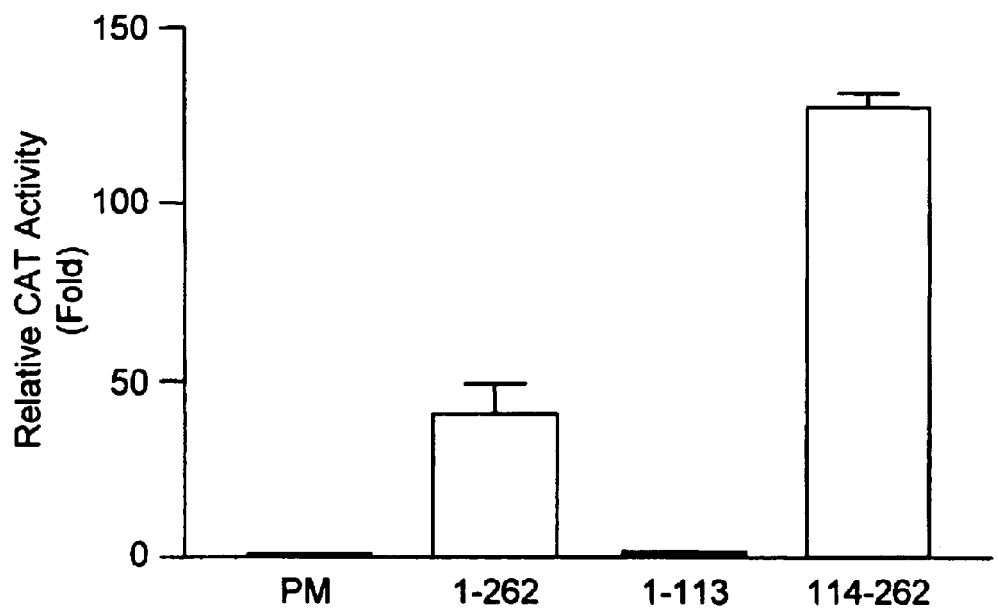

To determine whether TRAITS contains a transactivation domain, mammalian two-hybrid analysis was performed and it was demonstrated that the full-length TRAITS can transactivate the CAT reporter gene expression more than 40 fold (FIG. 15b). Deletion mutagenesis analysis showed that the transactivation domain is located in the C-terminal region (amino acid residues 114–262 of SEQ ID NO:14), which is rich in serine, glutamine, and aspartic acid resides. Interestingly, deletion of the N-terminal region can even enhance the transactivation (FIG. 15b). Similar results have been reported in other genes. A database search did not identify any recognizable DNA binding motif in TRAITS, suggesting that TRAITS belongs to a novel class of transcription factor.

To further characterize the function of TRAITS, green fluorescent protein (GFP) was tagged to TRAITS at its N-terminal or C-terminal ends using pEGFP C1 and pEGFP N3 vector, respectively (Clontech). The GFP-TRAITS or TRAITS-GFP expression vectors were transiently transfected into human prostate cancer cell lines (LNCaP, PC3, DU145 and TSU), rat Dunning prostate tumor cell lines (G, AT1, AT2, AT3.1, AT6.1, and MatLyLu), and non-prostatic cell lines including NIH3T3 and Hela. GFP-TRAITS or TRAITS-GFP is localized in the nuclei of all the transfected cell lines. The nuclear localization of TRAITS is consistent with its function as a transcription factor.

TRAITS ectopic expression in LNCaP cells induces massive cell death: An interesting phenomenon was observed in all the transfected cells, i.e., the cells with TRAITS-GFP or GFP-TRAITS expression exhibited chromatin condensation and plasma membrane blebbing, indicative of programmed cell death. FIG. 16a shows an example of TRAITS-induced apoptosis in PC3 cell line. TRAITS can cause cell death in both p53 wild-type LNCaP cells and p53 deficient PC3, TSU and DU145 cells, which indicates that TRAITS-induced apoptosis is p53-independent. Indeed, one striking observation was that most of the cells expressing the TID-1-GFP fusion protein were dead and detached from the culture dish. In contrast, the cells transfected with GFP expression vector are healthy. These results indicate that TRAITS is a death factor for prostate cancer cells. Moreover, ELL-associated factor (EAF1), a related protein having a striking sequence homology to TRAITS, [Accession No: AF272973 for the human protein recently reported in Simone et al., *Blood* 98:201–209 (2001), the contents of which are hereby incorporated by reference in their entireties,] as disclosed herein, shares this same "death factor" i.e., apoptosis-inducing trait. EAF1 has the nucleotide sequence of SEQ ID NO:19 and the amino acid sequence of SEQ ID NO:20 (see Example 4 below).

Importantly, as disclosed herein, deletion mutagenesis studies showed that the N-terminal region of TRAITS and EAF1 is necessary and sufficient for inducing apoptosis, whereas the C-terminal region, which contains a transactivation domain, is not required for TRAITS to induce apoptosis (FIG. 16c). Similar phenomenon has been observed with yet another transcription factor, E2F-1, which has previously been shown to cause apoptosis, independent of its transactivation domain, in p53 negative Saos-2 cells.

To confirm the apoptotic potential of TRAITS, TRAITS was cloned into a bicistronic expression vector that drives the expression of GFP and TRAITS as separate proteins in the same cell. The expression of untagged TRAITS also efficiently induced chromatin condensation and cell death in the transfected cells. In addition, the fact that TRAITS is a potent cell death inducer is consistent with the inability to stably transfect prostate cancer cells with constitutive untagged TRAITS expression vector.

To further characterize the function of TRAITS, a tripartite fusion protein was established consisting of GFP, TRAITS, and a modified estrogen receptor ligand-binding domain (ER™). The activity of transcription factor-ER fusion proteins can be regulated by 4-hydroxytamoxifen (OHT) but not by endogenous estrogens. The GFP-TRAITS-ER is primarily localized in cytoplasm in the absence of ligand OHT and is translocated into nuclei in the presence of OHT (FIG. 16a). The activation of GFP-TRAITS-ER leads to chromatin condensation, annexin V positive staining, and genomic DNA fragmentation (FIGS. 16a–16b). The FACS analysis of annexin V staining showed that only 3.9% cells were apoptotic in the absence of OHT whereas 60.7% cells were apoptotic in the presence of 300 nM OHT for 72 hours (FIG. 16b). These results further demonstrate that TRAITS induces extensive cell death via apoptosis.

Figure 17A:
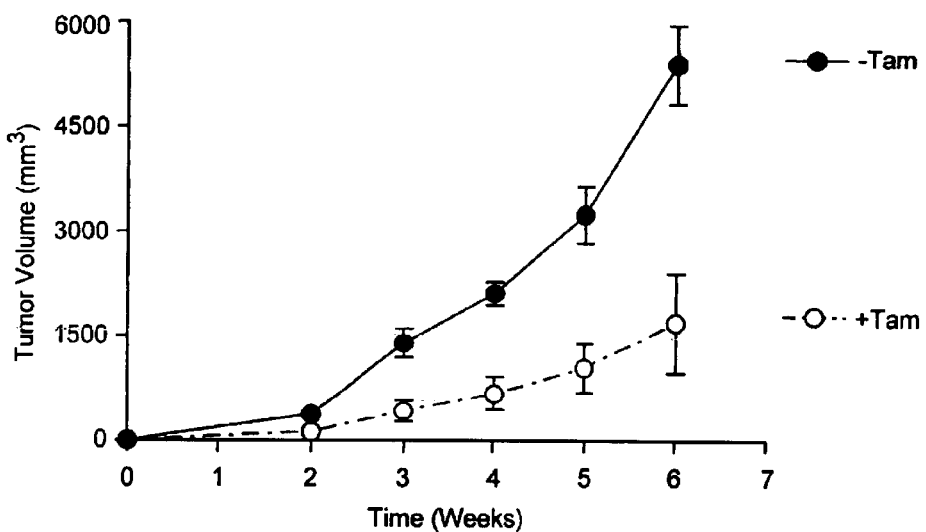
FIG. 17a shows the inhibition of AT6.1 prostatic xenograft tumor growth by TRAITS activation in nude mice. The tamoxifen pellets were implanted at the time of AT6.1 cell injection. The error bars represent S.E.M. The tamoxifen inhibition of AT6.1 tumor growth was statistically significant ($p<0.005$) at every time point of tumor measurement.

The availability of prostate cancer cells stably expressing GFP-TRAITS-ER provided an opportunity to test whether TRAITS can suppress tumor growth. The parental PC3 prostate cancer cells are aggressive and can readily generate xenograft tumors if they were implanted subcutaneously. As expected, implantation of the parental PC3 cells or PC3 sublines expressing GFP-ER yielded xenograft tumors efficiently. However, the PC3 sublines expressing GFP-TRAITS-ER were unable to generate xenograft tumors after subcutaneous injection into nude mice, which indicates that GFP-TRAITS-ER expression could suppress PC3 tumor growth in vivo in the absence of OHT, possibly due to leaky TRAITS activity. Thus, the impact of TRAITS in highly aggressive AT6.1 rat Dunning prostate tumor cell line was tested. The AT6.1 sublines expressing GFP-TRAITS-ER were able to generate xenograft tumors, but at a much slower rate relative to the parental and GFP-ER transfected AT6.1 cells. This suggests that the growth of AT6.1 xenograft tumor is also inhibited by GFP-TRAITS-ER leaky activity in the absence of OHT. As expected, the growth of xenograft tumors derived from AT6.1 sublines expressing GFP-TRAITS-ER was significantly inhibited ($p<0.005$) by tamoxifen administration (FIG. 17a). In contrast, tamoxifen administration had no detectable influence on the growth of xenograft tumors derived from the parental or GFP-ER transfected AT6.1 cells in parallel experiments. This observation showed that the activation of GFP-TRAITS-ER markedly suppressed AT6.1 xenograft prostate tumor growth in nude mice.

Figure 17B:
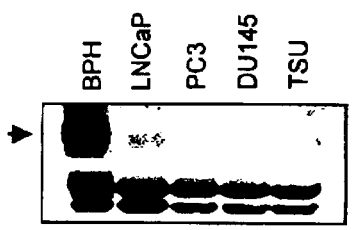
FIG. 17b shows a Northern blot analysis of TRAITS expression in human BPH and prostate cancer cell lines. The loading of total RNA was visualized by methylene blue staining.
Figure 17C:
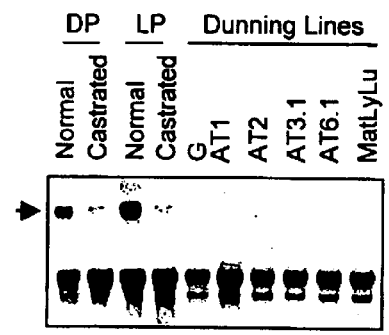
FIG. 17c is the northern blot analysis of TRAITS expression in rat prostatic tissues and cancer cell lines. The loading of total RNA was visualized by methylene blue staining.

If TRAITS is a tumor suppressor important for prostate cancer, its expression should be frequently down-regulated in prostate cancer progression. Northern blot analysis showed that TRAITS expression in human prostate cancer cell lines LNCaP, PC3, DU145, and TSU is down-regulated relative to its expression in human BPH tissues (FIG. 17b). Interestingly, the level of TRAITS mRNA in LNCaP is greater than that in PC3, DU145, and TSU, which inversely correlates with the aggressiveness of these cell lines (FIG. 17b). TRAITS expression is also down-regulated in the Dunning rat prostate cancer cell lines (FIG. 17c). TRAITS down-regulation in all of the prostate cancer cell lines indicates that it is an essential tumor suppressor in prostate cancer.

Figure 17D:
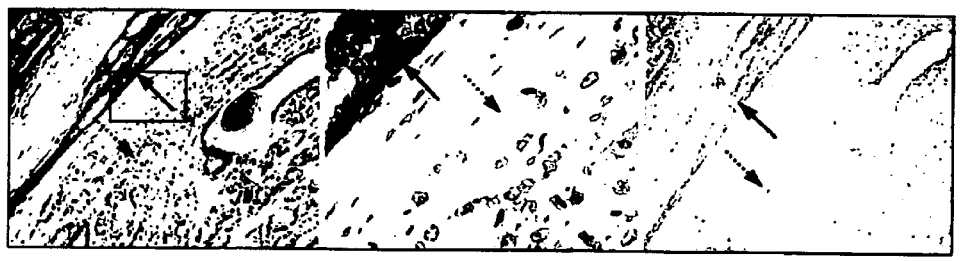
FIG. 17d shows the expression of the TRAITS protein in human prostate cancer specimens. Affinity purified anti-human TRAITS polyclonal antibody was used in immunostaining of radical prostatectomy specimens from 8 patients with advanced prostate cancer (Gleason-score 7 to –10). Seven out of the eight specimens exhibited significant TRAITS down-regulation in prostate cancer cells relative to benign prostatic epithelial cells in the same staining section. A typical TRAITS down-regulation was shown with 20× objective (left) and the boxed area shown at high magnification (middle). A parallel staining without primary antibody (right) was conducted as a control. Blue arrows with solid line point to benign epithelial cells whereas red arrows with broken line indicate cancerous cells.

To determine whether TRAITS is down-regulated in human prostate cancer specimens, an anti-human TRAITS antibody was affinity-purified in order to conduct immunohistochemistry studies. Significant TRAITS down-regulation in advanced prostate cancer cells was observed in 7 out of 8 or 87% of the radical prostatectomy specimens from hormone treatment naïve patients. Typical TRAITS down-regulation was shown in FIG. 17d. This observation provided strong evidence that TRAITS is an important tumor suppressor in prostate cancer progression in vivo.

The results disclosed herein show that TRAITS is a novel testosterone regulated apoptosis inducer and tumor suppressor in prostate cancer. One surprising observation is that TRAITS induction of apoptosis is very potent and effective in all of the surveyed cell lines. Although the exact mechanism of TRAITS induction of apoptosis remains to be elucidated, it appears to be p53-independent because it induces apoptosis in p53-deficient cell lines, such as PC3. The highly conserved N-terminal region of TRAITS, in the absence of the transactivation domain, is necessary and sufficient for apoptosis induction. The observations disclosed herein indicate that TRAITS is one important gene involved in androgen-dependent apoptosis control and/or growth restriction in the prostate. Androgen-dependent growth restriction is critically important for homeostasis of the prostate. Down-regulation of TRAITS should weaken or inactivate this growth restriction, contributing to prostate cancer progression. The finding that inactivation of part of the androgen action pathway, via TRAITS down-regulation, is commonly associated with prostate cancer progression is conceptually significant and facilitates further elucidation of the mechanism of prostate cancer progression.

Example 4

Identification of a Protein Related to TRAITS

As indicated above, exon III of TRAITS is crucial for the ability of TRAITS to induce apoptosis. Therefore, the search for other genes that contained exon III was undertaken. A Blast search of the GenBank database identified a mouse (*Mus musculus*) adult male testis cDNA fragment that was homologous to exon III of TRAITS (accession number:AK016628, released Feb. 8, 2001). This cDNA had been translated to a 197 amino acid protein. Upon inspection, not only did exon III have homology to this protein, but the entire N terminus, (exons I–III) had homology. However, the sequence submitted was missing 71 amino acids of the N-terminus. In fact, the mouse gene (now known as EAF1) was determined herein, to comprise 268 amino acids (not 171 amino acids).

The human genome database was searched with the aid of the open reading frame of the mouse gene. The Blast search showed that a working draft of the human chromosome 3 contained the gene (accession number: NT 005768). The open reading frame for the human protein (now known as EAF1) was then determined based homology with the six exons of the mouse gene. The protein was found to have the amino acid sequence of SEQ ID NO:20 and to be encoded by the nucleic acid sequence of SEQ ID NO:19. An immediate search of GenBank failed to find a match indicating that at the time of the sequence determination, this novel protein had not been disclosed.

Using two pairs of primers and human BPH prostate total RNA amd mouse total RNA as templates, and using the SUPERSCRIPT™ one-step RT-PCR (Gibco) the mouse and human genes were amplified. Their cDNAs were cloned into the pGEM-T vector (Promega) for sequence analysis. The sequences of the human and mouse EAF1 were found to be identical to those determined above.

The human and mouse EAF1's were cloned into pEGFP N3 (Clontech) vectors to form the GFP fusion proteins. After transfection of the vectors into PC3 cell lines, the fusion proteins were found to be localized in the nucleus and more importantly, to cause cell death. Northern blot analysis demonstrated that the EAF1 gene is expressed in all 23 human tissues surveyed (Clontech). The expression levels of EAF1 was compared in four human prostate cancer cell lines. LNCaP cells had the highest level in relation to that determined in TSU, PC3, AND DU145 cells. Interestingly EAF1, unlike TRAITS, is not regulated by androgen in LNCaP cells.

EAF1, is the name provided by Simone et al. [*Blood* 98:201–209 (2001); Accession No: AF272973, released Jun. 21, 2001] who independently isolated the protein using a yeast two-hybrid assay using ELL as bait. Simone et al. also reported that EAF1 has a transactivation domain but did not report the apoptosis-inducing domain.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic add encoding a peptide consisting of amino acid residues 68–113 of SEQ NO:18, wherein said residues induce apoptosis in prostate tumor coils.

2. An isolated nucleic acid encoding a mammalian transcription factor, wherein the mammalian transcription factor is a human protein consisting of amino acid sequence of SEQ ID NO:18, or said protein a human protein having the amino acid sequence of SEQ ID NO:18 comprising a conservative amino acid substitution;
   a) a nuclei localization signal; and
   b) a glutamine rich region; and wherein the transcription factor
      (i) is localized in the nuclei; and
      (ii) its expression is regulated by testosterone.

3. The isolated nucleic acid of claim 2, wherein the nucleic acid consists of the nucleotide sequence of SEQ ID NO:17.

4. A recombinant DNA molecule that is operatively linked to an expression control sequence; wherein the recombinant DNA molecule consists of the nucleic acid of claim 3.

5. An expression vector containing the recombinant DNA molecule of claim 4.

6. An isolated cell that has been transformed with the expression vector of claim 5, wherein the protein encoded by said recombinant DNA molecule is expressed by the cell.

7. The cell of claim 6 which is a mammalian cell.

8. A method of expressing a recombinant transcription factor protein in an isolated cell containing the expression vector of claim 5 comprising culturing the cell in an appropriate cell culture medium under conditions that provide for expression of a recombinant transcription factor by the cell.

9. The method of claim 8, further comprising the step of purifying the recombinant transcription factor.

10. A nucleic acid that fully hybridizes under high stringency conditions 50% formamide, 5+ or 6+ SSC, to the nucleic acid of SEQ ID NO:17, wherein the nucleic acid encodes a transcription factor which induces
   a) a nuclei localization signal; and
   b) a glutamine rich region and wherein the transcription factor
      (i) is localized in the nuclei; and
      (ii) its expression is regulated by testosterone.

* * * * *

UNITED STATES PATENT AND TRADEMARK OFFICE
CERTIFICATE OF CORRECTION

PATENT NO.   : 6,780,984 B2                                              Page 1 of 1
DATED        : August 24, 2004
INVENTOR(S)  : Zhou Wang It is certified that error appears in the above-identified patent and that said Letters Patent is hereby corrected as shown below:

Column 83,
Line 26, "tumor coils" should read -- tumor cells --

Column 84,
Line 36, "5+ or 6+" should read -- 5X or 6X --

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

PATENT NO.      : 6,780,984 B2
APPLICATION NO. : 09/906393
DATED           : August 24, 2004
INVENTOR(S)     : Zhou Wang and Wuhan Xiao It is certified that error appears in the above-identified patent and that said Letters Patent is hereby corrected as shown below:

Col. 1, Line 15

The statement of Government support should read as follows:

This invention was made with government support under R01 DK051193 awarded by National Institutes of Health. The government has certain rights in the invention.

Signed and Sealed this
Seventeenth Day of April, 2012

David J. Kappos
*Director of the United States Patent and Trademark Office*